(12) United States Patent
Blatt et al.

(10) Patent No.: US 7,638,488 B2
(45) Date of Patent: Dec. 29, 2009

(54) USE OF ALPHA-GLUCOSIDASE INHIBITORS TO TREAT ALPHAVIRUS INFECTIONS

(75) Inventors: Lawrence M. Blatt, San Francisco, CA (US); Hua Tan, Daly City, CA (US); Scott Seiwert, Pacifica, CA (US)

(73) Assignee: Intermune, Inc., Brisbane, CA (US)

( * ) Notice: Subject to any disclaimer, the term of this patent is extended or adjusted under 35 U.S.C. 154(b) by 525 days.

(21) Appl. No.: 11/370,535

(22) Filed: Mar. 7, 2006

(65) Prior Publication Data

US 2006/0269517 A1 Nov. 30, 2006

Related U.S. Application Data

(60) Provisional application No. 60/660,074, filed on Mar. 8, 2005, provisional application No. 60/707,891, filed on Aug. 12, 2005.

(51) Int. Cl.
*A61K 38/16* (2006.01)
*A61K 31/70* (2006.01)
*A61K 31/715* (2006.01)
*A61K 31/44* (2006.01)
*A61K 31/445* (2006.01)

(52) U.S. Cl. .............................. 514/8; 514/43; 514/61; 514/299; 514/315; 514/317; 514/326; 514/327; 514/328

(58) Field of Classification Search ................. 546/242, 546/248; 514/315, 317, 326, 327, 330
See application file for complete search history.

(56) References Cited

U.S. PATENT DOCUMENTS

| | | | |
|---|---|---|---|
| 7,256,005 B2 * | 8/2007 | Zitzmann et al. | 435/7.2 |
| 2004/0110795 A1 * | 6/2004 | Zitzmann et al. | 514/317 |
| 2005/0119310 A1 * | 6/2005 | Mueller et al. | 514/328 |
| 2005/0256168 A1 * | 11/2005 | Block et al. | 514/327 |

OTHER PUBLICATIONS

Fischer et al., "Treatment for Hepatitis C Virus and Cannabis Use in Illicit Drug User Patients: Implications and Questions," European Journal of Gastroenterology & Heptatology, 18(10), 1039-1042 (Oct. 2006).*
Sylvestre et al., "Cannabis Use Improves Retention and Virological Outcomes in Patients Treated for Hepatitis C,"European Journal of Gastroenterology & Heptatology, 18(10), 1057-1063 (Oct. 2006); only abstract supplied.*
O'Neil et al. (eds.), The Merck Index, 13th Edition, Merck & Co., Inc., Whitehouse Station, NJ, 2001, only pp. 5, 321 and 1103-1104 supplied: see in particular entries 18, 1906 & 6210.*
(U) Karpas et al., "Aminosugar Derivatives as Potential Anti-Human Immunodeficiency Virus Agents," Proc. National Academy of Sciences, 85 , 9229-9233 (Dec. 1988).*
Chitturi et al., "Hepatotoxicity of Commonly Used Drugs: Nonsteroidal Anti-inflammatory Drugs, Anti-hypertensives, Anticonvulsants, Lipid-Lowering Agents, Psychotropic Drugs," Semin. Liver Disease, 22(2), 169-183 (2002); only abstract supplied.*
Andersson et al., "Inhibition of Glycogen Breakdown by Imino Sugars in vitro and in vivo," Biochemical Pharmacology, 67(4), 697-705 (Feb. 15, 2004).*
Block, T., "Virological Basis of the Broad Antiviral Activity of the Iminosugar Families Called "Glucovirs" and "Alkovirs," Abstracts of Papers, 230th ACS National Meeting, American Chemical Society, Washington, DC, Aug. 28-Sep. 1, 2005, Abstract No. CARB-041.*
Buckvold et al., "Bovine Viral Diarrhea as a Surrogate Model of Heptatiis C Virus for the Evaluation of Antiviral Agents," Antiviral Research, 60(1), 1-15 (Sep. 2003); PubMed I.D.: 14516916; only PubMed abstract supplied by applicant.*

* cited by examiner

*Primary Examiner*—Lawrence E Crane
(74) *Attorney, Agent, or Firm*—Cooley Godward Kronish LLP

(57) ABSTRACT

The present invention provides methods for treating a flavivirus infection, including hepatitis C virus (HCV) infection, in an individual suffering from a flavivirus infection. In some embodiments, the methods involve administering to an individual in need thereof an effective amount of an agent that inhibits enzymatic activity of a membrane-bound α-glucosidase inhibitor. In other embodiments, the methods involve administering to an individual in need thereof effective amounts of an α-glucosidase inhibitor and at least one additional therapeutic agent.

20 Claims, 6 Drawing Sheets

Glyset precose

Median-effect plot

Conservative Isobologram

USE OF ALPHA-GLUCOSIDASE INHIBITORS TO TREAT ALPHAVIRUS INFECTIONS

CROSS-REFERENCE

This application claims the benefit of U.S. Provisional Patent Application Nos. 60/660,074, filed Mar. 8, 2005, and 60/707,891, filed Aug. 12, 2005, which applications are incorporated herein by reference in their entirety.

FIELD OF THE INVENTION

This invention is in the field of treatment of alphavirus infection.

BACKGROUND OF THE INVENTION

The family Alphaviridae includes influenza viruses, parainfluenza viruses, picornaviruses, polio virus, flaviviruses, e.g. yellow fever virus, the four serotypes of dengue virus, Japanese encephalitis virus, Tick-borne encephalitis virus, West Nile virus, hepatitis viruses, and many other disease causing viruses.

Hepatitis C virus is an illustrative example of the family of alphaviruses. Hepatitis C virus (HCV) infection is the most common chronic blood borne infection in the United States. Although the numbers of new infections have declined, the burden of chronic infection is substantial, with Centers for Disease Control estimates of 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with combination therapy using pegylated IFN-$\alpha$ plus ribavirin, 40% to 50% of patients fail therapy, i.e., are nonresponders or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

The high prevalence of chronic HCV infection has important public health implications for the future burden of chronic liver disease in the United States. Data derived from the National Health and Nutrition Examination Survey (NHANES III) indicate that a large increase in the rate of new HCV infections occurred from the late 1960s to the early 1980s, particularly among persons between 20 to 40 years of age. It is estimated that the number of persons with long-standing HCV infection of 20 years or longer could more than quadruple from 1990 to 2015, from 750,000 to over 3 million. The proportional increase in persons infected for 30 or 40 years would be even greater. Since the risk of HCV-related chronic liver disease is related to the duration of infection, with the risk of cirrhosis progressively increasing for persons infected for longer than 20 years, this will result in a substantial increase in cirrhosis-related morbidity and mortality among patients infected between the years of 1965-1985.

Fibrosis occurs as a result of a chronic toxic insult to the liver, such as chronic hepatitis C virus (HCV) infection, autoimmune injury, and chronic exposure to toxins such as alcohol. Chronic toxic insult leads to repeated cycles of hepatocyte injury and repair accompanied by chronic inflammation. Over a variable period of time, abnormal extracellular matrix progressively accumulates as a consequence of the host's wound repair response. Left unchecked, this leads to increasing deposition of fibrous material until liver architecture becomes distorted and the liver's regenerative ability is compromised. The progressive accumulation of scar tissue within the liver finally results in the histopathologic picture of cirrhosis, defined as the formation of fibrous septae throughout the liver with the formation of micronodules.

There is a need in the art for methods of treating alphavirus infections in general, and HCV infection in particular. The present invention addresses this need, and provides related advantages.

Literature

U.S. Pat. Nos. 5,252,714; 5,382,657; 5,539,063; 5,559,213; 5,672,662; 5,747,646; 5,766,581; 5,792,834; 5,795,569; 5,798,232; 5,824,784; 5,834,594; 5,849,860; 5,928,636; 5,951,974; 5,595,732; 5,981,709; 6,005,075; 6,180,096; 6,250,469; 6,277,830. PCT Publication No. WO 99/37779. Chamov et al. (1994) *Bioconj. Chem.* 5:133-140; Harris et al. (2001) *Clin. Pharmacokinet.* 40:539-551; Reddy (2000) *Ann. Pharmacother.* 34:915-923; Reddy et al. (2002) *Adv. Drug Deliv. Rev.* 54:571-586.

METAVIR (1994) Hepatology 20:15-20; Brunt (2000) Hepatol. 31:241-246; Alpini (1997) J. Hepatol. 27:371-380; Baroni et al. (1996) Hepatol. 23:1189-1199; Czaja et al. (1989) Hepatol. 10:795-800; Grossman et al. (1998) J. Gastroenterol. Hepatol. 13:1058-1060; Rockey and Chung (1994) J. Invest. Med. 42:660-670; Sakaida et al. (1998) J. Hepatol. 28:471-479; Shi et al. (1997) Proc. Natl. Acad. Sci. USA 94:10663-10668; Baroni et al. (1999) Liver 19:212-219; Lortat-Jacob et al. (1997) J. Hepatol. 26:894-903; Llorent et al. (1996) J. Hepatol. 24:555-563; U.S. Pat. No. 5,082,659; European Patent Application EP 294,160; U.S. Pat. No. 4,806,347; Balish et al. (1992) J. Infect. Diseases 166:1401-1403; Katayama et al. (2001) J. Viral Hepatitis 8:180-185; U.S. Pat. No. 5,082,659; U.S. Pat. No. 5,190,751; U.S. Pat. No. 4,806,347; Wandl et al. (1992) Br. J. Haematol. 81:516-519; European Patent Application No. 294,160; Canadian Patent No. 1,321,348; European Patent Application No. 276,120; Wandl et al. (1992) Sem. Oncol. 19:88-94; Balish et al. (1992) J. Infectious Diseases 166:1401-1403; Van Dijk et al. (1994) Int. J. Cancer 56:262-268; Sundmacher et al. (1987) Current Eye Res. 6:273-276; U.S. Pat. Nos. 6,172,046; 6,245,740; 5,824,784; 5,372,808; 5,980,884; published international patent applications WO 96/21468; WO 96/11953; Torre et al. (2001) J. Med. Virol. 64:455-459; Bekkering et al. (2001) J. Hepatol. 34:435-440; Zeuzem et al. (2001) Gastroenterol. 120:1438-1447; Zeuzem (1999) J. Hepatol. 31:61-64; Keeffe and Hollinger (1997) Hepatol. 26:101S-107S; Wills (1990) Clin. Pharmacokinet. 19:390-399; Heathcote et al. (2000) New Engl. J. Med. 343:1673-1680; Husa and Husova (2001) Bratisl. Lek. Listy 102:248-252; Glue et al. (2000) Clin. Pharmacol. 68:556-567; Bailon et al. (2001) Bioconj. Chem. 12:195-202; and Neumann et al. (2001) Science 282:103; Zalipsky (1995) Adv. Drug Delivery Reviews S. 16, 157-182; Mann et al. (2001) Lancet 358:958-965; Zeuzem et al. (2000) New Engl. J. Med. 343:1666-1672; U.S. Pat. Nos. 5,985,265; 5,908,121; 6,177,074; 5,985,263; 5,711,944; 5,382,657; and 5,908,121; Osborn et al. (2002) J. Pharmacol. Exp. Therap. 303:540-548; Sheppard et al.

(2003) *Nat. Immunol.* 4:63-68; Chang et al. (1999) *Nat. Biotechnol.* 17:793-797; Adolf (1995) *Multiple Sclerosis* 1 Suppl. 1:S44-S47.

Pavlovic et al. (2003) *Proc. Natl. Acad. Sci. USA* 100:6104-6108; Dwek et al. (2002) *Nature Rev. Drug Discovery* 1:65-75; Wu et al. (2002) *J. Virol.* 76:3596-3604; Mehta et al. (2002) *Antimicrobial Agents and Chemotherapy* 46:4004-4008; Mehta et al. (2001) *Hepatol.* 33:1488-1495; Durantel et al. (2001) *J. Virol.* 75:8987-8998; Mehta et al. (1998) *FEBS Lett.* 430:17-22; Zitzmann et al. (1999) *Proc. Natl. Acad. Sci. USA* 96:11878-11882; Terrault and Ma (2001) *Hepatol.* 33:1544-1546; U.S. Patent Publication No. 2004/0110795.

SUMMARY OF THE INVENTION

The present invention provides methods for treating a flavivirus infection, including hepatitis C virus (HCV) infection, in an individual suffering from a flavivirus infection. In some embodiments, the methods involve administering to an individual in need thereof an effective amount of an agent that inhibits enzymatic activity of a membrane-bound $\alpha$-glucosidase. In other embodiments, the methods involve administering to an individual in need thereof effective amounts of an $\alpha$-glucosidase inhibitor and at least one additional therapeutic agent.

DEFINITIONS

Figure 1:
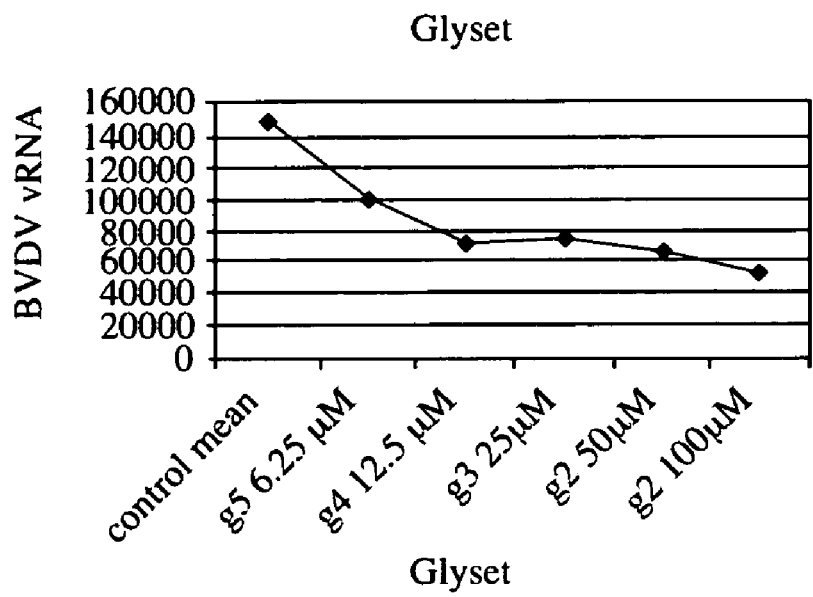
FIG. 1 depicts the effect of various amounts of Glyset® miglitol $\alpha$-glucosidase inhibitor on BVDV vRNA.
Figure 2:
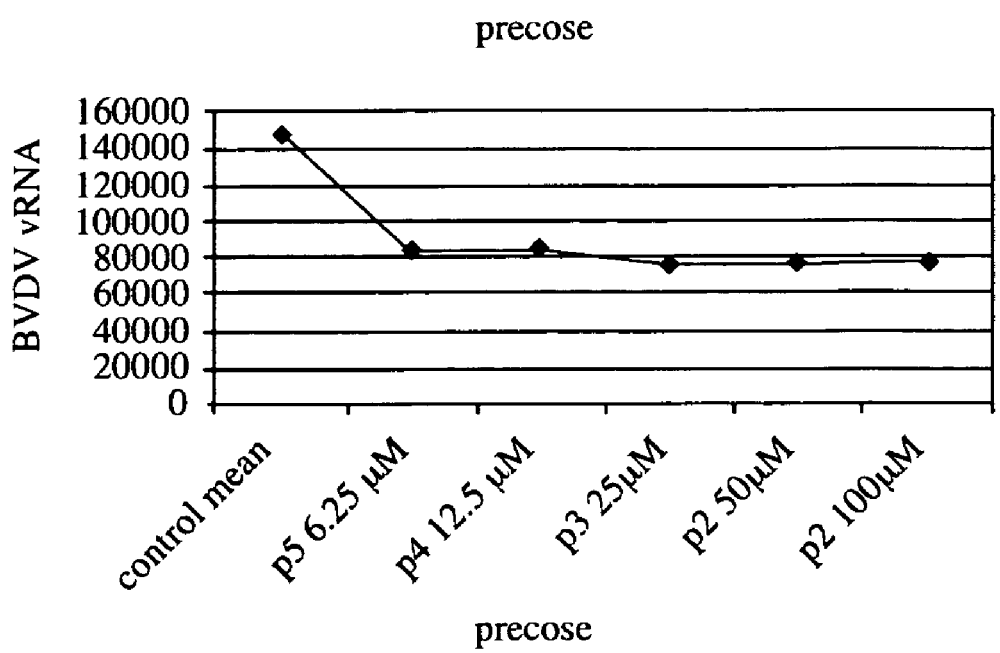
FIG. 2 depicts the effect of various amounts of Precose® acarbose $\alpha$-glucosidase inhibitor on BVDV vRNA.
Figure 3:
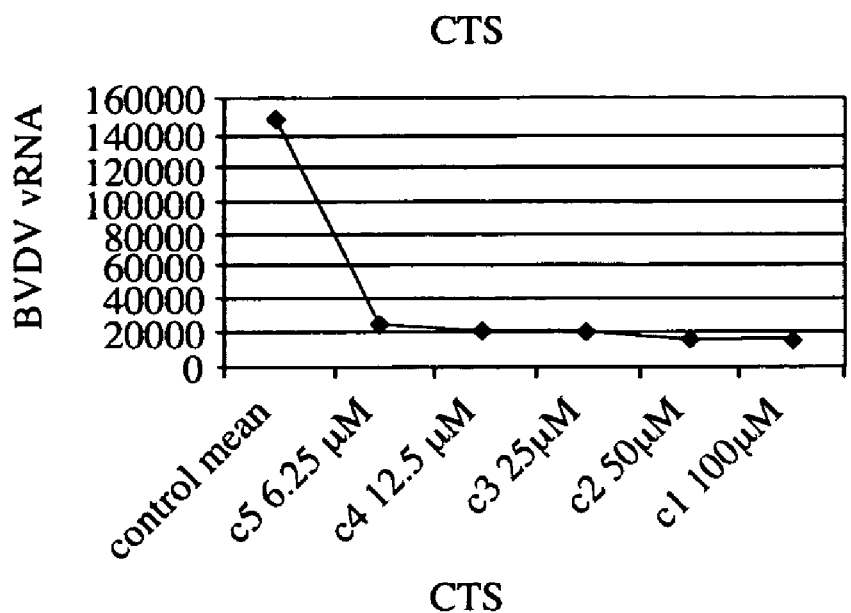
FIG. 3 depicts the effect of various amounts of castanospermine (CTS) on BVDV vRNA.
Figure 4:
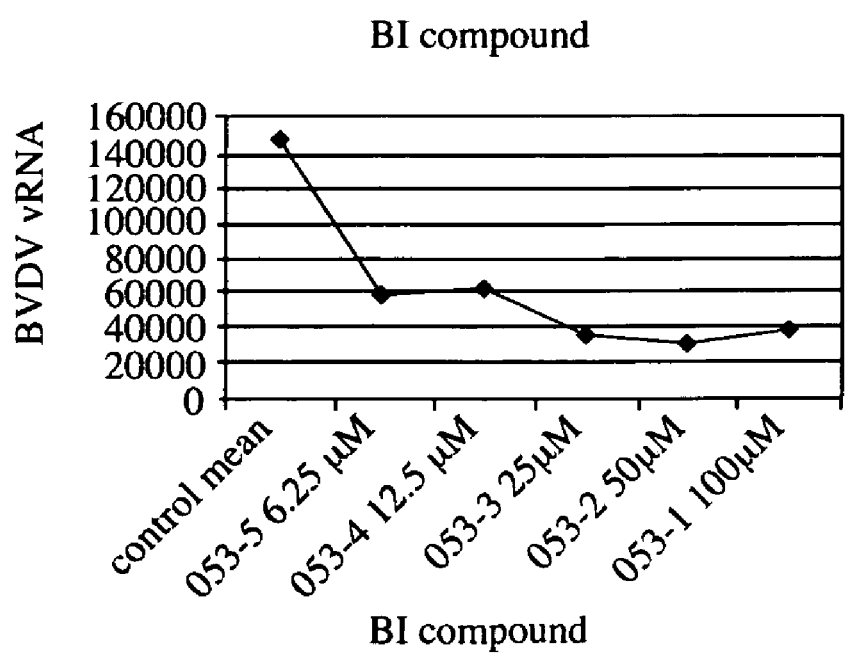
FIG. 4 depicts the effect of various amounts of HCV NS3 inhibitor compound BILN 2061 on BVDV vRNA.
Figure 5:
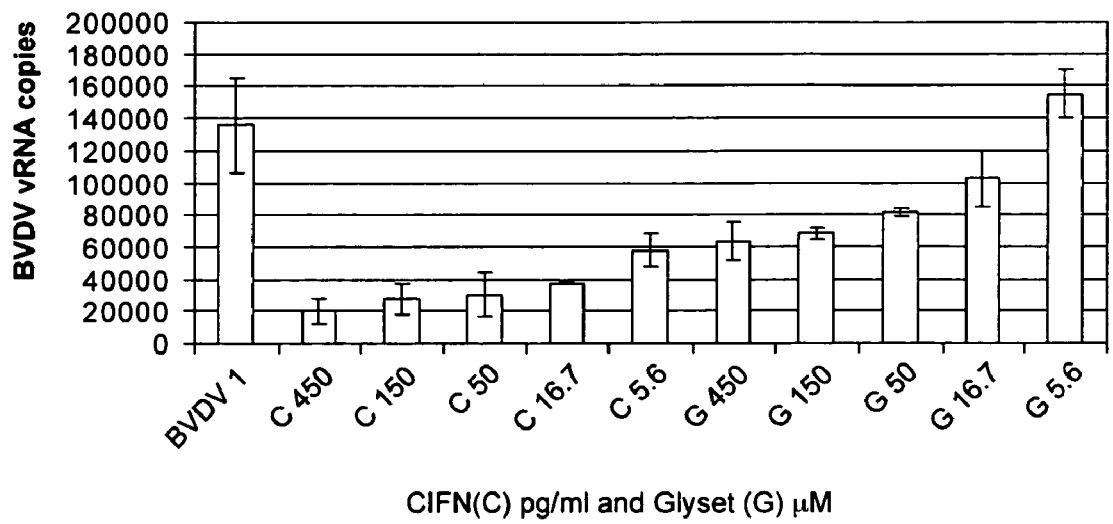
FIG. 5 depicts the effect of various amounts of CIFN or Glyset® miglitol on BVDV vRNA.
Figure 6:
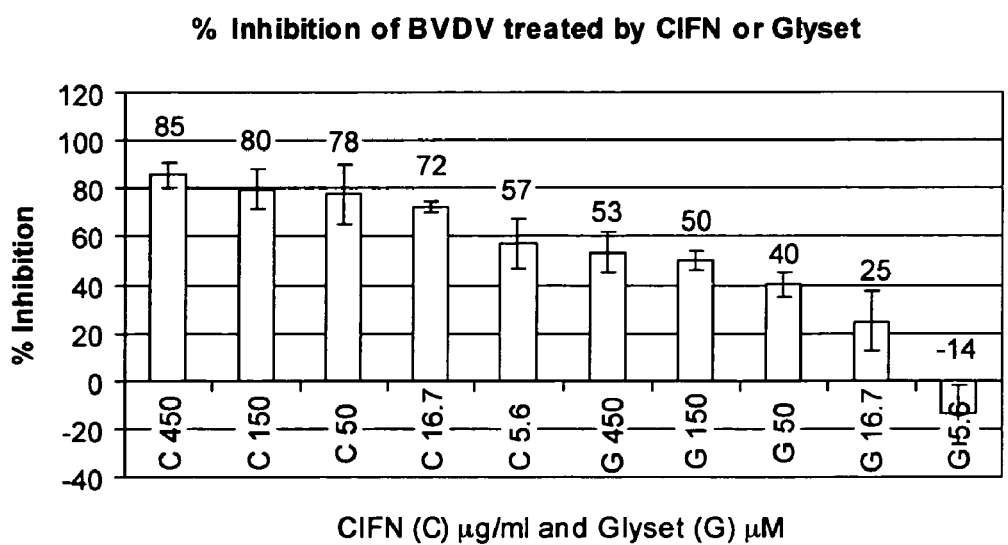
FIG. 6 depicts the percent inhibition of BVDV treated with CIFN or Glyset® miglitol.
Figure 7:
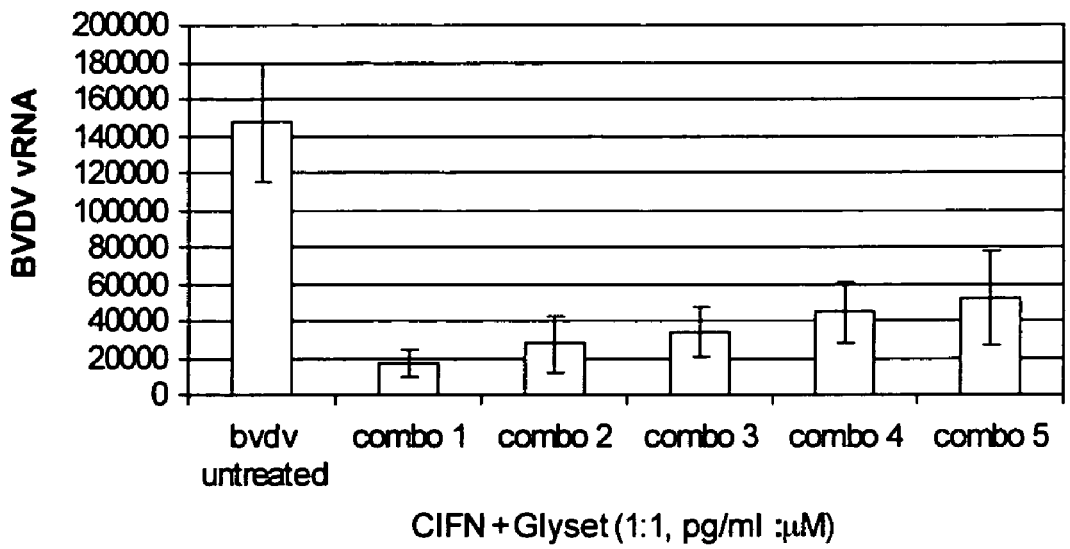
FIG. 7 depicts the effect of the combination of various amounts of CIFN and Glyset® miglitol on BVDV vRNA.
Figure 8:
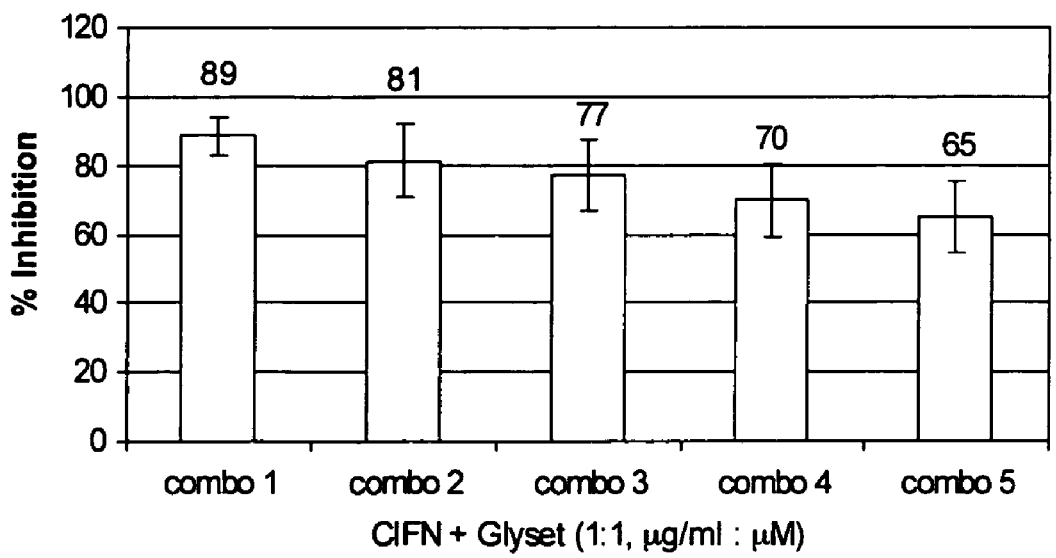
FIG. 8 depicts the percent inhibition of BVDV treated with a combination of CIFN and Glyset® miglitol.
Figure 9:
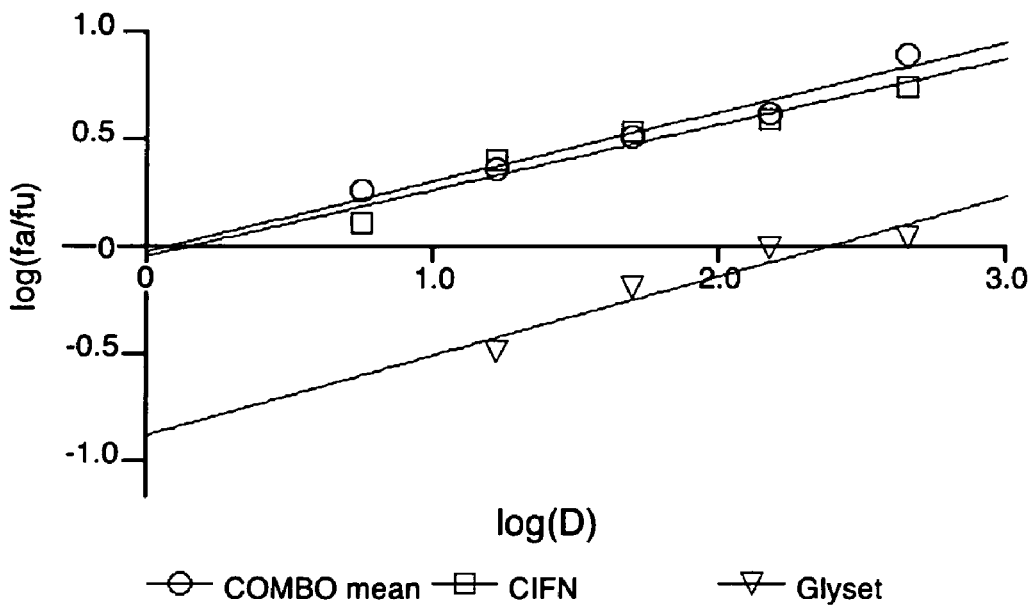
FIG. 9 is a median-effect plot of the effect of CIFN alone, Glyset® miglitol alone, or the CIFN+Glyset® miglitol combination.
Figure 10:
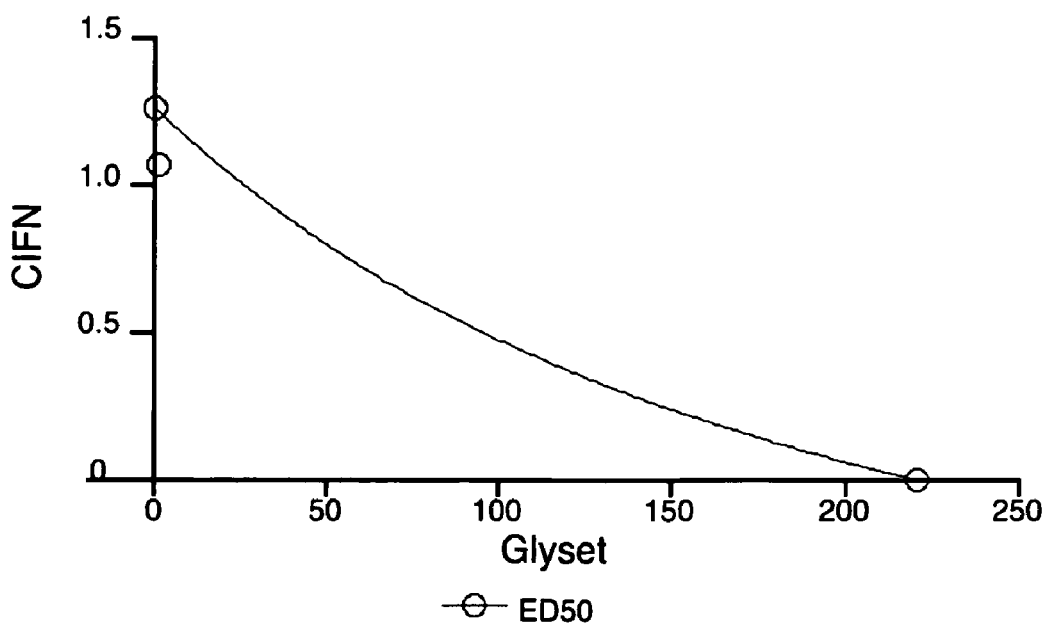
FIGS. 10, 11, and 12 are conservative isobolograms for various concentration ranges of CIFN and Glyset® miglitol.
Figure 11:
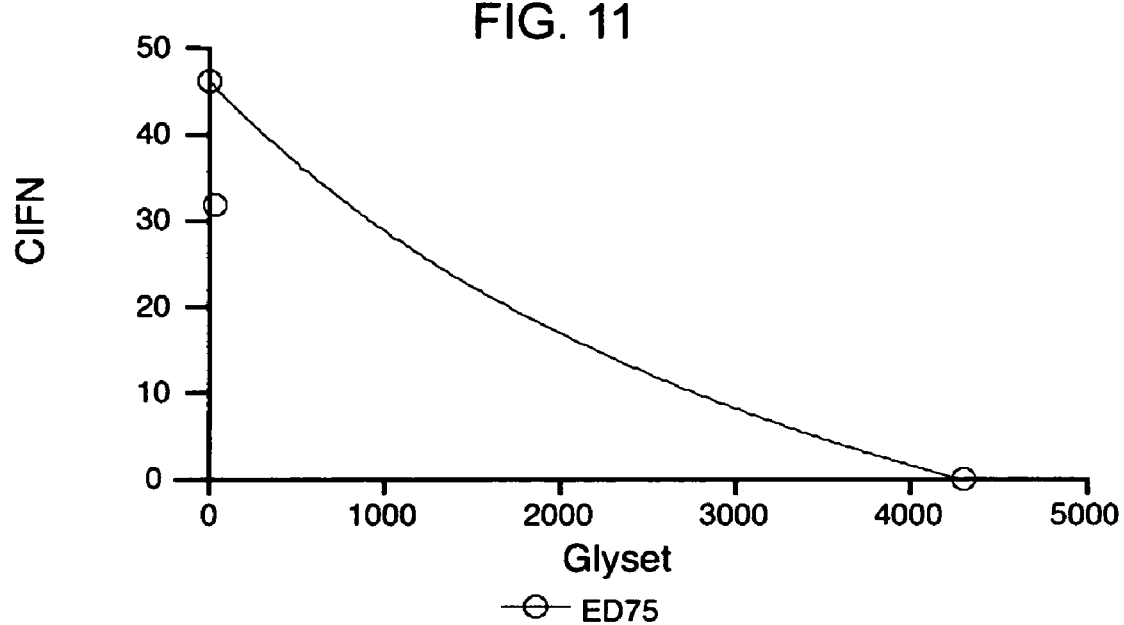
Figure 12:
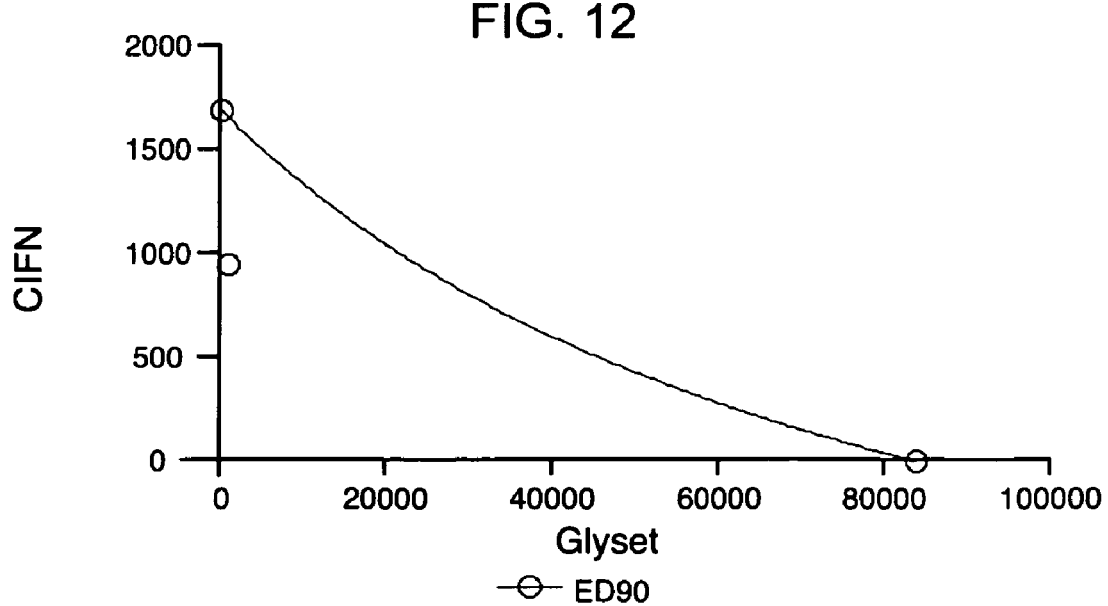

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease (as in liver fibrosis that can result in the context of chronic HCV infection); (b) inhibiting the disease, i.e., arresting its development; and (c) relieving the disease, i.e., causing regression of the disease.

As used herein, the term "flavivirus" includes any member of the family Flaviviridae, including, but not limited to, Dengue virus, including Dengue virus 1, Dengue virus 2, Dengue virus 3, Dengue virus 4 (see, e.g., GenBank Accession Nos. M23027, M19197, A34774, and M14931); Yellow Fever Virus; West Nile Virus; Japanese Encephalitis Virus; St. Louis Encephalitis Virus; Bovine Viral Diarrhea Virus (BVDV); and Hepatitis C Virus (HCV); and any serotype, strain, genotype, subtype, quasispecies, or isolate of any of the foregoing. Where the flavivirus is HCV, the HCV is any of a number of genotypes, subtypes, or quasispecies, including, e.g., genotype 1, including 1a and 1b, 2, 3, 4, 6, etc. and subtypes (e.g., 2a, 2b, 3a, 4a, 4c, etc.), and quasispecies.

The terms "individual," "host," "subject," and "patient" are used interchangeably herein, and refer to a mammal, including, but not limited to, primates, including simians and humans.

The term "treatment failure patients" (or "treatment failures") as used herein generally refers to HCV-infected patients who failed to respond to previous therapy for HCV (referred to as "non-responders") or who initially responded to previous therapy, but in whom the therapeutic response was not maintained (referred to as "relapsers"). The previous therapy generally can include treatment with IFN-$\alpha$ monotherapy or IFN-$\alpha$ combination therapy, where the combination therapy may include administration of IFN-$\alpha$ and an antiviral agent such as ribavirin.

As used herein, the term "hepatic fibrosis," used interchangeably herein with "liver fibrosis," refers to the growth of scar tissue in the liver that can occur in the context of a chronic hepatitis infection.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, $\gamma$-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

As used herein, the term "HCV enzyme inhibitor" refers to any agent that inhibits an enzymatic activity of an enzyme encoded by HCV. The term "HCV enzyme inhibitor" includes, but is not limited to, agents that inhibit HCV NS3 protease activity; agents that inhibit HCV NS3 helicase activity; and agents that inhibit HCV NS5B RNA-dependent RNA polymerase activity.

As used herein, the terms "HCV NS3 protease inhibitor" and "NS3 protease inhibitor" refer to any agent that inhibits the protease activity of HCV NS3/NS4A complex. Unless otherwise specifically stated, the term "NS3 inhibitor" is used interchangeably with the terms "HCV NS3 protease inhibitor" and "NS3 protease inhibitor."

As used herein, the terms "HCV NS5B inhibitor," "NS5B inhibitor," "HCV NS5B RNA-dependent RNA polymerase inhibitor," "HCV RDRP inhibitor," and "RDRP inhibitor," refer to any agent that inhibits HCV NS5B RNA-dependent RNA polymerase activity.

As used herein, the term "nucleoside" refers to a compound composed of any pentose or modified pentose moiety attached to a specific position of a heterocycle or to the natural position of a purine (9-position) or pyrimidine (1-position) or to the equivalent position in an analog.

As used herein, the term "nucleotide" refers to a phosphate ester substituted on the 5'-position of a nucleoside.

As used herein, the term "heterocycle" refers to a monovalent saturated or unsaturated carbocyclic radical having at least one hetero atom, such as N, O, S, Se or P, within the ring, each available position of which can be optionally substituted, independently, with, e.g., hydroxyl, oxo, amino, imino, lower alkyl, bromo, chloro and/or cyano. Included within the term "heterocycle" are purines and pyrimidines.

As used herein, the term "purine" refers to nitrogenous bicyclic heterocycles.

As used herein, the term "pyrimidine" refers to nitrogenous monocyclic heterocycles.

As used herein, the term "L-nucleoside" refers to a nucleoside compound that has an L-ribose sugar moiety.

As used herein, the term "a Type II interferon receptor agonist" refers to any naturally-occurring or non-naturally-occurring ligand of a human Type II interferon receptor which binds to and causes signal transduction via the receptor. Type II interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

As used herein, the term "alphavirus," and its grammatical variants, refers to a group of viruses characterized by (i) an RNA genome (ii) viral replication in the cytoplasm of host cells and (iii) no DNA phase occurs in the viral replication cycle.

The term "hepatitis virus infection" refers to infection with one or more of hepatitis A, B, C, D, or E virus, with blood-borne hepatitis viral infection being of particular interest, particularly hepatitis C virus infection.

The term "therapeutically effective amount" is meant an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "sustained viral response" (SVR; also referred to as a "sustained response" or a "durable response"), as used herein, refers to the response of an individual to a treatment regimen for HCV infection, in terms of serum HCV titer. Generally, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, or at least about six months following cessation of treatment.

As used herein, the term "hepatic fibrosis," used interchangeably herein with "liver fibrosis," refers to the growth of scar tissue in the liver that can occur in the context of a chronic hepatitis infection.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

The term "dosing event" as used herein refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectible system); and a single subcutaneous injection followed by installation of a continuous delivery system.

"Continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

"Controlled release" as used herein (e.g., in the context of "controlled drug release") is meant to encompass release of substance (e.g., a Type I interferon receptor agonist, e.g., IFN-α) at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

"Patterned" or "temporal" as used in the context of drug delivery is meant delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during any 8 hour interval in the pre-selected period never falls to zero. Furthermore, "substantially continuous" drug delivery can also encompass delivery of drug at a substantially constant, pre-selected rate or range of rates (e.g., amount of drug per unit time, or volume of drug formulation for a unit time) that is substantially uninterrupted for a pre-selected period of drug delivery.

By "substantially steady state" as used in the context of a biological parameter that may vary as a function of time, it is meant that the biological parameter exhibits a substantially constant value over a time course, such that the area under the curve defined by the value of the biological parameter as a function of time for any 8 hour period during the time course (AUC8 hr) is no more than about 20% above or about 20% below, and preferably no more than about 15% above or about 15% below, and more preferably no more than about 10% above or about 10% below, the average area under the curve of the biological parameter over an 8 hour period during the time course (AUC8 hr average). The AUC8 hr average is defined as the quotient (q) of the area under the curve of the biological parameter over the entirety of the time course (AUCtotal) divided by the number of 8 hour intervals in the time course (ttotal ⅓ days), i.e., q=(AUCtotal)/(ttotal ⅓ days). For example, in the context of a serum concentration of a drug, the serum concentration of the drug is maintained at a substantially steady state during a time course when the area under the curve of serum concentration of the drug over time for any 8 hour period during the time course (AUC8 hr) is no more than about 20% above or about 20% below the average area under the curve of serum concentration of the drug over an 8 hour period in the time course (AUC8 hr average), i.e., the AUC8 hr is no more than 20% above or 20% below the AUC8 hr average for the serum concentration of the drug over the time course.

As used herein, any compound or agent described as "effective for the avoidance or amelioration of side effects induced by a Type I interferon receptor agonist," or as "effective for reducing or eliminating the severity or occurrence of side effects induced by a Type I interferon receptor agonist," or any compound or agent described by language with a meaning similar or equivalent to that of either of the foregoing quoted passages, is/are defined as a compound(s) or agent(s) that when co-administered to a patient in an effective amount along with a given dosing regimen of a subject combination therapy, abates or eliminates the severity or occurrence of side effects experienced by a patient in response to the given dosing regimen of the subject combination therapy, as compared to the severity or occurrence of side effects that would have been experienced by the patient in response to the same dosing regimen of the subject combination therapy without co-administration of the agent.

In many embodiments, the effective amounts of an inhibitor of an α-glucosidase inhibitor and a second therapeutic agent are synergistic amounts. As used herein, a "synergistic combination" or a "synergistic amount" of an inhibitor of an α-glucosidase inhibitor and a second therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the α-glucosidase inhibitor when administered at that same dosage as a monotherapy and (ii) the therapeutic or prophylactic benefit of the second therapeutic agent when administered at the same dosage as a monotherapy.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an α-glucosidase inhibitor" includes a plurality of such inhibitors and reference to "the active agent" includes reference to one or more active agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods for treating alphavirus infections; methods of treating flavivirus infections; methods of treating hepatitis C virus (HCV) infections; methods of treating West Nile virus (WNV) infection; methods of reducing liver fibrosis; methods of increasing liver function in an individual suffering from liver fibrosis; methods of reducing the incidence of complications associated with HCV and cirrhosis of the liver; and methods of reducing viral load, or reducing the time to viral clearance, or reducing morbidity or mortality in the clinical outcomes, in patients suffering from flavivirus infection. The methods generally involve administering to an individual in need thereof an effective amount of an agent that inhibits enzymatic activity of an α-glucosidase, in monotherapy or in combination therapy.

The methods and compositions described herein are generally useful in treatment of any alphavirus. Treatment of HCV infection is of particular interest in some embodiments. Reference to HCV herein is for illustration only and is not meant to be limiting.

Whether a subject method is effective in treating an alphaviral infection can be determined by a reduction in number or length of hospital stays, a reduction in time to viral clearance, a reduction of morbidity or mortality in clinical outcomes, a reduction in viral burden, or other indicator of disease response in the patient.

In general, an effective amount of an agent that inhibits enzymatic activity of an α-glucosidase is an amount that is effective to reduce the time to viral clearance, or an amount that is effective to reduce morbidity or mortality in the clinical course of the disease, or an amount that is effective to improve some other indicator of disease response (e.g., an amount that is effective to reduce viral load; achieve a sustained viral response; etc.).

In some embodiments, the present invention provides for the treatment of an HCV infection. Whether a subject method is effective in treating an HCV infection can be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

Monotherapy

The present invention provides methods for treating alphavirus infections; methods of treating flavivirus infections; methods of treating hepatitis C virus (HCV) infections; methods of treating West Nile virus (WNV) infection; methods of reducing liver fibrosis; methods of increasing liver function in an individual suffering from liver fibrosis; methods of reducing the incidence of complications associated with HCV and cirrhosis of the liver; and methods of reducing viral load, or reducing the time to viral clearance, or reducing morbidity or mortality in the clinical outcomes, in patients suffering from flavivirus infection. The methods generally involve administering to an individual in need thereof an effective amount of an agent that inhibits enzymatic activity of an α-glucosidase, in monotherapy.

In these embodiments, the method involves administering an effective amount of an agent that inhibits enzymatic activity of a membrane-bound α-glucosidase. In some embodiments, an effective amount of an agent that inhibits enzymatic activity of a membrane-bound α-glucosidase is an amount that is effective to reduce viral titers to undetectable levels, e.g., to about 1000 to about 5000, to about 500 to about 1000, or to about 100 to about 500 genome copies/mL serum. In some embodiments, an effective amount of an agent that inhibits enzymatic activity of a membrane-bound α-glucosidase is an amount that is effective to reduce viral load to lower than 100 genome copies/mL serum.

In some embodiments, an effective amount of an agent that inhibits enzymatic activity of a membrane-bound α-glucosidase is an amount that is effective to achieve a 1.5-log, a 2-log, a 2.5-log, a 3-log, a 3.5-log, a 4-log, a 4.5-log, or a 5-log reduction in viral titer in the serum of the individual.

Agents Suitable for Use in Monotherapy

Agents that are suitable for use in a subject treatment method are agents that inhibit enzymatic activity of a membrane-bound α-glucoside hydrolase. In some embodiments, the agent is one that inhibits enzymatic activity of a membrane-bound intestinal α-glucoside hydrolase (α-glucosidase). Membrane-bound intestinal α-glucosidases hydrolyze oligosaccharides and disaccharides to glucose and other monosaccharides in the brush border of the small intestine.

The term "membrane-bound" refers to the association of the α-glucosidase with the plasma membrane of a cell.

Agents that are specifically excluded from use in a subject monotherapy include agents that inhibit an endoplasmic reticulum (ER) α-glucosidase, such as an ER α-glucosidase I, or an ER α-glucosidase II, e.g., agents that inhibit more than about 20% of the activity of an ER α-glucosidase. Agents that are specifically excluded from use in a subject monotherapy also include agents that inhibit ceramide-specific glucosyltransferase (CerGlcT), e.g., agents that inhibit more than about 20% of the activity of a CerGlcT. Specific agents that are excluded from use in a subject treatment method include deoxynojirimycin (DNJ), deoxygalactojirimycin (DGJ), N-butyl-deoxynojirimycin (NB-DNJ), N-nonyl-deoxynojirimycin (NN-DNJ), N-butyl-deoxygalactojirimycin (NB-DGJ), N-nonyl-deoxygalactojirimycin (NN-DGJ), NN-6deoxy-DGJ, N7-oxadecyl-DNJ, N7-oxanony-6deoxy-DGJ, perbutylated-N-butyl-1-deoxynojirimycin (p-N-butyl-DNJ), and 6-O-butanoyl castanospermine.

An agent that is suitable for use in a subject monotherapy is an agent that inhibits enzymatic activity of a membrane-bound α-glucosidase by at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the enzymatic activity of the membrane-bound α-glucosidase in the absence of the agent.

A suitable agent is an agent that preferentially inhibits enzymatic activity of a membrane-bound α-glucosidase, e.g., the agent inhibits enzymatic activity of a membrane-bound α-glucosidase preferentially, compared to the inhibition, if any, by the agent of an ER-α-glucosidase. In other words, a suitable agent inhibits enzymatic activity of a membrane-bound α-glucosidase and if the agent inhibits an ER-α-glucosidase at all, the agents inhibits less than about 20%, less than about 15%, less than about 10%, less than about 5%, less than about 2%, or less than about 1%, of the activity of an ER-α-glucosidase.

In some embodiments, a suitable agent is a selective inhibitor of a membrane-bound α-glucosidase. The term "selective inhibitor of a membrane-bound α-glucosidase" is used herein to mean an agent which selectively inhibits a membrane-bound α-glucosidase activity in preference to an ER-α-glucosidase (or any other enzyme) and particularly a compound for which the ratio of the $IC_{50}$ concentration (concentration inhibiting 50% of activity) for a membrane-bound α-glucosidase to the $IC_{50}$ concentration for an ER-α-glucosidase is greater than 1. Such ratio is readily determined by assaying for the effect of the inhibitor on a membrane-bound α-glucosidase activity and assaying for the effect of the inhibitor an ER-α-glucosidase and from the resulting data obtaining a ratio of $IC_{50}$s.

Of particular interest in some embodiments of a subject monotherapy is use of an agent that inhibits enzymatic activity of a membrane-bound α-glucosidase with an IC50 of less than about 50 µM, e.g., a suitable agent inhibits enzymatic activity of a membrane-bound α-glucosidase with an IC50 of less than about 40 µM, less than about 25 µM, less than about 10 µM, less than about 1 µM, less than about 100 nM, less than about 80 nM, less than about 60 nM, less than about 50 nM, less than about 25 nM, less than about 10 nM, or less than about 1 nM, or less.

In many embodiments, an agent that inhibits enzymatic activity of a membrane-bound α-glucosidase inhibits viral replication. For example, an agent that inhibits enzymatic activity of a membrane-bound α-glucosidase inhibits viral replication by at least about 10%, at least about 15%, at least about 20%, at least about 25%, at least about 30%, at least about 40%, at least about 50%, at least about 60%, at least about 70%, at least about 80%, or at least about 90%, or more, compared to viral replication in the absence of the compound. Whether a compound inhibits viral replication can be determined using methods known in the art, including an in vitro viral replication assay.

In some embodiments, the agent is an imino sugar. In some embodiments, the agent is miglitol (3,4,5-piperidinetriol, 1-(2-hydroxyethyl)-2-(hydroxymethyl)-, [2R-(2α,3β,4α,5β)]) or Glyset® (miglitol; N-hydroxyethyl-DNJ). Miglitol (N-hydroxyethyl-DNJ) is described in U.S. Pat. No. 4,639,436. Miglitol has the structure shown in Formula I:

Formula I

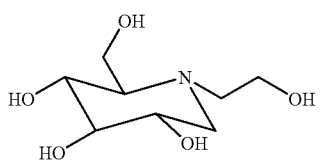

In some embodiments, the agent is acarbose (O-4,6-dideoxy-4-[[(1S,4R,5S,6S)-4,5,6-trihydroxy-3-(hydroxymethyl)-2-cyclohexen-1-yl]amino]-α-D-glucopyranosyl-(1→4)-O-α-D-glucopyranosyl-(1→4)-D-glucose), or Precose®. Acarbose is described in U.S. Pat. No. 4,904,769. In some embodiments, acarbose is a highly purified form of acarbose (see, e.g., U.S. Pat. No. 4,904,769). Acarbose has the structure shown in Formula II:

Formula II

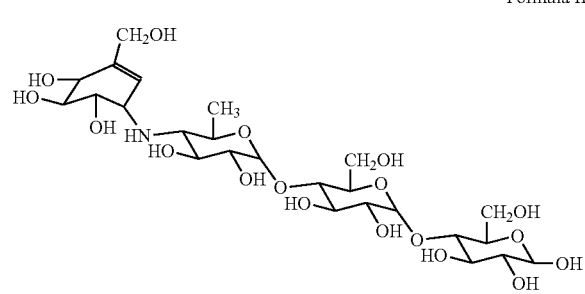

Hepatitis Virus Infection

The present invention provides monotherapy methods of treating a hepatitis virus infection. In particular embodiments, the present invention provides methods of treating a hepatitis C virus (HCV) infection; methods of reducing the incidence of complications associated with HCV and cirrhosis of the liver; and methods of reducing viral load, or reducing the time to viral clearance, or reducing morbidity or mortality in the clinical outcomes, in patients suffering from HCV infection. The methods generally involve administering to the individual an effective amount of an agent that inhibits enzymatic activity of a membrane-bound α-glucosidase in monotherapy. Effective amounts of an agent that inhibits enzymatic activity of a membrane-bound α-glucosidase, as well as dosing regimens, are discussed below.

In many embodiments, a subject monotherapy treatment method is effective to decrease viral load in the individual, and to achieve a sustained viral response. Of particular interest in many embodiments is treatment of humans.

Whether a subject monotherapy method is effective in treating an HCV infection can be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR (RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) Ann. Intern. Med. 123:321-329. Also of interest is a nucleic acid test (NAT), developed by Gen-Probe Inc. (San Diego) and Chiron Corporation, and sold by Chiron Corporation under the trade name Procleix®, which NAT simultaneously tests for the presence of HIV-1 and HCV. See, e.g., Vargo et al. (2002) Transfusion 42:876-885.

In some embodiments, an effective amount of an agent that inhibits enzymatic activity of a membrane-bound α-glucosidase is an amount that, in monotherapy, is effective to reduce HCV viral load to undetectable levels, e.g., to less than about 5000, less than about 1000, less than about 500, or less than about 200 genome copies/mL serum. In some embodiments, an effective amount of an agent that inhibits enzymatic activity of a membrane-bound α-glucosidase is an amount that, in monotherapy, is effective to reduce HCV viral load to less than 100 genome copies/mL serum.

In other embodiments, an effective amount of an agent that inhibits enzymatic activity of a membrane-bound α-glucosidase is an amount that, in monotherapy, is effective to achieve a 1.5-log, a 2-log, a 2.5-log, a 3-log, a 3.5-log, a 4-log, a 4.5-log, or a 5-log reduction in HCV viral titer in the serum of the individual.

In many embodiments, the methods of the invention achieve a sustained viral response, e.g., the viral load is reduced to undetectable levels for a period of at least about one month, at least about two months, at least about three months, at least about four months, at least about five months, or at least about six months following cessation of treatment.

Whether a subject method is effective in treating an HCV infection can be determined by measuring a parameter associated with HCV infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a an agent that inhibits enzymatic activity of a membrane-bound α-glucosidase that is administered in a subject monotherapy is an amount effective to reduce ALT levels to less than about 45 U/ml serum.

In other embodiments, a therapeutically effective amount of an agent that inhibits enzymatic activity of a membrane-bound α-glucosidase is an amount that, in monotherapy, is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

West Nile Virus

The present invention provides monotherapy methods for treating West Nile viral infection. The methods generally involve administering to an individual an agent that inhibits enzymatic activity of a membrane-bound α-glucosidase in an amount that is effective to reduce the time to viral clearance in the individual, and/or to ameliorate the clinical course of the disease. Effective amounts of an agent that inhibits enzymatic activity of a membrane-bound α-glucosidase, as well as dosing regimens, are discussed below.

Whether a subject method is effective in treating a West Nile viral infection can be determined by a reduction in number or length of hospital stays, a reduction in time to viral clearance, a reduction of morbidity or mortality in clinical outcomes, or other indicator of disease response.

In some embodiments, an effective amount of an agent that inhibits enzymatic activity of a membrane-bound α-glucosidase is an amount that, in monotherapy, is effective to reduce the time to viral clearance, or an amount that is effective to reduce morbidity or mortality in the clinical course of the disease.

Liver Fibrosis

The instant invention provides monotherapy methods for treating liver fibrosis (including forms of liver fibrosis resulting from, or associated with, HCV infection), generally involving administering a therapeutic amount of an agent that inhibits enzymatic activity of a membrane-bound α-glucosidase. Effective amounts of an agent that inhibits enzymatic activity of a membrane-bound α-glucosidase, as well as dosing regimens, are discussed below.

Whether treatment with an agent that inhibits enzymatic activity of a membrane-bound α-glucosidase is effective in reducing liver fibrosis can be determined by any of a number of well-established techniques for measuring liver fibrosis and liver function. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are. as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a subject therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, an effective amount of an agent that inhibits enzymatic activity of a membrane-bound α-glucosidase is an amount of an agent that inhibits enzymatic activity of a membrane-bound α-glucosidase and that effects a change of one unit or more in the fibrosis stage based on pre- and post-therapy liver biopsies. In particular embodiments, a therapeutically effective amount of an agent that inhibits enzymatic activity of a membrane-bound α-glucosidase reduces liver fibrosis by at least one unit in the METAVIR, the Knodell, the Scheuer, the Ludwig, or the Ishak scoring system.

Secondary, or indirect, indices of liver function can also be used to evaluate the efficacy of a subject treatment. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

In other embodiments, an effective amount of an agent that inhibits enzymatic activity of a membrane-bound α-glucosidase is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

In other embodiments, a therapeutically effective amount of an agent that inhibits enzymatic activity of a membrane-bound α-glucosidase is an amount that, in monotherapy, is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment with an agent that inhibits enzymatic acitivty of a membrane-bound α-glucosidase. These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

In other embodiments, a therapeutically effective amount of an agent that inhibits enzymatic activity of a membrane-bound α-glucosidase is an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with an agent that inhibits enzymatic activity of a membrane-bound α-glucosidase is effective in reducing the incidence of a disorder associated with cirrhosis of the liver can readily be determined by those skilled in the art.

Reduction in liver fibrosis increases liver function. Thus, the invention provides methods for increasing liver function, generally involving administering a therapeutically effective amount of an agent that inhibits enzymatic activity of a membrane-bound α-glucosidase. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal level of alanine transaminase is about 45 IU per milliliter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

In some embodiments, a therapeutically effective amount of an agent that inhibits enzymatic activity of a membrane-bound α-glucosidase is one that is effective to increase liver function by at least about 10%, at least about 20%, at least about 30%, at least about 40%, at least about 50%, at least about 60%, at least about 70%, at least about 80%, or more. In other embodiments, a therapeutically effective amount of an agent that inhibits enzymatic activity of a membrane-bound α-glucosidase is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. In other embodiments, a therapeutically effective amount of an agent that inhibits enzymatic activity of a membrane-bound α-glucosidase is an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Combination Therapy

The present invention further provides combination therapies. Thus, the present invention provides methods for treating alphavirus infections; methods of treating flavivirus infections; methods of treating HCV infections; methods of treating WNV infection; methods of reducing liver fibrosis;

methods of increasing liver function in an individual suffering from liver fibrosis; methods of reducing the incidence of complications associated with HCV and cirrhosis of the liver; and methods of reducing viral load, or reducing the time to viral clearance, or reducing morbidity or mortality in the clinical outcomes, in patients suffering from flavivirus infection. The methods generally involve administering to an individual in need thereof an effective amount of an agent that inhibits enzymatic activity of an α-glucosidase, in combination with at least a second therapeutic agent. In some embodiments, the effective amounts of the α-glucosidase inhibitor and the at least one additional therapeutic agent are synergistic amounts.

Suitable second therapeutic agents for treating an alphavirus infection include, but are not limited to, a Type I interferon receptor agonist, a Type II interferon receptor agonist; a Type III interferon receptor agonist; a nucleoside analog (e.g., ribavirin, levovirin, or viramidine); an NS3 protease inhibitor, and NS3 helicase inhibitor, an NS5B inhibitor, and thymosin-α.

A subject combination therapy involves administering effective amounts of an α-glucosidase inhibitor and at least a second therapeutic agent. In some embodiments, effective amounts of an α-glucosidase inhibitor and at least a second therapeutic agent are amounts that, in combination therapy, are effective to reduce viral titers to undetectable levels, e.g., to about 1000 to about 5000, to about 500 to about 1000, or to about 100 to about 500 genome copies/mL serum. In some embodiments, effective amounts of an α-glucosidase inhibitor and at least a second therapeutic agent are amounts that, in combination therapy, are effective to reduce viral load to lower than 100 genome copies/mL serum.

In some embodiments, effective amounts of an α-glucosidase inhibitor and at least a second therapeutic agent are amounts that, in combination therapy, are effective to achieve a 1.5-log, a 2-log, a 2.5-log, a 3-log, a 3.5-log, a 4-log, a 4.5-log, or a 5-log reduction in viral titer in the serum of the individual.

In some embodiments, effective amounts of an α-glucosidase inhibitor and at least a second therapeutic agent are amounts that, in combination therapy, are synergistic amounts. In some of these embodiments, the amount of the at least one second therapeutic agent that is required to be administered to the individual to achieve a desired therapeutic effect (e.g., reduction in serum viral load) is reduced, compared to the dose that is normally required to be administered to achieve the same effect (e.g., the same reduction in serum viral load), when the at least one additional second therapeutic agent is administered in monotherapy or in the absence of co-administration with an α-glucosidase inhibitor. As one non-limiting example, a reduction in HCV serum viral load can be achieved using a combination of α-glucosidase inhibitor and consensus IFN-α (CIFN), where the amount of CIFN in the combination therapy that is required to achieve the reduction in the serum HCV viral load is lower than the amount of CIFN that would be required to achieve the same reduction in HCV serum viral load were the CIFN administered in monotherapy. In some of these α-glucosidase inhibitor/second therapeutic agent combination therapy embodiments, the amount of the α-glucosidase inhibitor that is required to be administered to the individual to achieve a desired therapeutic effect (e.g., reduction in serum viral load) is reduced, compared to the dose that is normally required to be administered to achieve the same effect (e.g., the same reduction in serum viral load), when the α-glucosidase inhibitor is administered in monotherapy. In some of these α-glucosidase inhibitor/second therapeutic agent combination therapy embodiments, the amount of the α-glucosidase inhibitor and the amount of the second therapeutic agent that are required to be administered to the individual to achieve a desired therapeutic effect (e.g., reduction in serum viral load) are reduced, compared to the doses that are required to achieve the same effect (e.g., the same reduction in serum viral load) in monotherapy, e.g., when the α-glucosidase inhibitor is administered in monotherapy, and when the second therapeutic agent is administered in monotherapy.

Hepatitis Virus Infection

The present invention provides combination therapy methods of treating a hepatitis virus infection. In particular embodiments, the present invention provides methods of treating a hepatitis C virus (HCV) infection; methods of reducing the incidence of complications associated with HCV and cirrhosis of the liver; and methods of reducing viral load, or reducing the time to viral clearance, or reducing morbidity or mortality in the clinical outcomes, in patients suffering from HCV infection. The methods generally involve administering to the individual combined effective amounts of an α-glucosidase inhibitor and at least a second therapeutic agent. Combined effective amounts of an α-glucosidase inhibitor and at least a second therapeutic agent, as well as dosing regimens, are discussed below.

In many embodiments, a subject combination treatment method is effective to decrease viral load in the individual, and to achieve a sustained viral response. Of particular interest in many embodiments is treatment of humans.

Whether a subject combination method is effective in treating an HCV infection can be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR (RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) Ann. Intern. Med. 123:321-329. Also of interest is a nucleic acid test (NAT), developed by Gen-Probe Inc. (San Diego) and Chiron Corporation, and sold by Chiron Corporation under the trade name Procleix®, which NAT simultaneously tests for the presence of HIV-1 and HCV. See, e.g., Vargo et al. (2002) Transfusion 42:876-885.

In some embodiments, effective amounts of an α-glucosidase inhibitor and at least a second therapeutic agent are amounts that, in combination therapy, are effective to reduce HCV viral load to undetectable levels, e.g., to less than about 5000, less than about 1000, less than about 500, or less than about 200 genome copies/mL serum. In some embodiments, effective amounts of an α-glucosidase inhibitor and at least a second therapeutic agent are amounts that, in combination therapy, are effective to reduce HCV viral load to less than 100 genome copies/mL serum.

In other embodiments, effective amounts of an α-glucosidase inhibitor and at least a second therapeutic agent are amounts that, in combination therapy, are effective to achieve a 1.5-log, a 2-log, a 2.5-log, a 3-log, a 3.5-log, a 4-log, a 4.5-log, or a 5-log reduction in HCV viral titer in the serum of the individual.

In many embodiments, the methods of the invention achieve a sustained viral response, e.g., the viral load is reduced to undetectable levels for a period of at least about one month, at least about two months, at least about three months, at least about four months, at least about five months, or at least about six months following cessation of treatment.

Whether a subject method is effective in treating an HCV infection can be determined by measuring a parameter associated with HCV infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a therapeutic agent that is administered as part of a subject combination therapy is an amount effective to reduce ALT levels to less than about 45 U/ml serum.

In other embodiments, effective amounts of an α-glucosidase inhibitor and at least a second therapeutic agent are amounts that, in combination therapy, are effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

West Nile Virus

The present invention provides combination therapy methods for treating West Nile viral infection. The methods generally involve administering to an individual an αa-glucosidase inhibitor and at least a second therapeutic agent in amounts that in amounts that in combination therapy are effective to reduce the time to viral clearance in the individual, and/or to ameliorate the clinical course of the disease. Effective amounts of an α-glucosidase inhibitor and at least a second therapeutic agent, as well as dosing regimens, are discussed below.

Whether a subject method is effective in treating a West Nile viral infections can be determined by a reduction in number or length of hospital stays, a reduction in time to viral clearance, a reduction of morbidity or mortality in clinical outcomes, or other indicator of disease response.

In some embodiments, effective amounts of an α-glucosidase inhibitor and at least a second therapeutic agent are amounts that, in combination therapy, are effective to reduce the time to viral clearance, or an amount that is effective to reduce morbidity or mortality in the clinical course of the disease.

Liver Fibrosis

The instant invention provides combination therapy methods for treating liver fibrosis (including forms of liver fibrosis resulting from, or associated with, HCV infection), generally involving administering effective amounts of an α-glucosidase inhibitor and at least a second therapeutic agent. Effective amounts of an α-glucosidase inhibitor and at least a second therapeutic agent, as well as dosing regimens, are discussed below.

Whether a subject combination therapy is effective in reducing liver fibrosis can be determined by any of a number of well-established techniques for measuring liver fibrosis and liver function. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a subject combination therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, effective amounts of an α-glucosidase inhibitor and at least a second therapeutic agent are amounts that, in combination therapy, are amounts that effect a change of one unit or more in the fibrosis stage based on pre- and post-therapy liver biopsies. In particular embodiments, therapeutically effective amounts of an α-glucosidase inhibitor and at least a second therapeutic agent are amounts that, in combination therapy, reduce liver fibrosis by at least one unit in the METAVIR, the Knodell, the Scheuer, the Ludwig, or the Ishak scoring system.

Secondary, or indirect, indices of liver function can also be used to evaluate the efficacy of a subject treatment. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

In other embodiments, effective amounts of an α-glucosidase inhibitor and at least a second therapeutic agent are amounts that, in combination therapy, are effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include α-2-macroglobulin, haptoglobin, gamma globulin, apolipoprotein A, and gamma glutamyl transpeptidase.

In other embodiments, effective amounts of an α-glucosidase inhibitor and at least a second therapeutic agent are amounts that, in combination therapy, are effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment with an agent that inhibits enzymatic acitivty of a membrane-bound α-glucosidase. These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

In other embodiments, effective amounts of an α-glucosidase inhibitor and at least a second therapeutic agent are amounts that, in combination therapy, are effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with an agent that inhibits enzymatic activity of a membrane-bound α-glucosidase is effective in reducing the incidence of a disorder associated with cirrhosis of the liver can readily be determined by those skilled in the art.

Reduction in liver fibrosis increases liver function. Thus, the invention provides methods for increasing liver function, generally involving administering a therapeutically effective amount of an agent that inhibits enzymatic activity of a membrane-bound α-glucosidase. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Those skilled in the art know the normal ranges for such serum proteins. The following are non-limiting examples. The normal level of alanine transaminase is about 45 IU per milliliter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

In some embodiments, effective amounts of an α-glucosidase inhibitor and at least a second therapeutic agent are amounts that, in combination therapy, are effective to increase liver function by at least about 10%, at least about 20%, at least about 30%, at least about 40%, at least about 50%, at least about 60%, at least about 70%, at least about 80%, or more. In other embodiments, effective amounts of an α-glucosidase inhibitor and at least a second therapeutic agent are amounts that, in combination therapy, are effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. In other embodiments, effective amounts of an α-glucosidase inhibitor and at least a second therapeutic agent are amounts that, in combination therapy, are effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Alpha-glucosidase Inhibitors

Alpha-glucosidase inhibitors suitable for use in a subject combination therapy include any imino-sugar, including long-alkyl chain derivatives of imino sugars as disclosed in U.S. Patent Publication No. 2004/0110795; inhibitors of endoplasmic reticulum-associated α-glucosidases; inhibitors of membrane bound α-glucosidase; miglitol (Glyset®), and active derivatives, and analogs thereof; and acarbose (Precose®), and active derivative, and analogs thereof. Suitable agents include long-alkyl-chain imino sugar derivatives that inhibit the HCV protein p7. See, e.g., Pavlovic et al. (2003) Proc. Natl. Acad. Sci. USA 100:6104-6108; and U.S. Patent Publication No. 2004/0110795. Suitable agents include, but are not limited to, deoxynojirimycin (DNJ), deoxygalactojirimycin (DGJ), N-butyl-deoxynojirimycin (NB-DNJ), N-nonyl-deoxynojirimycin (NN-DNJ), N-butyl-deoxygalactojirimycin (NB-DGJ), N-nonyl-deoxygalactojirimycin (NN-DGJ), NN-6deoxy-DGJ, N7-oxadecyl-DNJ, N7-oxanony-6deoxy-DGJ, perbutylated-N-butyl-1-deoxynojirimycin (p-N-butyl-DNJ), and 6-O-butanoyl castanospermine.

Type I Interferon Receptor Agonists

In some embodiments, a subject method involves administration of effective amounts of an α-glucosidase inhibitor; and Type I interferon receptor agonist. Type I interferon receptor agonists include an IFN-α; an IFN-β; an IFN-tau; an IFN-ω; antibody agonists specific for a Type I interferon receptor; and any other agonist of Type I interferon receptor, including non-polypeptide agonists.

Interferon-Alpha

Any known IFN-α can be used in the instant invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α2α, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon Tradename.

The term "IFN-α" also encompasses consensus IFN-α. Consensus IFN-α (also referred to as "CIFN" and "IFN-con" and "consensus interferon") encompasses but is not limited to the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. Use of CIFN is of particular interest.

Also suitable for use in the present invention are fusion polypeptides comprising an IFN-α and a heterologous polypeptide. Suitable IFN-α fusion polypeptides include, but are not limited to, Albuferon-alpha™ (a fusion product of human albumin and IFN-α; Human Genome Sciences; see, e.g., Osborn et al. (2002) J. Pharmacol. Exp. Therap. 303: 540-548). Also suitable for use in the present invention are gene-shuffled forms of IFN-α. See., e.g., Masci et al. (2003) Curr. Oncol. Rep. 5:108-113.

PEGylated Interferon-Alpha

The term "IFN-α" also encompasses derivatives of IFN-α that are derivatized (e.g., are chemically modified) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

Any of the above-mentioned IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In some embodiments, the PEGylated IFN-α contains a PEG moiety on only one amino acid. In other embodiments, the PEGylated IFN-α contains a PEG moiety on two or more amino acids, e.g., the IFN-α contains a PEG moiety attached to two, three, four, five, six, seven, eight, nine, or ten different amino acid residues.

IFN-α may be coupled directly to PEG (i.e., without a linking group) through an amino group, a sulfhydryl group, a hydroxyl group, or a carboxyl group.

In some embodiments, the PEGylated IFN-α is PEGylated at or near the amino terminus (N-terminus) of the IFN-α polypeptide, e.g., the PEG moiety is conjugated to the IFN-α polypeptide at one or more amino acid residues from amino acid 1 through amino acid 4, or from amino acid 5 through about 10.

In other embodiments, the PEGylated IFN-α is PEGylated at one or more amino acid residues from about 10 to about 28.

In other embodiments, the PEGylated IFN-α is PEGylated at or near the carboxyl terminus (C-terminus) of the IFN-α polypeptide, e.g., at one or more residues from amino acids 156-166, or from amino acids 150 to 155.

In other embodiments, the PEGylated IFN-α is PEGylated at one or more amino acid residues at one or more residues from amino acids 100-114.

The polyethylene glycol derivatization of amino acid residues at or near the receptor-binding and/or active site domains of the IFN-α protein can disrupt the functioning of these domains. In certain embodiments of the invention, amino acids at which PEGylation is to be avoided include amino acid residues from amino acid 30 to amino acid 40; and amino acid residues from amino acid 113 to amino acid 149.

In some embodiments, PEG is attached to IFN-α via a linking group. The linking group is any biocompatible linking group, where "biocompatible" indicates that the compound or group is non-toxic and may be utilized in vitro or in vivo without causing injury, sickness, disease, or death. PEG can be bonded to the linking group, for example, via an ether bond, an ester bond, a thiol bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoate (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

Methods for making succinimidyl propionate (SPA) and succinimidyl butanoate (SBA) ester-activated PEGs are described in U.S. Pat. No. 5,672,662 (Harris, et al.) and WO 97/03106.

Methods for attaching a PEG to an IFN-α polypeptide are known in the art, and any known method can be used. See, for example, by Park et al, Anticancer Res., 1:373-376 (1981); Zaplipsky and Lee, Polyethylene Glycol Chemistry: Biotechnical and Biomedical Applications, J. M. Harris, ed., Plenum Press, NY, Chapter 21 (1992); U.S. Pat. No. 5,985,265; U.S. Pat. No. 5,672,662 (Harris, et al.) and WO 97/03106.

Pegylated IFN-α, and methods for making same, is discussed in, e.g., U.S. Pat. Nos. 5,382,657; 5,981,709; 5,985,265; and 5,951,974. Pegylated IFN-α encompasses conjugates of PEG and any of the above-described IFN-α molecules, including, but not limited to, PEG conjugated to interferon alpha-2a (Roferon, Hoffman LaRoche, Nutley, N.J.), where PEGylated Roferon is known as Pegasys (Hoffman LaRoche); interferon alpha 2b (Intron, Schering-Plough, Madison, N.J.), where PEGylated Intron is known as PEG-Intron (Schering-Plough); interferon alpha-2c (Berofor Alpha, Boehringer Ingelheim, Ingelheim, Germany); and consensus interferon (CIFN) as defined by determination of a consensus sequence of naturally occurring interferon alphas (Infergen®, InterMune, Inc., Brisbane, Calif.), where PEGylated CIFN is referred to as PEG-CIFN.

In many embodiments, the PEG is a monomethoxyPEG molecule that reacts with primary amine groups on the IFN-α polypeptide. Methods of modifying polypeptides with monomethoxy PEG via reductive alkylation are known in the art. See, e.g., Chamow et al. (1994) Bioconj. Chem. 5:133-140.

In one non-limiting example, PEG is linked to IFN-α via an SPA linking group. SPA esters of PEG, and methods for making same, are described in U.S. Pat. No. 5,672,662. SPA linkages provide for linkage to free amine groups on the IFN-α polypeptide.

For example, a PEG molecule is covalently attached via a linkage that comprises an amide bond between a propionyl group of the PEG moiety and the epsilon amino group of a surface-exposed lysine residue in the IFN-α polypeptide. Such a bond can be formed, e.g., by condensation of an α-methoxy, omega propanoic acid activated ester of PEG (mPEGspa).

In some embodiments, the invention employs a PEG-modified CIFN, where the PEG moiety is attached to a lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$. In these embodiments, the PEG moiety can be a linear PEG moiety having an average molecular weight of about 30 kD.

In other embodiments, the invention employs a PEG-modified CIFN, where the PEG moiety is attached to a lysine residue chosen from $lys^{121}$, $lys^{134}$, $lys^{135}$, and $lys^{165}$. In these embodiments, the PEG moiety can be a linear PEG moiety having an average molecular weight of about 30 kD.

As one non-limiting example, one monopegylated CIFN conjugate preferred for use herein has a linear PEG moiety of about 30 kD attached via a covalent linkage to the CIFN polypeptide, where the covalent linkage is an amide bond between a propionyl group of the PEG moiety and the epsilon amino group of a surface-exposed lysine residue in the CIFN polypeptide, where the surface-exposed lysine residue is chosen from $lys^{31}$, $lys^{50}$, $lys^{71}$, $lys^{84}$, $lys^{121}$, $lys^{122}$, $lys^{134}$, $lys^{135}$, and $lys^{165}$, and the amide bond is formed by condensation of an α-methoxy, omega propanoic acid activated ester of PEG.

Linking Groups

In some embodiments, PEG is attached to IFN-α via a linking group. The linking group is any biocompatible linking group, where "biocompatible" indicates that the compound or group is essentially non-toxic and may be utilized in vivo without causing a significant adverse response in the subject, e.g., injury, sickness, disease, undesirable immune response, or death. PEG can be bonded to the linking group, for example, via an ether bond, an ester bond, a thio ether bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoic acid (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

In many embodiments, the PEG is a monomethoxyPEG molecule that reacts with primary amine groups on the IFN-α polypeptide. Methods of modifying polypeptides with monomethoxy PEG via reductive alkylation are known in the art. See, e.g., Chamow et al. (1994) *Bioconj. Chem.* 5:133-140.

In one non-limiting example, PEG is linked to IFN-α via an SPA linking group. SPA esters of PEG, and methods for making same, are described in U.S. Pat. No. 5,672,662. SPA linkages provide for linkage to free amine groups on the IFN-α polypeptide.

For example, a PEG molecule is covalently attached via a linkage that comprises an amide bond between a propionyl group of the PEG moiety and the epsilon amino group of a surface-exposed lysine residue in the IFN-α polypeptide. Such a bond can be formed, e.g., by condensation of an α-methoxy, omega propanoic acid activated ester of PEG (mPEGspa).

As one non-limiting example, monopegylated CIFN has a linear PEG moiety of about 30 kD attached via a covalent linkage to the CIFN polypeptide, where the covalent linkage is an amide bond between a propionyl group of the PEG moiety and the epsilon amino group of a surface-exposed lysine residue in the CIFN polypeptide, where the surface-exposed lysine residue is chosen from $lys^{121}$, $lys^{134}$, $lys^{135}$, and $lys^{165}$, and the amide bond is formed by condensation of an α-methoxy, omega propanoic acid activated ester of PEG.

Methods for attaching a PEG molecule to an IFN-α polypeptide are known in the art, and any known method can be used. See, for example, by Park et al, *Anticancer Res.*, 1:373-376 (1981); Zaplipsky and Lee, Polyethylene Glycol Chemistry: Biotechnical and Biomedical Applications, J. M. Harris, ed., Plenum Press, NY, Chapter 21 (1992); and U.S. Pat. No. 5,985,265.

Polyethylene Glycol

Polyethylene glycol suitable for conjugation to an IFN-α polypeptide is soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

In many embodiments, PEG has at least one hydroxyl group, e.g., a terminal hydroxyl group, which hydroxyl group is modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

In other embodiments, PEG is derivatized so that it is reactive with free carboxyl groups in the IFN-α polypeptide, e.g., the free carboxyl group at the carboxyl terminus of the IFN-α polypeptide. Suitable derivatives of PEG that are reactive with the free carboxyl group at the carboxyl-terminus of IFN-α include, but are not limited to PEG-amine, and hydrazine derivatives of PEG (e.g., PEG-NH—NH$_2$).

In other embodiments, PEG is derivatized such that it comprises a terminal thiocarboxylic acid group, —COSH, which selectively reacts with amino groups to generate amide derivatives. Because of the reactive nature of the thio acid, selectivity of certain amino groups over others is achieved. For example, —SH exhibits sufficient leaving group ability in reaction with N-terminal amino group at appropriate pH conditions such that the ε-amino groups in lysine residues are protonated and remain non-nucleophilic. On the other hand, reactions under suitable pH conditions may make some of the accessible lysine residues to react with selectivity.

In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5. For example, the N-terminal amino groups may be selectively modified under neutral pH conditions. However, if the reactivity of the reagent were extreme, accessible-NH$_2$ groups of lysine may also react.

The PEG can be conjugated directly to the IFN-α polypeptide, or through a linker. In some embodiments, a linker is added to the IFN-α polypeptide, forming a linker-modified IFN-α polypeptide. Such linkers provide various functionalities, e.g., reactive groups such sulfhydryl, amino, or carboxyl groups to couple a PEG reagent to the linker-modified IFN-α polypeptide.

In some embodiments, the PEG conjugated to the IFN-α polypeptide is linear. In other embodiments, the PEG conjugated to the IFN-α polypeptide is branched. Branched PEG derivatives such as those described in U.S. Pat. No. 5,643,575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

PEG having a molecular weight in a range of from about 2 kDa to about 100 kDa, is generally used, where the term "about," in the context of PEG, indicates that in preparations of polyethylene glycol, some molecules will weigh more, some less, than the stated molecular weight. For example, PEG suitable for conjugation to IFN-α has a molecular weight of from about 2 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 40 kDa, from about 40 kDa to about 50 kDa, from about 50 kDa to about 60 kDa, from about 60 kDa to about 70 kDa, from about 70 kDa to about 80 kDa, from about 80 kDa to about 90 kDa, or from about 90 kDa to about 100 kDa.

Preparing PEG-IFN-α Conjugates

As discussed above, the PEG moiety can be attached, directly or via a linker, to an amino acid residue at or near the N-terminus, internally, or at or near the C-terminus of the IFN-α polypeptide. Conjugation can be carried out in solution or in the solid phase.

N-terminal Linkage

Methods for attaching a PEG moiety to an amino acid residue at or near the N-terminus of an IFN-α polypeptide are known in the art. See, e.g., U.S. Pat. No. 5,985,265.

In some embodiments, known methods for selectively obtaining an N-terminally chemically modified IFN-α are used. For example, a method of protein modification by reductive alkylation which exploits differential reactivity of different types of primary amino groups (lysine versus the N-terminus) available for derivatization in a particular protein can be used. Under the appropriate reaction conditions, substantially selective derivatization of the protein at the N-terminus with a carbonyl group containing polymer is achieved. The reaction is performed at pH which allows one to take advantage of the $pK_a$ differences between the ε-amino groups of the lysine residues and that of the α-amino group of the N-terminal residue of the protein. By such selective derivatization attachment of a PEG moiety to the IFN-α is controlled: the conjugation with the polymer takes place predominantly at the N-terminus of the IFN-α and no significant modification of other reactive groups, such as the lysine side chain amino groups, occurs.

C-terminal Linkage

N-terminal-specific coupling procedures such as described in U.S. Pat. No. 5,985,265 provide predominantly monoPEGylated products. However, the purification procedures aimed at removing the excess reagents and minor multiply PEGylated products remove the N-terminal blocked polypeptides. In terms of therapy, such processes lead to significant increases in manufacturing costs. For example, examination of the structure of the well-characterized Infergen® Alfacon-1 CIFN polypeptide amino acid sequence reveals that the clipping is approximate 5% at the carboxyl terminus and thus there is only one major C-terminal sequence. Thus, in some embodiments, N-terminally PEGylated IFN-α is not used; instead, the IFN-α polypeptide is C-terminally PEGylated.

An effective synthetic as well as therapeutic approach to obtain mono PEGylated Infergen product is therefore envisioned as follows:

A PEG reagent that is selective for the C-terminal can be prepared with or without spacers. For example, polyethylene glycol modified as methyl ether at one end and having an amino function at the other end may be used as the starting material.

Preparing or obtaining a water-soluble carbodiimide as the condensing agent can be carried out. Coupling IFN-α (e.g., Infergen® Alfacon-1 CIFN or consensus interferon) with a water-soluble carbodiimide as the condensing reagent is generally carried out in aqueous medium with a suitable buffer system at an optimal pH to effect the amide linkage. A high molecular weight PEG can be added to the protein covalently to increase the molecular weight.

The reagents selected will depend on process optimization studies. A non-limiting example of a suitable reagent is EDAC or 1-ethyl-3-(3-dimethylaminopropyl) carbodiimide. The water solubility of EDAC allows for direct addition to a reaction without the need for prior organic solvent dissolution. Excess reagent and the isourea formed as the by-product of the cross-linking reaction are both water-soluble and may easily be removed by dialysis or gel filtration. A concentrated solution of EDAC in water is prepared to facilitate the addition of a small molar amount to the reaction. The stock solution is prepared and used immediately in view of the water labile nature of the reagent. Most of the synthetic protocols in literature suggest the optimal reaction medium to be in pH range between 4.7 and 6.0. However the condensation reactions do proceed without significant losses in yields up to pH 7.5. Water may be used as solvent. In view of the contemplated use of Infergen, preferably the medium will be 2-(N-morpholino)ethane sulfonic acid buffer pre-titrated to pH between 4.7 and 6.0. However, 0.1M phosphate in the pH 7-7.5 may also be used in view of the fact that the product is in the same buffer. The ratios of PEG amine to the IFN-α molecule is optimized such that the C-terminal carboxyl residue(s) are selectively PEGylated to yield monoPEGylated derivative(s).

Even though the use of PEG amine has been mentioned above by name or structure, such derivatives are meant to be exemplary only, and other groups such as hydrazine derivatives as in PEG-NH—$NH_2$ which will also condense with the carboxyl group of the IFN-α protein, can also be used. In addition to aqueous phase, the reactions can also be conducted on solid phase. Polyethylene glycol can be selected from list of compounds of molecular weight ranging from 300-40000. The choice of the various polyethylene glycols will also be dictated by the coupling efficiency and the biological performance of the purified derivative in vitro and in vivo i.e., circulation times, anti viral activities etc.

Additionally, suitable spacers can be added to the C-terminal of the protein. The spacers may have reactive groups such as SH, $NH_2$ or COOH to couple with appropriate PEG reagent to provide the high molecular weight IFN-α derivatives. A combined solid/solution phase methodology can be devised for the preparation of C-terminal pegylated interferons. For example, the C-terminus of IFN-α is extended on a solid phase using a Gly-Gly-Cys-$NH_2$ spacer and then monopegylated in solution using activated dithiopyridyl-PEG reagent of appropriate molecular weights. Since the coupling at the C-terminus is independent of the blocking at the N-terminus, the envisioned processes and products will be beneficial with respect to cost (a third of the protein is not wasted as in N-terminal PEGylation methods) and contribute to the economy of the therapy to treat chronic hepatitis C infections, liver fibrosis etc.

There may be a more reactive carboxyl group of amino acid residues elsewhere in the molecule to react with the PEG reagent and lead to monoPEGylation at that site or lead to multiple PEGylations in addition to the —COOH group at the C-terminus of the IFN-α. It is envisioned that these reactions will be minimal at best owing to the steric freedom at the C-terminal end of the molecule and the steric hindrance imposed by the carbodiimides and the PEG reagents such as in branched chain molecules. It is therefore the preferred mode of PEG modification for Infergen and similar such proteins, native or expressed in a host system, which may have blocked N-termini to varying degrees to improve efficiencies and maintain higher in vivo biological activity.

Another method of achieving C-terminal PEGylation is as follows. Selectivity of C-terminal PEGylation is achieved with a sterically hindered reagent which excludes reactions at carboxyl residues either buried in the helices or internally in IFN-α. For example, one such reagent could be a branched chain PEG ~40 kd in molecular weight and this agent could be synthesized as follows:

$OH_3C$—$(CH_2CH_2O)n$-$CH_2CH_2NH_2$+Glutamic Acid i.e., HOCO—$CH_2CH_2CH(NH2)$-COOH is condensed with a suitable agent e.g., dicyclohexyl carbodiimide or water-soluble EDAC to provide the branched chain PEG agent $OH_3C$—$(CH_2CH_2O)_n$—$CH_2CH_2NHCOCH(NH_2)$ $CH_2OCH_3$—$(CH_2CH_2O)_n$—$CH_2CH_2NHCOCH_2$.

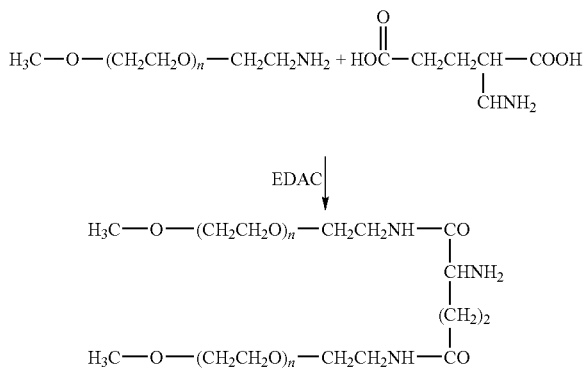

This reagent can be used in excess to couple the amino group with the free and flexible carboxyl group of IFN-α to form the peptide bond.

If desired, PEGylated IFN-α is separated from unPEGylated IFN-α using any known method, including, but not limited to, ion exchange chromatography, size exclusion chromatography, and combinations thereof. For example, where the PEG-IFN-α conjugate is a monoPEGylated IFN-α, the products are first separated by ion exchange chromatography to obtain material having a charge characteristic of monoPEGylated material (other multi-PEGylated material having the same apparent charge may be present), and then the monoPEGylated materials are separated using size exclusion chromatography.

MonoPEG (30 kD), Linear)-ylated IFN-α

PEGylated IFN-α that is suitable for use in the present invention includes a monopegylated consensus interferon (CIFN) molecule comprised of a single CIFN polypeptide and a single polyethylene glycol (PEG) moiety, where the PEG moiety is linear and about 30 kD in molecular weight and is directly or indirectly linked through a stable covalent linkage to either the N-terminal residue in the CIFN polypeptide or a lysine residue in the CIFN polypeptide. In some embodiments, the monoPEG (30 kD, linear)-ylated IFN-α is monoPEG (30 kD, linear)-ylated consensus IFN-α.

In some embodiments, the PEG moiety is linked to either the alpha-amino group of the N-terminal residue in the CIFN polypeptide or the epsilon-amino group of a lysine residue in the CIFN polypeptide. In further embodiments, the linkage comprises an amide bond between the PEG moiety and either the alpha-amino group of the N-terminal residue or the epsilon-amino group of the lysine residue in the CIFN polypeptide. In still further embodiments, the linkage comprises an amide bond between a propionyl group of the PEG moiety and either the alpha-amino group of the N-terminal residue or the epsilon-amino group of the lysine residue in the CIFN polypeptide. In additional embodiments, the amide bond is formed by condensation of an alpha-methoxy, omega-propanoic acid activated ester of the PEG moiety and either the alpha-amino group of the N-terminal residue or the epsilon-amino group of the lysine residue in the CIFN polypeptide, thereby forming a hydrolytically stable linkage between the PEG moiety and the CIFN polypeptide.

In some embodiments, the PEG moiety is linked to the N-terminal residue in the CIFN polypeptide. In other embodiments, the PEG moiety is linked to the alpha-amino group of the N-terminal residue in the CIFN polypeptide. In further embodiments, the linkage comprises an amide bond between the PEG moiety and the alpha-amino group of the N-terminal residue in the CIFN polypeptide. In still further embodiments, the linkage comprises an amide bond between a propionyl group of the PEG moiety and the alpha-amino group of the N-terminal residue in the CIFN polypeptide. In additional embodiments, the amide bond is formed by condensation of an alpha-methoxy, omega-propanoic acid activated ester of the PEG moiety and the alpha-amino group of the N-terminal residue of the CIFN polypeptide.

In some embodiments, the PEG moiety is linked to a lysine residue in the CIFN polypeptide. In other embodiments, the PEG moiety is linked to the epsilon-amino group of a lysine residue in the CIFN polypeptide. In further embodiments, the linkage comprises an amide bond between the PEG moiety and the epsilon-amino group of the lysine group in the CIFN polypeptide. In still further embodiments, the linkage comprises an amide bond between a propionyl group of the PEG moiety and the epsilon-amino group of the lysine group in the CIFN polypeptide. In additional embodiments, the amide bond is formed by condensation of an alpha-methoxy, omega-propanoic acid activated ester of the PEG moiety and the epsilon-amino group of the lysine residue in the CIFN polypeptide.

In some embodiments, the PEG moiety is linked to a surface-exposed lysine residue in the CIFN polypeptide. In other embodiments, the PEG moiety is linked to the epsilon-amino group of a surface-exposed lysine residue in the CIFN polypeptide. In further embodiments, the linkage comprises an amide bond between the PEG moiety and the epsilon-amino group of the surface-exposed lysine residue in the CIFN polypeptide. In still further embodiments, the linkage comprises an amide bond between a propionyl group of the PEG moiety and the epsilon-amino group of the surface-exposed lysine residue in the CIFN polypeptide. In additional embodiments, the amide bond is formed by condensation of an alpha-methoxy, omega-propanoic acid activated ester of the PEG moiety and the epsilon-amino group of the surface-exposed lysine residue in the CIFN polypeptide.

In some embodiments, the PEG moiety is linked to a lysine chosen from $lys^{31}$, $lys^{50}$, $lys^{71}$, $lys^{84}$, $lys^{121}$, $lys^{122}$, $lys^{134}$, $lys^{135}$, and $lys^{165}$ of the CIFN polypeptide. In other embodiments, the PEG moiety is linked to the epsilon-amino group of a lysine chosen from $lys^{31}$, $lys^{50}$, $lys^{71}$, $lys^{84}$, $lys^{121}$, $lys^{122}$, $lys^{134}$, $lys^{135}$, and $lys^{165}$ of the CIFN polypeptide. In further embodiments, the linkage comprises an amide bond between the PEG moiety and the epsilon-amino group of the chosen lysine residue in the CIFN polypeptide. In still further embodiments, the linkage comprises an amide bond between a propionyl group of the PEG moiety and the epsilon-amino group of the chosen lysine residue in the CIFN polypeptide. In additional embodiments, the amide bond is formed by condensation of an alpha-methoxy, omega-propanoic acid activated ester of the PEG moiety and the epsilon-amino group of the chosen lysine residue in the CIFN polypeptide.

In some embodiments, the PEG moiety is linked to a lysine chosen from $lys^{121}$, $lys^{134}$, $lys^{135}$, and $lys^{165}$ of the CIFN polypeptide. In other embodiments, the PEG moiety is linked to the epsilon-amino group of a lysine chosen from $lys^{121}$, $lys^{134}$, $lys^{135}$, and $lys^{165}$ of the CIFN polypeptide. In further embodiments, the linkage comprises an amide bond between the PEG moiety and the epsilon-amino group of the chosen lysine residue in the CIFN polypeptide. In still further embodiments, the linkage comprises an amide bond between a propionyl group of the PEG moiety and the epsilon-amino group of the chosen lysine residue in the CIFN polypeptide. In additional embodiments, the amide bond is formed by condensation of an alpha-methoxy, omega-propanoic acid activated ester of the PEG moiety and the epsilon-amino group of the chosen lysine residue in the CIFN polypeptide.

In connection with the above-described monopegylated CIFN molecules, the invention contemplates use of embodiments of each such molecule where the CIFN polypeptide is chosen from interferon alpha-con$_1$, interferon alpha-con$_2$, and interferon alpha-con$_3$, the amino acid sequences of which CIFN polypeptides are disclosed in U.S. Pat. No. 4,695,623.

Populations of IFN-α

In addition, any of the methods of the invention can employ a PEGylated IFN-α composition that comprises a population of monopegylated IFNα molecules, where the population consists of one or more species of monopegylated IFNα molecules as described above. Thus, in some embodiments, the composition comprises a population of modified IFN-α polypeptides, each with a single PEG molecule linked to a single amino acid residue of the polypeptide.

In some of these embodiments, the population comprises a mixture of a first IFN-α polypeptide linked to a PEG molecule at a first amino acid residue; and at least a second IFN-α polypeptide linked to a PEG molecule at a second amino acid residue, wherein the first and second IFN-α polypeptides are the same or different, and wherein the location of the first amino acid residue in the amino acid sequence of the first IFN-α polypeptide is not the same as the location of the second amino acid residue in the second IFN-α polypeptide. As one non-limiting example, an IFN-α composition comprises a population of PEG-modified IFN-α polypeptides, the population comprising an IFN-α polypeptide linked at its amino terminus to a linear PEG molecule; and an IFN-α polypeptide linked to a linear PEG molecule at a lysine residue.

Generally, a given modified IFN-α species represents from about 0.5% to about 99.5% of the total population of monopegylated IFNα polypeptide molecules in a population, e.g, a given modified IFN-α species represents about 0.5%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 99.5% of the total population of monopegylated IFN-α polypeptide molecules in a population. In some embodiments, an IFN-α composition comprises a population of monopegylated IFN-α polypeptides, which population comprises at least about 70%, at least about 80%, at least about 90%, at least about 95%, or at least about 99%, IFN-α polypeptides linked to PEG at the same site, e.g., at the N-terminal amino acid.

In particular embodiments of interest, an IFN-α composition comprises a population of monopegylated CIFN molecules, the population consisting of one or more species of molecules, where each species of molecules is characterized by a single CIFN polypeptide linked, directly or indirectly in a covalent linkage, to a single linear PEG moiety of about 30 kD in molecular weight, and where the linkage is to either a lysine residue in the CIFN polypeptide, or the N-terminal amino acid residue of the CIFN polypeptide.

The amino acid residue to which the PEG is attached is in many embodiments the N-terminal amino acid residue. In other embodiments, the PEG moiety is attached (directly or via a linker) to a surface-exposed lysine residue. In additional embodiments, the PEG moiety is attached (directly or via a linker) to a lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$ of the CIFN polypeptide. In further embodiments, the PEG moiety is attached (directly or via a linker) to a lysine residue chosen from $lys^{121}$, $lys^{134}$, $lys^{135}$, and $lys^{165}$ of the CIFN polypeptide.

As an example, in some embodiments, an IFN-α composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first lysine residue of a second CIFN polypeptide, where the first and second CIFN polypeptides are the same or different. An IFN-α composition can further comprise at least one additional monopegylated CIFN polypeptide species of molecules characterized by a PEG moiety linked to a lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another example, in some embodiments, an IFN-α composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first surface-exposed lysine residue of a second CIFN polypeptide, where the first and second CIFN polypeptides are the same or different. An IFN-α composition can further comprise at least one additional monopegylated CIFN polypeptide species of molecules characterized by a PEG moiety linked to a surface-exposed lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another example, in some embodiments, an IFN-α composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first lysine residue selected from one of $lys^{31}$, $lys^{50}$, $lys^{71}$, $lys^{84}$, $lys^{121}$, $lys^{122}$, $lys^{134}$, $lys^{135}$, and $lys^{165}$ in a second CIFN polypeptide, where the first and second CIFN polypeptides are the same or different. An IFN-α composition can further comprise a third monopegylated CIFN polypeptide species of molecules characterized by a PEG moiety linked to a second lysine residue selected from one of $lys^{31}$, $lys^{50}$, $lys^{71}$, $lys^{84}$, $lys^{121}$, $lys^{122}$, $lys^{134}$, $lys^{135}$, and $lys^{165}$ in a third CIFN polypeptide, where the third CIFN polypeptide is the same or different from either of the first and second CIFN polypeptides, where the second lysine residue is located in a position in the amino acid sequence of the third CIFN polypeptide that is not the same as the position of the first lysine residue in the amino acid sequence of the second CIFN polypeptide. A composition suitable for use in a subject method may further comprise at least one additional monopegylated CIFN polypeptide species of molecules characterized by a PEG moiety linked to one of $lys^{31}$, $lys^{50}$, $lys^{71}$, $lys^{84}$, $lys^{121}$, $lys^{122}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another example, in some embodiments, an IFN-α composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first lysine residue selected from one of $lys^{121}$, $lys^{134}$, $lys^{135}$, and $lys^{165}$ in a second CIFN polypeptide, where the first and second CIFN polypeptides are the same or different. A composition suitable for use in a subject method can further comprise a third monopegylated CIFN polypeptide species of molecules characterized by a PEG moiety linked to a second lysine residue selected from one of $lys^{121}$, $lys^{134}$, $lys^{135}$, and $lys^{165}$ in a third CIFN polypeptide, where the third CIFN polypeptide is the same or different from either of the first and second CIFN polypeptides, where the second lysine residue is located in a position in the amino acid sequence of the third CIFN polypeptide that is not the same as the position of the first lysine residue in the amino acid sequence of the second CIFN polypeptide. An IFN-α composition may further comprise at least one additional monopegylated CIFN polypeptide species of molecules characterized by a PEG moiety linked to one of $lys^{121}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, in some embodiments, a composition suitable for use in a subject method comprises a population of monopegylated CIFN molecules, consisting of a first monopegylated CIFN polypeptide species of molecules characterized by a PEG moiety linked to a first lysine residue in a first CIFN polypeptide; and a second monopegylated CIFN polypeptide species of molecules characterized by a PEG moiety linked at a second lysine residue in a second CIFN polypeptide, where the first and second CIFN polypeptides are the same or different, and where the first lysine is located in a position in the amino acid sequence of the first CIFN polypeptide that is not the same as the position of the second lysine residue in the amino acid sequence of the second CIFN polypeptide. An IFN-α composition may further comprise at least one additional monopegylated CIFN species of molecules characterized by a PEG moiety linked to a lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, in some embodiments, an IFN-α composition suitable for use in a subject method comprises a population of monopegylated CIFN molecules, consisting of a first monopegylated CIFN polypeptide species of molecules characterized by a PEG moiety linked at a first lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$ in a first CIFN polypeptide; and a second monopegylated CIFN polypeptide species of molecules characterized by a PEG moiety linked at a second lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$ in a second CIFN polypeptide, where the first and second CIFN polypeptides are the same or different, and where the second lysine residue is located in a position in the amino acid sequence of the second CIFN polypeptide that is not the same as the position of the first lysine residue in the first CIFN polypeptide. The composition may further comprise at least one additional monopegylated CIFN polypeptide species of molecules characterized by a PEG moiety linked to one of $lys^{31}$, $lys^{50}$, $lys^{71}$, $lys^{84}$, $lys^{121}$, $lys^{122}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, in some embodiments, an IFN-α composition suitable for use in a subject method comprises a population of monopegylated CIFN molecules, consisting of a first monopegylated CIFN polypeptide species of molecules characterized by a PEG moiety linked at a first lysine residue chosen from $lys^{121}$, $lys^{134}$, $lys^{135}$, and $lys^{165}$ in a first CIFN polypeptide; and a second monopegylated CIFN polypeptide species of molecules characterized by a PEG moiety linked at a second lysine residue chosen from $lys^{121}$, $lys^{134}$, $lys^{135}$, and $lys^{165}$ in a second CIFN polypeptide, where the first and second CIFN polypeptides are the same or different, and where the second lysine residue is located in a position in the amino acid sequence of the second CIFN polypeptide that is not the same as the position of the first lysine residue in the first CIFN polypeptide. The composition may further comprise at least one additional monopegylated CIFN polypeptide species of molecules characterized by a PEG moiety linked to one of $lys^{121}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, in some embodiments, an IFN-α composition suitable for use in a subject method comprises a monopegylated population of CIFN molecules, consisting of a first monopegylated CIFN polypeptide species of molecules characterized by a PEG moiety linked to a first surface-exposed lysine residue in a first CIFN polypeptide; and a second monopegylated CIFN polypeptide species of molecules characterized by a PEG moiety linked at a second surface-exposed lysine residue in a second CIFN polypeptide, where the first and second CIFN polypeptides are the same or different, and where the first surface-exposed lysine is located in a position in the amino acid sequence of the first CIFN polypeptide that is not the same as the position of the second surface-exposed lysine residue in the amino acid sequence of the second CIFN polypeptide. An IFN-α composition may further comprise at least one additional monopegylated CIFN species of molecules characterized by a PEG moiety linked to a surface-exposed lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

In connection with each of the above-described populations of monopegylated CIFN molecules, the invention contemplates use of embodiments where the molecules in each such population comprise a CIFN polypeptide chosen from interferon alpha-$con_1$, interferon alpha-$con_2$, and interferon alpha-$con_3$.

The invention further features use in a subject method of a product that is produced by the process of reacting CIFN polypeptide with a succinimidyl ester of alpha-methoxy, omega-propionylpoly(ethylene glycol) (mPEGspa) that is linear and about 30 kD in molecular weight, where the reactants are initially present at a molar ratio of about 1:1 to about 1:5 CIFN:mPEGspa, and where the reaction is conducted at a pH of about 7 to about 9, followed by recovery of the monopegylated CIFN product of the reaction. In one embodiment, the reactants are initially present at a molar ratio of about 1:3 CIFN:mPEGspa and the reaction is conducted at a pH of about 8. In another embodiment where the modified IFN-α is generated by a scaled-up procedure needed for toxicological and clinical investigations, the reactants are initially present in a molar ratio of 1:2 CIFN:mPEGspa and the reaction is conducted at a pH of about 8.0.

In connection with the above-described product-by-process, the invention contemplates use of embodiments where the CIFN reactant is chosen from interferon alpha-$con_1$, interferon alpha-$con_2$, and interferon alpha-$con_3$.

In some embodiments, the present invention contemplates use of a known hyperglycosylated polypeptide variant of a parent protein therapeutic. In some embodiments, the parent protein therapeutic is an interferon, and a known hyperglycosylated polypeptide variant comprises (1) a carbohydrate moiety covalently attached to at least one non-native glycosylation site not found in the parent interferon and/or (2) a carbohydrate moiety covalently attached to at least one native glycosylation site found but not glycosylated in the parent interferon.

In some embodiments, the known hyperglycosylated polypeptide variant is any glycosylated synthetic Type I interferon receptor polypeptide agonist.

Suitable known hyperglycosylated polypeptide variants include hyperglycosylated forms of any parent alpha interferon polypeptide. In one aspect, a known hyperglycosylated variant of a parent alpha interferon polypeptide has an amino acid sequence that differs from the amino acid sequence of the parent polypeptide to the extent that the variant comprises one or more glycosylation sites not found in the parent polypeptide.

In another aspect, the parent polypeptide is IFN-α2a and the known hyperglycosylated polypeptide variant is an [D99N]IFN-α2a glycopeptide, where the [D99N]IFN-α2a glycopeptide is a variant of IFN-α2a having (a) an asparagine residue in place of the native aspartic acid residue at amino acid position 99 in the amino acid sequence of IFN-α2a and (b) a carbohydrate moiety covalently attached to the R-group of said asparagine residue.

In another aspect, the parent polypeptide is IFN-α2a and the known hyperglycosylated polypeptide variant is an [D99N, D105N]IFN-α2a glycopeptide, where the [D99N, D105N]IFN-α2a glycopeptide is a variant of IFN-α2a having (a) an asparagine residue in place of the native aspartic acid residue at each of amino acid positions 99 and 105 in the amino acid sequence of IFN-α2a and (b) a carbohydrate moiety covalently attached to the R-group of each of said asparagine residues.

In another aspect, the parent polypeptide is IFN-α2b and the known hyperglycosylated polypeptide variant is an [D99N]IFN-α2b glycopeptide, where the [D99N]IFN-α2b glycopeptide is a variant of IFN-α2b having (a) an asparagine residue in place of the native aspartic acid residue at amino acid position 99 in the amino acid sequence of IFN-α2b and (b) a carbohydrate moiety covalently attached to the R-group of said asparagine residue.

In another aspect, the parent polypeptide is IFN-α2b and the known hyperglycosylated polypeptide variant is an [D99N, D105N]IFN-α2b glycopeptide, where the [D99N, D105N]IFN-α2b glycopeptide is a variant of IFN-α2b having (a) an asparagine residue in place of the native aspartic acid residue at each of amino acid positions 99 and 105 in the amino acid sequence of IFN-α2b and (b) a carbohydrate moiety covalently attached to the R-group of each of said asparagine residues.

Suitable alpha interferons further include consensus IFN-α. Consensus IFN-α (also referred to as "CIFN" and "IFN-con" and "consensus interferon") encompasses but is not limited to the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1).

Suitable known hyperglycosylated polypeptide variants include hyperglycosylated forms of any parent consensus IFN-α polypeptide. In one aspect, a known hyperglycosylated variant of a parent consensus IFN-α polypeptide has an amino acid sequence that differs from the amino acid sequence of the parent polypeptide to the extent that the variant comprises one or more glycosylation sites not found in a parent polypeptide.

In another aspect, the parent polypeptide is the interferon alfacon-1 polypeptide and the known hyperglycosylated polypeptide variant is an [D99N]interferon alfacon-1 glycopeptide, where the [D99N]interferon alfacon-1 glycopeptide is a variant of the interferon alfacon-1 polypeptide having (a) an asparagine residue substituted for the native aspartic acid residue at amino acid position 99 in the amino acid sequence of Infergen (interferon alfacon-1) and (b) a carbohydrate moiety covalently attached to the R-group of said asparagine residue.

In another aspect, the parent polypeptide is the interferon alfacon-1 polypeptide and the known hyperglycosylated polypeptide variant is an [D99N, D105N]interferon alfacon-1 glycopeptide, where the [D99N, D105N]interferon alfacon-1 glycopeptide is a variant of the interferon alfacon-1 polypeptide having (a) an asparagine residue substituted for each of the native aspartic acid residues at amino acid positions 99 and 105 in the amino acid sequence of Infergen and (b) a carbohydrate moiety covalently attached to the R-group of each of said asparagine residues.

In another aspect, the parent polypeptide is the interferon alfacon-1 polypeptide and the known hyperglycosylated polypeptide variant is an [D99N, D105N, E134N]interferon alfacon-1 glycopeptide, where the [D99N, D105N, E134N] interferon alfacon-1 glycopeptide is a variant of the interferon alfacon-1 polypeptide having (a) an asparagine residue substituted for each of the native aspartic acid, aspartic acid, and glutamic acid residues at amino acid positions 99, 105 and 134, respectively, in the amino acid sequence of Infergen and (b) a carbohydrate moiety covalently attached to the R-group of each of said asparagine residues.

In another aspect, the parent polypeptide is the interferon alfacon-1 polypeptide and the known hyperglycosylated polypeptide variant is an [D99N, E134N]interferon alfacon-1 glycopeptide, where the [D99N, E134N] interferon alfacon-1 glycopeptide is a variant of the interferon alfacon-1 polypeptide having (a) an asparagine residue substituted for each of the native aspartic acid and glutamic acid residues at amino acid positions 99 and 134, respectively, in the amino acid sequence of Infergen and (b) a carbohydrate moiety covalently attached to the R-group of each of said asparagine residues.

In another aspect, the parent polypeptide is the interferon alfacon-1 polypeptide and the known hyperglycosylated polypeptide variant is an [D105N, E134N]interferon alfacon-1 glycopeptide, where the [D105N, E134N] interferon alfacon-1 glycopeptide is a variant of the interferon alfacon-1 polypeptide having (a) an asparagine residue substituted for each of the native aspartic acid and glutamic acid residues at amino acid positions 105 and 134, respectively, in the amino acid sequence of Infergen and (b) a carbohydrate moiety covalently attached to the R-group of each of said asparagine residues.

In another aspect, the parent polypeptide is the interferon alfacon-1 polypeptide and the known hyperglycosylated polypeptide variant is an [D99N, D105N, E134T]interferon alfacon-1 glycopeptide, where the [D99N, D105N, E134T] interferon alfacon-1 glycopeptide is a variant of the interferon alfacon-1 polypeptide having (a) an asparagine residue substituted for each of the native aspartic acid residues at amino acid positions 99 and 105 in the amino acid sequence of Infergen (b) a threonine residue substituted for the native glutamic acid residue at amino acid position 134 in the amino acid sequence of Infergen and (c) a carbohydrate moiety covalently attached to the R-group of each of said asparagine and threonine residues.

In another aspect, the parent polypeptide is the interferon alfacon-1 polypeptide and the known hyperglycosylated polypeptide variant is an [D99N, E134T]interferon alfacon-1 glycopeptide, where the [D99N, E134T]interferon alfacon-1 glycopeptide is a variant of the interferon alfacon-1 polypeptide having (a) an asparagine residue substituted for the native aspartic acid residue at amino acid position 99 in the amino acid sequence of Infergen (b) a threonine residue substituted for the native glutamic acid residue at amino acid position 134 in the amino acid sequence of Infergen and (c) a carbohydrate moiety covalently attached to the R-group of each of said asparagine and threonine residues.

In another aspect, the parent polypeptide is the interferon alfacon-1 polypeptide and the known hyperglycosylated polypeptide variant is an [D105N, E134T]interferon alfacon-1 glycopeptide, where the [D105N, E134T]interferon alfacon-1 glycopeptide is a variant of the interferon alfacon-1 polypeptide having (a) an asparagine residue substituted for the native aspartic acid residue at amino acid position 105 in the amino acid sequence of Infergen (b) a threonine residue substituted for the native glutamic acid residue at amino acid position 134 in the amino acid sequence of Infergen and (c) a carbohydrate moiety covalently attached to the R-group of each of said asparagine and threonine residues.

In another aspect, a known hyperglycosylated polypeptide variant of a parent interferon-alpha therapeutic differs from the parent interferon-alpha therapeutic to the extent that the known hyperglycosylated polypeptide variant comprises (1) a carbohydrate moiety covalently attached to a non-native glycosylation site not found in the parent interferon-alpha therapeutic and/or (2) a carbohydrate moiety covalently attached to a native glycosylation site found but not glycosylated in the parent interferon-alpha therapeutic.

IFN-β

In some embodiments, the at least one additional therapeutic agent in a subject combination therapy includes an IFN-β. The term interferon-beta ("IFN-β") includes IFN-β polypeptides that are naturally occurring; non-naturally-occurring IFN-β polypeptides; and analogs and variants of naturally occurring or non-naturally occurring IFN-β that retain antiviral activity of a parent naturally-occurring or non-naturally occurring IFN-β.

Any of a variety of beta interferons can be used in a subject treatment method. Suitable beta interferons include, but are not limited to, naturally-occurring IFN-β; IFN-β1a, e.g., Avonex® (Biogen, Inc.), and Rebif® (Serono, SA); IFN-β1b (Betaseron®; Berlex); and the like.

The IFN-β formulation may comprise an N-blocked species, wherein the N-terminal amino acid is acylated with an acyl group, such as a formyl group, an acetyl group, a malonyl group, and the like. Also suitable for use is a consensus IFN-β.

IFN-β polypeptides can be produced by any known method. DNA sequences encoding IFN-β may be synthesized using standard methods. In many embodiments, IFN-β polypeptides are the products of expression of manufactured DNA sequences transformed or transfected into bacterial hosts, e.g., E. coli, or in eukaryotic host cells (e.g., yeast; mammalian cells, such as CHO cells; and the like). In these embodiments, the IFN-β is "recombinant IFN-β." Where the host cell is a bacterial host cell, the IFN-β is modified to comprise an N-terminal methionine.

It is to be understood that IFN-β as described herein may comprise one or more modified amino acid residues, e.g., glycosylations, chemical modifications, and the like.

IFN-tau

In some embodiments, the at least one additional therapeutic agent in a subject combination therapy includes an IFN-tau. The term "interferon-tau" (IFN-tau) includes IFN-tau polypeptides that are naturally occurring; non-naturally-occurring IFN-tau polypeptides; and analogs and variants of naturally occurring or non-naturally occurring IFN-tau that retain antiviral activity of a parent naturally-occurring or non-naturally occurring IFN-tau.

Suitable tau interferons include, but are not limited to, naturally-occurring IFN-tau; Tauferon® (Pepgen Corp.); and the like.

IFN-tau may comprise an amino acid sequence as set forth in any one of GenBank Accession Nos. P15696; P56828; P56832; P56829; P56831; Q29429; Q28595; Q28594; S08072; Q08071; Q08070; Q08053; P56830; P28169; P28172; and P28171. The sequence of any known IFN-tau polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The IFN-tau formulation may comprise an N-blocked species, wherein the N-terminal amino acid is acylated with an acyl group, such as a formyl group, an acetyl group, a malonyl group, and the like. Also suitable for use is a consensus IFN-tau.

IFN-tau polypeptides can be produced by any known method. DNA sequences encoding IFN-tau may be synthesized using standard methods. In many embodiments, IFN-tau polypeptides are the products of expression of manufactured DNA sequences transformed or transfected into bacterial hosts, e.g., E. coli, or in eukaryotic host cells (e.g., yeast; mammalian cells, such as CHO cells; and the like). In these embodiments, the IFN-tau is "recombinant IFN-tau." Where the host cell is a bacterial host cell, the IFN-tau is modified to comprise an N-terminal methionine.

It is to be understood that IFN-tau as described herein may comprise one or more modified amino acid residues, e.g., glycosylations, chemical modifications, and the like.

IFN-ω

In some embodiments, the at least one additional therapeutic agent in a subject combination therapy includes in IFN-omega. The term interferon-omega ("IFN-ω") includes IFN-ω polypeptides that are naturally occurring; non-naturally-occurring IFN-ω polypeptides; and analogs and variants of naturally occurring or non-naturally occurring IFN-ω that retain antiviral activity of a parent naturally-occurring or non-naturally occurring IFN-ω.

Any known omega interferon can be used in a subject treatment method. Suitable IFN-ω include, but are not limited to, naturally-occurring IFN-ω; recombinant IFN-ω, e.g., Biomed 510 (BioMedicines); and the like.

IFN-ω may comprise an amino acid sequence as set forth in GenBank Accession No. NP_002168; or AAA70091. The sequence of any known IFN-ω polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The IFN-ω formulation may comprise an N-blocked species, wherein the N-terminal amino acid is acylated with an acyl group, such as a formyl group, an acetyl group, a malonyl group, and the like. Also suitable for use is a consensus IFN-ω.

IFN-ω polypeptides can be produced by any known method. DNA sequences encoding IFN-ω may be synthesized using standard methods. In many embodiments, IFN-ω polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-ω is "recombinant IFN-ω." Where the host cell is a bacterial host cell, the IFN-ω is modified to comprise an N-terminal methionine.

It is to be understood that IFN-ω as described herein may comprise one or more modified amino acid residues, e.g., glycosylations, chemical modifications, and the like.

Type III Interferon Receptor Agonists

In some embodiments, the at least one additional therapeutic agent in a subject combination therapy includes a Type III interferon receptor agonist. Type III interferon agonists include an IL-28b polypeptide; and IL-28a polypeptide; and IL-29 polypeptide; antibody specific for a Type III interferon receptor; and any other agonist of Type III interferon receptor, including non-polypeptide agonists IL-28A, IL-28B, and IL-29 (referred to herein collectively as "Type III interferons" or "Type III IFNs") are described in Sheppard et al. (2003) *Nature* 4:63-68. Each polypeptide binds a heterodimeric receptor consisting of IL-10 receptor β chain and an IL-28 receptor α. Sheppard et al. (2003), supra. The amino acid sequences of IL-28A, IL-28B, and IL-29 are found under GenBank Accession Nos. NP_742150, NP_742151, and NP_742152, respectively.

The amino acid sequence of a Type III IFN polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Included for use in a subject method are polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) *J. Biol. Chem.* 275:23783-23789). Analogs may be used that include residues other than naturally occurring L-amino acids, e.g. D-amino acids or non-naturally occurring synthetic amino acids. The protein may be pegylated to enhance stability. The polypeptides may be fused to albumin.

The polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Type II Interferon Receptor Agonists

In some embodiments, the at least one additional therapeutic agent in a subject combination therapy includes a Type II interferon receptor agonist. Thus, in some embodiments, a subject combination therapy method comprises administering effective amounts of an α-glucosidase inhibitor and a Type II interferon receptor agonist. As used herein, the term "Type II interferon receptor agonist" includes any naturally occurring or non-naturally-occurring ligand of a human Type II interferon receptor that binds to and causes signal transduction via the receptor. Type II interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

A specific example of a Type II interferon receptor agonist is IFN-gamma and variants thereof. While the present invention exemplifies use of an IFN-gamma polypeptide, it will be readily apparent that any Type II interferon receptor agonist can be used in a subject method.

Interferon-Gamma

The nucleic acid sequences encoding IFN-gamma polypeptides may be accessed from public databases, e.g., Genbank, journal publications, and the like. While various mammalian IFN-gamma polypeptides are of interest, for the treatment of human disease, generally the human protein will be used. Human IFN-gamma coding sequence may be found in Genbank, accession numbers X13274; V00543; and NM_000619. The corresponding genomic sequence may be found in Genbank, accession numbers J00219; M37265; and V00536. See, for example. Gray et al. (1982) *Nature* 295:501 (Genbank X13274); and Rinderknecht et al. (1984) *J.B.C.* 259:6790. In some embodiments, the IFN-γ is glycosylated.

IFN-γ1b (Actimmune®; human interferon) is a single-chain polypeptide of 140 amino acids. It is made recombinantly in *E. coli* and is unglycosylated (Rinderknecht et al. 1984, *J. Biol. Chem.* 259:6790-6797). Recombinant IFN-gamma as discussed in U.S. Pat. No. 6,497,871 is also suitable for use herein.

The IFN-gamma to be used in a subject method may be any of natural IFN-gamma, recombinant IFN-gamma and the derivatives thereof so far as they have an IFN-γ activity, particularly human IFN-gamma activity. Human IFN-gamma exhibits the antiviral and anti-proliferative properties characteristic of the interferons, as well as a number of other immunomodulatory activities, as is known in the art. Although IFN-gamma is based on the sequences as provided above, the production of the protein and proteolytic processing can result in processing variants thereof. The unprocessed sequence provided by Gray et al., supra, consists of 166 amino acids (aa). Although the recombinant IFN-gamma produced in *E. coli* was originally believed to be 146 amino acids, (commencing at amino acid 20) it was subsequently found that native human IFN-gamma is cleaved after residue 23, to produce a 143 aa protein, or 144 aa if the terminal methionine is present, as required for expression in bacteria. During purification, the mature protein can additionally be cleaved at the C terminus after reside 162 (referring to the Gray et al. sequence), resulting in a protein of 139 amino acids, or 140 amino acids if the initial methionine is present, e.g. if required for bacterial expression. The N-terminal methionine is an artifact encoded by the mRNA translational "start" signal AUG that, in the particular case of *E. coli* expression is not processed away. In other microbial systems or eukaryotic expression systems, methionine may be removed.

For use in a subject method, any of the native IFN-gamma peptides, modifications and variants thereof, or a combination of one or more peptides may be used. IFN-gamma peptides of interest include fragments, and can be variously truncated at the carboxyl terminus relative to the full sequence. Such fragments continue to exhibit the characteristic properties of human gamma interferon, so long as amino acids 24 to about 149 (numbering from the residues of the unprocessed polypeptide) are present. Extraneous sequences can be substituted for the amino acid sequence following amino acid 155 without loss of activity. See, for example, U.S. Pat. No. 5,690,925. Native IFN-gamma moieties include molecules variously extending from amino acid residues 24-150; 24-151, 24-152; 24-153, 24-155; and 24-157. Any of these variants, and other variants known in the art and having IFN-γ activity, may be used in a subject method.

The sequence of the IFN-γ polypeptide may be altered in various ways known in the art to generate targeted changes in sequence. A variant polypeptide will usually be substantially similar to the sequences provided herein, i.e., will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. IFN-gamma may be modified with one or more polyethylene glycol moieties (PEGylated). In one embodiment, the invention contemplates the use of IFN-gamma variants with one or more non-naturally occurring glycosylation and/or pegylation sites that are engineered to provide glycosyl- and/or PEG-derivatized polypeptides with reduced serum clearance, such as the IFN-gamma polypeptide variants described in International Patent Publication No. WO 01/36001 and WO 02/081507. Also included are modifications of glycosylation, e.g., those made by modifying the glycosylation patterns of a polypeptide during its synthesis and processing or in further processing steps; e.g., by exposing the polypeptide to enzymes that affect glycosylation, such as mammalian glycosylating or deglycosylating enzymes. Also embraced are sequences that have phosphorylated amino acid residues, e.g., phosphotyrosine, phosphoserine, or phosphothreonine.

Included for use in the subject invention are IFN-γ polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see, for example, Friedler et al. 2000, *J. Biol. Chem.* 275: 23783-23789). Analogs may be used that include residues other than naturally occurring L-amino acids, e.g., D-amino acids or non-naturally occurring synthetic amino acids. The protein may be pegylated to enhance stability.

In some embodiments, the present invention contemplates use of a known hyperglycosylated polypeptide variant of a parent protein therapeutic. In some. embodiments, the parent protein therapeutic is an interferon, and a known hyperglycosylated polypeptide variant comprises (1) a carbohydrate moiety covalently attached to at least one non-native glycosylation site not found in the parent interferon and/or (2) a carbohydrate moiety covalently attached to at least one native glycosylation site found but not glycosylated in the parent interferon.

In some embodiments, the parent polypeptide is a Type II interferon receptor polypeptide agonist. Type II interferon receptor polypeptide agonists include interferon-gamma (IFN-γ). Thus, e.g., a known hyperglycosylated polypeptide variant can be a hyperglycosylated Type II interferon receptor polypeptide agonist variant, including hyperglycosylated IFN-γ.

Any of the native IFN-gamma peptides, modifications and variants thereof, or a combination of one or more peptides can serve as a parent polypeptide referent in connection with the present methods and/or compositions. IFN-gamma peptides of interest include fragments, and can be variously truncated at the carboxyl terminus relative to the full sequence. Such fragments continue to exhibit the characteristic properties of human gamma interferon, so long as. amino acids 24 to about 149 (numbering from the residues of the unprocessed polypeptide) are present. Extraneous sequences can be substituted for the amino acid sequence following amino acid 155 without loss of activity. See, for example, U.S. Pat. No. 5,690,925. Native IFN-gamma moieties include molecules variously extending from amino acid residues 24-150; 24-151, 24-152; 24-153, 24-155; and 24-157.

Any known hyperglycosylated IFN-gamma polypeptide variant that retains a desired pharmacologic activity of a parent IFN-gamma polypeptide may be used in the methods and/or compositions of the invention.

In one aspect, the parent polypeptide is the mature, native IFN-gamma polypeptide; and the hyperglycosylated polypeptide variant of the parent polypeptide is an [S99T]IFN-gamma glycopeptide, where the [S99T]IFN-gamma glycopeptide is a variant of the mature, native IFN-gamma having (a) a threonine residue substituted for the native serine residue at amino acid position 99 in the amino acid sequence of IFN-gamma and (b) a carbohydrate moiety covalently attached to the R-group of the asparagine residue at amino acid position 97 in the amino acid sequence of (a).

Since the glycosylation site formed by N97, Y98, T99 in the [S99T]IFN-gamma variant is different than the glycosylation site formed by N97, Y98, S99 in native IFN-gamma, the N97, Y98, T99 glycosylation site qualifies as a non-native glycosylation site not found in the parent polypeptide. In addition, as described in WO 02/081507, the S99T substitution in the amino acid sequence of native IFN-gamma provides for greater efficiency of glycosylation at the N97, Y98, T99 glycosylation site in the [S99T]IFN-gamma variant compared to the efficiency of glycosylation at the N97, Y98, S99 glycosylation site in native IFN-gamma. Thus, [S99T]IFN-gamma qualifies as a hyperglycosylated polypeptide variant of the parent IFN-gamma polypeptide.

In another aspect, the parent polypeptide is mature, native IFN-gamma; and the hyperglycosylated polypeptide variant of the parent polypeptide is an [E38N]IFN-gamma glycopeptide, where the [E38N]IFN-gamma glycopeptide is a variant of the mature, native IFN-gamma having (a) an asparagine residue substituted for the native glutamic acid residue at amino acid position 38 in the amino acid sequence of IFN-gamma and (b) a carbohydrate moiety covalently attached to the R-group of the asparagine residue at amino acid position 38 in the amino acid sequence of (a).

In another aspect, the parent polypeptide is mature, native IFN-gamma; and the hyperglycosylated polypeptide variant of the parent polypeptide is an [E38N, S99T]IFN-gamma glycopeptide, where the [E38N, S99T]IFN-gamma glycopeptide is a variant of the mature, native IFN-gamma having (a) asparagine and threonine residues substituted for the native glutamic acid and serine residues at amino acid positions 38 and 99 in the amino acid sequence of IFN-gamma and (b) a carbohydrate moiety covalently attached to the R-group of the asparagine residue at each of amino acid positions 38 and 97 in the amino acid sequence of (a).

In another aspect, the parent polypeptide is mature, native IFN-gamma; and the hyperglycosylated polypeptide variant of the parent polypeptide is an [E38N, S40T]IFN-gamma glycopeptide, where the [E38N, S40T]IFN-gamma glycopeptide is a variant of the mature, native IFN-gamma having (a) asparagine and threonine residues substituted for the native glutamic acid and serine residues at amino acid positions 38 and 40 in the amino acid sequence of IFN-gamma and (b) a carbohydrate moiety covalently attached to the R-group of the asparagine residue at amino acid position 38 in the amino acid sequence (a).

In another aspect, the parent polypeptide is mature, native IFN-gamma having the amino acid sequence; and the hyperglycosylated polypeptide variant of the parent polypeptide is an [E38N, S40T, S99T]IFN-gamma glycopeptide, where the [E38N, S40T, S99T]IFN-gamma glycopeptide is a variant of the mature, native IFN-gamma having (a) asparagine, threonine and threonine residues substituted for the native glutamic acid, serine and serine residues at amino acid positions 38, 40 and 99, respectively, in the amino acid sequence of IFN-gamma and (b) a carbohydrate moiety covalently attached to the R-group of the asparagine residue at amino acid position 38 in the amino acid sequence of (a), and optionally further having (c) a carbohydrate moiety covalently attached to the R-group of the asparagine residue at amino acid position 97 in the amino acid sequence of IFN-gamma.

In another aspect, a known hyperglycosylated polypeptide variant of a parent interferon-gamma therapeutic differs from the parent interferon-gamma therapeutic to the extent that the known hyperglycosylated polypeptide variant comprises (1) a carbohydrate moiety covalently attached to a non-native glycosylation site not found in the parent interferon-gamma therapeutic and/or (2) a carbohydrate moiety covalently attached to a native glycosylation site found but not glycosylated in the parent interferon-gamma therapeutic.

In another aspect, the parent protein therapeutic is interferon gamma-1b and the known hyperglycosylated polypeptide variant of the parent interferon gamma-1b therapeutic is glycosylated native (wild-type) human IFN-γ as described in WO 02/081507.

The IFN-γ polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using a liquid chromatography method (e.g., high performance liquid chromatography), size exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Ribavirin

In some embodiments, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The invention also contemplates use of derivatives of ribavirin (see, e.g., U.S. Pat. No. 6,277,830). The ribavirin may be administered orally in capsule or tablet form, or in the same or different administration form and in the same or different route as the α-glucosidase inhibitor. Of course, other types of administration of both medicaments, as they become available are contemplated, such as by nasal spray, transdermally, by suppository, by sustained release dosage form, etc. Any form of administration will work so long as the proper dosages are delivered without destroying the active ingredient.

Ribavirin is generally administered in an amount ranging from about 400 mg to about 1200 mg, from about 600 mg to about 1000 mg, or from about 700 to about 900 mg per day. In some embodiments, ribavirin is administered throughout the entire course of α-glucosidase inhibitor therapy. In other embodiments, ribavirin is administered only during the first period of time. In still other embodiments, ribavirin is administered only during the second period of time.

Levovirin

In some embodiments, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

Levovirin has the following structure:

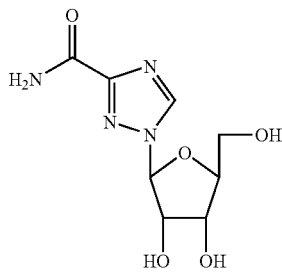

Viramidine

In some embodiments, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Viramidine has the following structure:

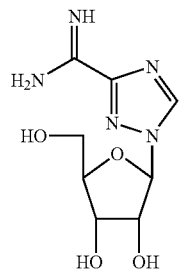

Nucleoside Analogs

Nucleoside analogs that are suitable for use in a subject combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2':4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, $O^2,O^2$-anhydro-β-L-arabinofuranosyluracil, 2'-deoxy-β-L-uridine, 3'5'-Di-O-benzoyl-2'deoxy-4-thioβ-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.);. a nucleoside analog as disclosed in WO 02/057287 A2 or WO 02/057425 A2 (both Merck/Isis); and the like.

HCV NS3 Inhibitors

In some embodiments, the at least one additional suitable therapeutic agent includes HCV NS3 inhibitors. Suitable HCV non-structural protein-3 (NS3) inhibitors include, but are not limited to, a tri-peptide as disclosed in U.S. Pat. Nos. 6,642,204, 6,534,523, 6,420,380, 6,410,531, 6,329,417, 6,329,379, and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309, 6,608,067, and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003) *J. Biol. Chem.* 278:20374-20380; NS3 inhibitor BILN 2061 (Boehringer-Ingelheim; Lamarre et al. (2002) *Hepatology* 36:301A; and Lamarre et al. (Oct. 26, 2003) *Nature* doi: 10.1038/nature02099); NS3 inhibitor VX-950 (Vertex Pharmaceuticals; Kwong et al. (Oct. 24-28, 2003) 54th Ann. Meeting AASLD); NS3 inhibitor SCH6 (Abib et al. (Oct. 24-28, 2003) Abstract 137. Program and Abstracts of the 54th Annual Meeting of the American Association for the Study of Liver Diseases (AASLD). Oct. 24-28, 2003. Boston, Mass.); any of the NS3 protease inhibitors disclosed in WO 99/07733, WO 99/07734, WO 00/09558, WO 00/09543, WO 00/59929 or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926); an NS3 protease inhibitor as disclosed in any one of U.S. Patent Publication Nos. 2003019067, 20030187018, and 20030186895; and the like.

Of particular interest in many embodiments are NS3 inhibitors that are specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B.

NS5B Inhibitors

In some embodiments, the at least one additional suitable therapeutic agent includes NS5B inhibitors. Suitable HCV non-structural protein-5 (NS5; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) *Antimicrob. Agents Chemother.* 47:2674-2681; a benzothiadiazine compound as disclosed in Dhanak et al. (2002) *J. Biol Chem.* 277(41): 38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

Of particular interest in many embodiments are NS5 inhibitors that are specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

Additional Antiviral Therapeutic Agents

Additional antiviral therapeutic agents that can be administered in a subject combination therapy include, but are not limited to, inhibitors of inosine monophosphate dehydrogenase (IMPDH); ribozymes that are complementary to viral nucleotide sequences; antisense RNA inhibitors; and the like.

IMPDH Inhibitors

IMPDH inhibitors that are suitable for use in a subject combination therapy include, but are not limited to, VX-497 ((S)-N-3-[3-(3-methoxy-4-oxazol-5-yl-phenyl)-ureido]-benzyl-carbamic acid tetrahydrofuran-3-yl-ester); Vertex Pharmaceuticals; see, e.g., Markland et al. (2000) *Antimicrob. Agents Chemother.* 44:859-866); ribavirin; levovirin (Ribapharm; see, e.g., Watson (2002) *Curr Opin Investig Drugs* 3(5):680-3); viramidine (Ribapharm); and the like.

Ribozyme and Antisense

Ribozyme and antisense antiviral agents that are suitable for use in a subject combination therapy include, but are not limited to, ISIS 14803 (ISIS Pharmaceuticals/Elan Corporation; see, e.g., Witherell (2001) *Curr Opin Investig Drugs.* 2(11):1523-9); Heptazyme™; and the like.

Side Effect Management Agents

In some embodiments, a subject therapy further comprises administering a palliative agent (e.g., an agent that reduces patient discomfort caused by a therapeutic agent), or other agent for the avoidance, treatment, or reduction of a side effect of a therapeutic agent. Such agents are also referred to as "side effect management agents." Suitable side effect management agents include agents for the avoidance, treatment, or reduction of a side effect of an agent that inhibits enzymatic activity of a membrane-bound α-glucosidase; agents for the avoidance, treatment, or reduction of a side effect of a Type I interferon receptor agonist; agents for the avoidance, treatment, or reduction of a side effect of a Type II interferon receptor agonist; and the like.

Suitable side effect management agents include agents that are effective in pain management; agents that ameliorate gastrointestinal discomfort; analgesics, anti-inflammatories, antipsychotics, antineurotics, anxiolytics, and hematopoietic agents. In addition, the invention contemplates the use of any compound for palliative care of patients suffering from pain or any other side effect in the course of treatment with a subject therapy. Exemplary palliative agents include acetaminophen, ibuprofen, and other NSAIDs, H2 blockers, and antacids.

Analgesics that can be used to alleviate pain in the methods of the invention include non-narcotic analgesics such as non-steroidal anti-inflammatory drugs (NSAIDs) acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing.

Other suitable analgesics include fentanyl, buprenorphine, codeine sulfate, morphine hydrochloride, codeine, hydromorphone (Dilaudid), levorphanol (Levo-Dromoran), methadone (Dolophine), morphine, oxycodone (in Percodan), and oxymorphone (Numorphan). Also suitable for use are benzodiazepines including, but not limited to, flurazepam (Dalmane), diazepam (Valium), and Versed, and the like.

Anti-inflammatory Agents

Suitable anti-inflammatory agents include, but are not limited to, steroidal anti-inflammatory agents, and non-steroidal anti-inflammatory agents.

Suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures of two or more of the foregoing.

Suitable non-steroidal anti-inflammatory agents, include, but are not limited to, 1) the oxicams, such as piroxicam, isoxicam, tenoxicam, and sudoxicam; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and 6) the pyrazoles, such as phenylbutazone, oxyphenbutazone, feprazone, azapropazone, and trimethazone, mixtures of these non-steroidal anti-inflammatory agents may also be employed, as well as the pharmaceutically-acceptable salts and esters of these agents.

Suitable anti-inflammatory agents include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; -Dexamethasone Dipropionate; Diclofenac Potassium; Diclofenac Sodium; Diflorasone Diacetate; -Diflumidone Sodium; Diflunisal; Difluprednate; Diftalone; Dimethyl Sulfoxide; Drocinonide; Endrysone; Enlimomab Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antipsychotic and antineurotic drugs that can be used to alleviate psychiatric side effects in the methods of the invention include any and all selective serotonin receptor inhibitors (SSRIs) and other anti-depressants, anxiolytics (e.g. alprazolam), etc. Anti-depressants include, but are not limited to, serotonin reuptake inhibitors such as Celexa®, Desyrel®, Effexor®, Luvox®, Paxil®, Prozac®, Zoloft®, and Serzone®; tricyclics such as Adapin®, Anafrinil®, Elavil®, Janimmine®, Ludiomil®, Pamelor®, Tofranil®, Vivactil®, Sinequan®, and Surmontil®; monoamine oxidase inhibitors such as Eldepryl®, Marplan®, Nardil®, and Parnate®. Anti-anxiety agents include, but are not limited to, azaspirones such as BuSpar®, benzodiazepines such as Ativan®, Librium®, Tranxene®, Centrax®, Klonopin®, Paxipam®, Serax®, Valium®, and Xanax®; and beta-blockers such as Inderal® and Tenormin®.

Agents that reduce gastrointestinal discomfort such as nausea, diarrhea, gastrointestinal cramping, and the like are suitable palliative agents for use in a subject combination therapy. Suitable agents include, but are not limited to, antiemetics, anti-diarrheal agents, H2 blockers, antacids, and the like.

Suitable H2 blockers (histamine type 2 receptor antagonists) that are suitable for use as a palliative agent in a subject therapy include, but are not limited to, Cimetidine (e.g., Tagamet, Peptol, Nu-cimet, apo-cimetidine, non-cimetidine); Ranitidine (e.g., Zantac, Nu-ranit, Novo-randine, and apo-ranitidine); and Famotidine (Pepcid, Apo-Famotidine, and Novo-Famotidine).

Suitable antacids include, but are not limited to, aluminum and magnesium hydroxide (Maalox®, Mylanta®); aluminum carbonate gel (Basajel®); aluminum hydroxide (Amphojel®, AlternaGEL®); calcium carbonate (Tums®, Titralac®); magnesium hydroxide; and sodium bicarbonate.

Antiemetics include, but are not limited to, 5-hydroxytryptophan-3 (5HT3) inhibitors; corticosteroids such as dexamethasone and methylprednisolone; Marinol® (dronabinol); prochlorperazine; benzodiazepines; promethazine; and metoclopramide cisapride; Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Fludorex; Flumeridone; Galdansetron Hydrochloride; Granisetron; Granisetron Hydrochloride; Lurosetron Mesylate; Meclizine Hydrochloride; Metoclopramide Hydrochloride; Metopimazine; Ondansetron Hydrochloride; Pancopride; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; Zacopride Hydrochloride.

Anti-diarrheal agents include, but are not limited to, Rolgamidine, Diphenoxylate hydrochloride (Lomotil), Metronidazole (Flagyl), Methylprednisolone (Medrol), Sulfasalazine (Azulfidine), and the like.

Suitable hematopoietic agents that can be used to prevent or restore depressed blood cell populations in the methods of the invention include erythropoietins, such as EPOGEN™ epoetin-alfa, granulocyte colony stimulating factors (G-CSFs), such as NEUPOGEN™ filgrastim, granulocyte-macrophage colony stimulating factors (GM-CSFs), thrombopoietins, etc.

Dosages, Formulations, and Routes of Administration

An active agent (e.g., an α-glucosidase inhibitor, at least one additional therapeutic agent, etc.) is administered to individuals in a formulation with a pharmaceutically acceptable excipient(s). The terms "active agent" and "therapeutic agent" are used interchangeably herein. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20$^{th}$ edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, an active agent (e.g., an α-glucosidase inhibitor, at least one additional therapeutic agent, etc.) may be administered to the host using any convenient means capable of resulting in the desired therapeutic effect. Thus, an active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of an active agent can be achieved in various ways, including oral, buccal, rectal, parenteral, intraperitoneal, intradermal, subcutaneous, intramuscular, transdermal, intratracheal, etc., administration. In some embodiments, two different routes of administration are used. For example, in some embodiments, an α-glucosidase inhibitor is administered orally, while IFN-γ or IFN-α is administered subcutaneously.

Subcutaneous administration of an active agent (e.g., an α-glucosidase inhibitor, at least one additional therapeutic agent, etc.) can be accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a therapeutic agent to a patient through the port is referred to herein as "a subcutaneous injection port delivery system." In some embodiments, subcutaneous administration is achieved by a combination of devices, e.g., bolus delivery by needle and syringe, followed by delivery using a continuous delivery system.

In some embodiments, an active agent (e.g., an α-glucosidase inhibitor, at least one additional therapeutic agent, etc.) is delivered by a continuous delivery system. The terms "continuous delivery system," "controlled delivery system," and "controlled drug delivery device," are used interchangeably to refer to controlled drug delivery devices, and encompass pumps in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, the present methods of drug delivery can be accomplished using any of a variety of refillable, pump systems. Pumps provide consistent, controlled release over time. Typically, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are generally used because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump are also suitable for use with the present invention. Examples of such devices include those described in, for example, U.S. Pat. Nos. 4,692,147; 4,360,019; 4,487,603; 4,360,019; 4,725,852, and the like. In general, a subject treatment method can be carried out using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in a subject treatment method include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted above, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, a therapeutic agent is delivered using an implantable drug delivery system, e.g., a system that is programmable to provide for administration of a therapeutic agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, an active agent (e.g., an α-glucosidase inhibitor, at least one additional therapeutic agent, etc.) is formulated alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives, and flavoring agents.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the agent(s) in a composition as a solution in sterile water, normal saline or another pharmaceutically acceptable carrier.

Dosages

The term "unit dosage form," as used herein, refers to physically discrete units suitable as unitary dosages for human and animal subjects, each unit containing a predetermined quantity of an active agent (e.g., an α-glucosidase inhibitor, at least one additional therapeutic agent, etc.) calculated in an amount sufficient to produce the desired effect in association with a pharmaceutically acceptable diluent, carrier or vehicle. The specifications for the unit dosage forms depend on the particular agent employed and the effect to be achieved, and the pharmacodynamics associated with each agent in the host.

Monotherapies

An agent that inhibits enzymatic activity of a membrane-bound α-glucosidase is useful in the treatment of a flavivirus infection, e.g., HCV infection, WNV infection, etc; as well as in the treatment of liver fibrosis that may occur as a result of, e.g., an HCV infection. A subject method that provides for administration of an agent that inhibits enzymatic activity of a membrane-bound α-glucosidase is also referred to herein as "an α-glucosidase inhibitor treatment" or "the α-glucosidase inhibitor treatment."

In many embodiments, an agent that inhibits enzymatic activity of a membrane-bound α-glucosidase is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

An agent that inhibits enzymatic activity of a membrane-bound α-glucosidase can be administered 5 times per day, 4 times per day, tid (three times daily), bid, qd, qod, biw, tiw, qw, qow, three times per month, or once monthly. In other embodiments, an agent that inhibits enzymatic activity of a membrane-bound α-glucosidase is administered as a continuous infusion.

In many embodiments, an agent that inhibits enzymatic activity of a membrane-bound α-glucosidase is administered orally.

In connection with the above-described methods for the treatment of a flavivirus infection, treatment of HCV infection, treatment of WNV infection, and treatment of liver fibrosis that occurs as a result of an HCV infection, an agent that inhibits enzymatic activity of a membrane-bound α-glucosidase is administered to the patient at a dosage of from about 30 mg per day to about 600 mg per day in divided doses, e.g., from about 30 mg per day to about 60 mg per day, from about 60 mg per day to about 75 mg per day, from about 75 mg per day to about 90 mg per day, from about 90 mg per day to about 120 mg per day, from about 120 mg per day to about 150 mg per day, from about 150 mg per day to about 180 mg per day, from about 180 mg per day to about 210 mg per day, from about 210 mg per day to about 240 mg per day, from about 240 mg per day to about 270 mg per day, from about 270 mg per day to about 300 mg per day, from about 300 mg per day to about 360 mg per day, from about 360 mg per day to about 420 mg per day, from about 420 mg per day to about 480 mg per day, or from about 480 mg to about 600 mg per day.

In some embodiments, an agent that inhibits enzymatic activity of a membrane-bound α-glucosidase is administered in a dosage of about 25 mg three times daily. In some embodiments, an agent that inhibits enzymatic activity of a membrane-bound α-glucosidase is administered in a dosage of about 50 mg three times daily. In some embodiments, an agent that inhibits enzymatic activity of a membrane-bound α-glucosidase is administered in a dosage of about 100 mg three times daily. In some embodiments, an agent that inhibits enzymatic activity of a membrane-bound α-glucosidase is administered in a dosage of about 75 mg per day to about 150 mg per day in two or three divided doses, where the individual weighs 60 kg or less. In some embodiments, an agent that inhibits enzymatic activity of a membrane-bound α-glucosidase is administered in a dosage of about 75 mg per day to about 300 mg per day in two or three divided doses, where the individual weighs 60 kg or more.

The amount of active ingredient (e.g., an agent that inhibits enzymatic activity of a membrane-bound α-glucosidase) that may be combined with carrier materials to produce a dosage form can vary depending on the host to be treated and the particular mode of administration. A typical pharmaceutical preparation can contain from about 5% to about 95% active ingredient (w/w), and in some cases from about 95% to about 98%, or from about 98% to about 99% (w/w) active ingredient). In other embodiments, the pharmaceutical preparation can contain from about 20% to about 80% active ingredient.

Those of skill will readily appreciate that dose levels can vary as a function of the specific agent that inhibits enzymatic activity of a membrane-bound α-glucosidase, the severity of the symptoms and the susceptibility of the subject to side effects. Preferred dosages for a given agent that inhibits enzymatic activity of a membrane-bound α-glucosidase are readily determinable by those of skill in the art by a variety of means. A typical means is to measure the physiological potency of a given active agent.

In many embodiments, multiple doses of an agent that inhibits enzymatic activity of a membrane-bound α-glucosidase are administered. For example, an agent that inhibits enzymatic activity of a membrane-bound α-glucosidase is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Methods of Treating a Flavivirus Infection

The present invention provides methods of treating a flavivirus infection by administering to an individual in need thereof a therapeutically effective amount of an agent that inhibits enzymatic activity of a membrane-bound α-glucosidase. Individuals who are to be treated according to the methods of the invention include individuals who have been clinically diagnosed with a flavivirus infection, as well as individuals who exhibit one or more of the signs and the symptoms of clinical infection but have not yet been diagnosed with an flavivirus infection.

In some embodiments, the invention provides a monotherapy method using an effective amount of an agent that inhibits a membrane-bound α-glucosidase in the treatment of a flavivirus infection in a patient, comprising administering to the patient the membrane-bound α-glucosidase inhibitor at a dosage of from about 25 mg to about 600 mg orally, subcutaneously, or intramuscularly bid, tid, qd, qod, tiw, or biw, or per day, substantially continuously or continuously, for the desired treatment duration.

In some embodiments, the invention provides a monotherapy method using an effective amount of an agent that inhibits a membrane-bound α-glucosidase in the treatment of a flavivirus infection in a patient, comprising administering to the patient the membrane-bound α-glucosidase inhibitor at a dosage of about 25 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient the membrane-bound α-glucosidase inhibitor at a dosage of about 50 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient the membrane-bound α-glucosidase inhibitor at a dosage of about 100 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient acarbose at a dosage of about 25 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient acarbose at a dosage of about 50 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient acarbose at a dosage of about 100 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient miglitol at a dosage of about 25 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient miglitol at a dosage of about 50 mg orally three times per day for the desired treatment duration.

In some embodiments, the invention provides a monotherapy method using an effective amount of an agent that inhibits a membrane-bound α-glucosidase in the treatment of a flavivirus infection in a patient, comprising administering to the patient miglitol at a dosage of about 100 mg orally three times per day for the desired treatment duration.

Methods of Treating a Hepatitis C Virus Infection

The present invention provides monotherapy methods of treating an HCV infection by administering to an individual in need thereof a therapeutically effective amount of an agent that inhibits enzymatic activity of a membrane-bound α-glucosidase. Individuals who are to be treated according to the methods of the invention include individuals who have been clinically diagnosed with an HCV infection, as well as individuals who exhibit one or more of the signs and the symptoms of clinical infection but have not yet been diagnosed with an HCV infection.

In some embodiments, the invention provides a monotherapy method using an effective amount of an agent that inhibits a membrane-bound α-glucosidase in the treatment of an HCV infection in a patient, comprising administering to the patient the membrane-bound α-glucosidase inhibitor at a dosage of from about 30 mg to about 600 mg orally, subcutaneously, or intramuscularly bid, tid, qd, qod, tiw, or biw, or per day, substantially continuously or continuously, for the desired treatment duration.

In some embodiments, the invention provides a monotherapy method using an effective amount of an agent that inhibits a membrane-bound α-glucosidase in the treatment of an HCV infection in a patient, comprising administering to the patient the membrane-bound α-glucosidase inhibitor at a dosage of about 25 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient the membrane-bound α-glucosidase inhibitor at a dosage of about 50 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient the membrane-bound α-glucosidase inhibitor at a dosage of about 100 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient acarbose at a dosage of about 25 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient acarbose at a dosage of about 50 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient acarbose at a dosage of about 100 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient miglitol at a dosage of about 25 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient miglitol at a dosage of about 50 mg orally three times per day for the desired treatment duration.

In some embodiments, the invention provides a monotherapy method using an effective amount of an agent that inhibits a membrane-bound α-glucosidase in the treatment of an HCV infection in a patient, comprising administering to the patient miglitol at a dosage of about 100 mg orally three times per day for the desired treatment duration.

Methods of treating a West Nile Virus Infection

The present invention provides monotherapy methods of treating a WNV infection by administering to an individual in need thereof a therapeutically effective amount of an agent that inhibits enzymatic activity of a membrane-bound α-glucosidase. Individuals who are to be treated according to the methods of the invention include individuals who have been clinically diagnosed with a WNV infection, as well as individuals who exhibit one or more of the signs and the symptoms of clinical infection but have not yet been diagnosed with a WNV infection.

In some embodiments, the invention provides a monotherapy method using an effective amount of an agent that inhibits a membrane-bound α-glucosidase in the treatment of a WNV infection in a patient, comprising administering to the patient the membrane-bound α-glucosidase inhibitor at a dosage of from about 30 mg to about 600 mg orally, subcutaneously, or intramuscularly bid, tid, qd, qod, tiw, or biw, or per day, substantially continuously or continuously, for the desired treatment duration.

In some embodiments, the invention provides a monotherapy method using an effective amount of an agent that inhibits a membrane-bound α-glucosidase in the treatment of a WNV infection in a patient, comprising administering to the patient the membrane-bound α-glucosidase inhibitor at a dosage of about 25 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient the membrane-bound α-glucosidase inhibitor at a dosage of about 50 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient the membrane-bound α-glucosidase inhibitor at a dosage of about 100 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient acarbose at a dosage of about 25 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient acarbose at a dosage of about 50 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient acarbose at a dosage of about 100 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient miglitol at a dosage of about 25 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient miglitol at a dosage of about 50 mg orally three times per day for the desired treatment duration.

In some embodiments, the invention provides a monotherapy method using an effective amount of an agent that inhibits a membrane-bound α-glucosidase in the treatment of a WNV infection in a patient, comprising administering to the patient miglitol at a dosage of about 100 mg orally three times per day for the desired treatment duration.

Combination Therapies

As discussed above, the present invention provides combination therapy methods of treating alphavirus infections; methods of treating flavivirus infections; methods of treating hepatitis C virus (HCV) infections; methods of treating West Nile virus (WNV) infection; methods of reducing liver fibrosis; methods of increasing liver function in an individual suffering from liver fibrosis; methods of reducing the incidence of complications associated with HCV and cirrhosis of the liver; and methods of reducing viral load, or reducing the time to viral clearance, or reducing morbidity or mortality in the clinical outcomes, in patients suffering from flavivirus infection. The methods generally involve administering to an individual in need thereof an effective amount an α-glucosidase inhibitor and at least a second therapeutic agent. Suitable additional therapeutic agents include, but are not limited to, a Type I interferon receptor agonist, a Type II interferon receptor agonist; a Type III interferon receptor agonist; a nucleoside analog; an NS3 inhibitor, an NS5B inhibitor, viramidine, and thymosin-α.

Alpha-glucosidase Inhibitors

Suitable α-glucosidase inhibitors include any of the above-described imino-sugars, including long-alkyl chain derivatives of imino sugars as disclosed in U.S. Patent Publication No. 2004/0110795; inhibitors of endoplasmic reticulum-associated α-glucosidases; inhibitors of membrane bound α-glucosidase; miglitol (Glyset®), and active derivatives, and analogs thereof; and acarbose (Precose®), and active derivatives, and analogs thereof.

In many embodiments, an α-glucosidase inhibitor is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

An α-glucosidase inhibitor can be administered 5 times per day, 4 times per day, tid (three times daily), bid, qd, qod, biw, tiw, qw, qow, three times per month, or once monthly. In other embodiments, an α-glucosidase inhibitor is administered as a continuous infusion.

In many embodiments, an α-glucosidase inhibitor is administered orally.

In connection with the above-described methods for the treatment of a flavivirus infection, treatment of HCV infection, treatment of WNV infection, and treatment of liver fibrosis that occurs as a result of an HCV infection, an α-glucosidase inhibitor is administered to the patient at a dosage of from about 10 mg per day to about 600 mg per day in divided doses, e.g., from about 10 mg per day to about 30 mg per day, from about 30 mg per day to about 60 mg per day, from about 60 mg per day to about 75 mg per day, from about 75 mg per day to about 90 mg per day, from about 90 mg per day to about 120 mg per day, from about 120 mg per day to about 150 mg per day, from about 150 mg per day to about 180 mg per day, from about 180 mg per day to about 210 mg per day, from about 210 mg per day to about 240 mg per day, from about 240 mg per day to about 270 mg per day, from about 270 mg per day to about 300 mg per day, from about 300 mg per day to about 360 mg per day, from about 360 mg per day to about 420 mg per day, from about 420 mg per day to about 480 mg per day, or from about 480 mg to about 600 mg per day.

In some embodiments, an α-glucosidase inhibitor is administered in a dosage of about 10 mg three times daily. In some embodiments, an α-glucosidase inhibitor is administered in a dosage of about 15 mg three times daily. In some embodiments, an α-glucosidase inhibitor is administered in a dosage of about 20 mg three times daily. In some embodiments, an α-glucosidase inhibitor is administered in a dosage of about 25 mg three times daily. In some embodiments, an α-glucosidase inhibitor is administered in a dosage of about 30 mg three times daily. In some embodiments, an α-glucosidase inhibitor is administered in a dosage of about 40 mg three times daily. In some embodiments, an α-glucosidase inhibitor is administered in a dosage of about 50 mg three times daily. In some embodiments, an α-glucosidase inhibitor is administered in a dosage of about 100 mg three times daily. In some embodiments, an α-glucosidase inhibitor is administered in a dosage of about 75 mg per day to about 150 mg per day in two or three divided doses, where the individual weighs 60 kg or less. In some embodiments, an α-glucosidase inhibitor is administered in a dosage of about 75 mg per day to about 300 mg per day in two or three divided doses, where the individual weighs 60 kg or more.

The amount of active ingredient (e.g., α-glucosidase inhibitor) that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific α-glucosidase inhibitor, the severity of the symptoms and the susceptibility of the subject to side effects. Preferred dosages for a given α-glucosidase inhibitor are readily determinable by those of skill in the art by a variety of means. A typical means is to measure the physiological potency of a given active agent.

In many embodiments, multiple doses of an α-glucosidase inhibitor are administered. For example, an α-glucosidase inhibitor is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Treatment Methods

In some embodiments, the invention provides a combination therapy method using combined effective amounts of i) an α-glucosidase inhibitor in the treatment of a flavivirus infection in a patient; and ii) at least one additional therapeutic agent in the treatment of a flavivirus infection (e.g., in the treatment of an HCV infection, in the treatment of a WNV infection, etc.), as well as in a method of reducing liver fibrosis, etc., in a patient. The method generally comprises co-administering to the patient a) a dosage of the α-glucosidase inhibitor; and b) a dosage of the at least one additional therapeutic agent for the desired treatment duration, to treat the flavivirus infection, reduce liver fibrosis, etc. In many embodiments, the α-glucosidase inhibitor is acarbose. In many embodiments, the α-glucosidase inhibitor is miglitol.

For convenience, the combination therapy treatment methods discussed below refer to "treating a flavivirus infection"; however, each combination therapy method is equally applicable to reducing liver fibrosis, reducing the incidence of liver cirrhosis, etc., as discussed above. Moreover, each of the combination therapy treatment methods discussed below that refer to "treating a flavivirus infection" are equally applicable to treating an HCV infection, e.g.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 10 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 15 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 20 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 25 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 30 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 35 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 40 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 50 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 60 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 70 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 75 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of acarbose containing an amount of 100 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 10 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 15 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol-containing an amount of 20 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 25 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 30 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 35 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 40 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 50 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 60 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 70 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 75 mg, administered orally tid; and b) a dosage of at least one additional therapeutic agent administered at the desired frequency and for the desired treatment duration, to treat the flavivirus infection.

In some embodiments, the invention provides a combination therapy method using combined effective amounts of i) an α-glucosidase inhibitor; and ii) at least one additional therapeutic agent in the treatment of a flavivirus infection in a patient, the method comprising co-administering to the patient a) a dosage of miglitol containing an amount of 100 mg, administered orally tid; and b) a dosage of at least one additional therapeutic agent administered at the desired frequency and for the desired treatment duration, to treat the flavivirus infection.

Combination Therapies with Type I Interferon Receptor Agonist

In some embodiments, the invention provides a combination therapy method using combined effective amounts of i) an α-glucosidase inhibitor in the treatment of a flavivirus infection in a patient; and ii) a Type I interferon receptor agonist and/or a Type III interferon receptor agonist in the treatment of a flavivirus infection in a patient. The method generally comprises co-administering to the patient a) a dosage of an α-glucosidase inhibitor; and b) a dosage of a Type I interferon receptor agonist and/or a Type III interferon receptor agonist for the desired treatment duration, to treat the flavivirus infection. In many embodiments, the Type I interferon receptor agonist is an IFN-α. In many embodiments, the α-glucosidase inhibitor is acarbose. In many embodiments, the α-glucosidase inhibitor is miglitol. In many embodiments, effective amounts of a Type I interferon receptor agonist and an α-glucosidase inhibitor are synergistic amounts.

Type I interferon receptor agonists suitable for use herein include any interferon-α (IFN-α). In certain embodiments, the interferon-α is a PEGylated interferon-α. In certain other embodiments, the interferon-α is a consensus interferon, such as INFERGEN® interferon alfacon-1. In still other embodiments, the interferon-α is a monoPEG (30 kD, linear)-ylated consensus interferon.

Effective dosages of an IFN-α range from about 1 μg to about 3 μg, from about 3 μg to about 27 μg, from about 3 MU to about 10 MU, from about 90 μg to about 180 μg, or from about 18 μg to about 90 μg. Effective dosages of Infergen® consensus IFN-α include about 3 μg, about 6 μg, about 9 μg, about 12 μg, about 15 μg, about 18 μg, about 21 μg, about 24 μg, about 27 μg, or about 30 μg, of drug per dose. Effective dosages of IFN-α2a and IFN-α2b range from 3 million Units (MU) to 10 MU per dose. Effective dosages of PEGASYS®PEGylated IFN-α2a contain an amount of about 90 µg to 270 µg, or about 180 µg, of drug per dose. Effective dosages of PEG-INTRON®PEGylated IFN-α2b contain an amount of about 0.5 µg to 3.0 µg of drug per kg of body weight per dose. Effective dosages of PEGylated consensus interferon (PEG-CIFN) contain an amount of about 18 µg to about 90 µg, or from about 27 µg to about 60 µg, or about 45 µg, of CIFN amino acid weight per dose of PEG-CIFN. Effective dosages of monoPEG (30 kD, linear)-ylated CIFN contain an amount of about 45 µg to about 270 µg, or about 60 µg to about 180 µg, or about 90 µg to about 120 µg, of drug per dose. IFN-α can be administered daily, every other day, once a week, three times a week, every other week, three times per month, once monthly, substantially continuously or continuously.

In many embodiments, the Type I or Type III interferon receptor agonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. Dosage regimens can include tid, bid, qd, qod, biw, tiw, qw, qow, three times per month, or monthly administrations. In some embodiments, the invention provides any of the above-described methods in which the desired dosage of IFN-α is administered subcutaneously to the patient by bolus delivery qd, qod, tiw, biw, qw, qow, three times per month, or monthly, or is administered subcutaneously to the patient per day by substantially continuous or continuous delivery, for the desired treatment duration. In other embodiments, the invention provides any of the above-described methods in which the desired dosage of PEGylated IFN-α (PEG-IFN-α) is administered subcutaneously to the patient by bolus delivery qw, qow, three times per month, or monthly for the desired treatment duration.

In some embodiments, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a Type I interferon receptor agonist selected from: (i) INFERGEN® containing an amount of about 1 µg to about 30 µg of drug per dose of INFERGEN® subcutaneously qd,-qod, tiw, biw, qw, qow, three times per month, once monthly, or per day continuously or substantially continuously (ii) PEGylated consensus IFN-α (PEG-CIFN) containing an amount of about 10 µg to about 100 µg, or about 40 µg to about 80 µg, of CIFN amino acid weight per dose of PEG-CIFN subcutaneously qw, qow, three times per month, or monthly (iii) IFN-α2a, 2b or 2c containing an amount of about 3 MU to about 10 MU of drug per dose of IFN-α2a, 2b or 2c subcutaneously qd, qod, tiw, biw, or per day continuously or substantially continuously (iv) PEGASYS® containing an amount of about 90 µg to about 360 µg, or about 180 µg, of drug per dose of PEGASYS® subcutaneously qw, qow, three times per month, or monthly (v) PEG-INTRON® containing an amount of about 0.75 µg to about 3.0 µg, or about 1.0 µg to about 1.5 µg, of drug per kilogram of body weight per dose of PEG-INTRON® subcutaneously biw, qw, qow, three times per month, or monthly or (vi) mono PEG(30 kD, linear)-ylated consensus IFN-α containing an amount of from about 100 µg to about 200 µg, or about 150 µg, of drug per dose of mono PEG(30 kD, linear)-ylated consensus IFN-α subcutaneously qw, qow, once every 8 days to once every 14 days, three times per month, or monthly for the desired treatment duration.

In some embodiments, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a Type I interferon receptor agonist selected from: (i) INFERGEN® containing an amount of about 1 µg to about 30 µg of drug per dose of INFERGEN® subcutaneously qd, qod, tiw, biw, qw, qow, three times per month, once monthly, or per day continuously or substantially continuously (ii) PEGylated consensus IFN-α (PEG-CIFN) containing an amount of about 10 µg to about 100 µg, or about 40 µg to about 80 µg, of CIFN amino acid weight per dose of PEG-CIFN subcutaneously qw, qow, three times per month, or monthly (iii) IFN-α 2a, 2b or 2c containing an amount of about 3 MU to about 10 MU of drug per dose of IFN-α 2a, 2b or 2c subcutaneously qd, qod, tiw, biw, or per day continuously or substantially continuously (iv) PEGASYS® containing an amount of about 90 µg to about 360 µg, or about 180 µg, of drug per dose of PEGASYS® subcutaneously qw, qow, three times per month, or monthly (v) PEG-INTRON® containing an amount of about 0.75 µg to about 3.0 µg, or about 1.0 µg to about 1.5 µg, of drug per kilogram of body weight per dose of PEG-INTRON® subcutaneously biw, qw, qow, three times per month, or monthly or (vi) mono PEG(30 kD, linear)-ylated consensus IFN-α containing an amount of from about 100 µg to about 200 µg, or about 150 µg, of drug per dose of mono PEG(30 kD, linear)-ylated consensus IFN-α subcutaneously qw, qow, once every 8 days to once every 14 days, three times per month, or monthly for the desired treatment duration.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of INFERGEN® containing an amount of about 1 µg to about 30 µg, e.g., 1 µg, 9 µg, 18 µg, 27 µg, or 30 µg of drug per dose of INFERGEN®, subcutaneously qd, qod, tiw, biw, qw, qow, three times per month, once monthly, or per day substantially continuously or continuously for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of INFERGEN® consensus IFN-α containing an amount of from about 1 μg to about 30 μg, e.g., 1 μg, 9 μg, 18 μg, 27 μg, or 30 μg INFERGEN® consensus IFN-α administered subcutaneously qd or tiw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of PEGASYS® PEGylated IFN-α2a containing an amount of about 90 μg to about 360 μg of drug per dose of PEGASYS®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of PEGASYS® PEGylated IFN-α2a containing an amount of about 180 μg of drug per dose of PEGASYS®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of PEG-INTRON® PEGylated IFN-α2b containing an amount of about 0.75 μg to about 3.0 μg of drug per kilogram of body weight per dose of PEG-INTRON®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of PEG-INTRON® containing an amount of about 1.5 μg of drug per kilogram of body weight per dose of PEG-INTRON®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-α containing an amount of 100 μg monoPEG(30 kD, linear)-ylated consensus IFN-α administered subcutaneously every 10 days or qw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-α containing an amount of 150 μg monoPEG(30 kD, linear)-ylated consensus IFN-α administered subcutaneously every 10 days or qw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-α containing an amount of 200 μg monoPEG(30 kD, linear)-ylated consensus IFN-α administered subcutaneously every 10 days or qw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of INFERGEN® containing an amount of about 1 μg to about 30 μg, e.g., 1 μg, 9 μg, 18 μg, 27 μg, or 30 μg of drug per dose of INFERGEN®, subcutaneously qd, qod, tiw, biw, qw, qow, three times per month, once monthly, or per day substantially continuously or continuously for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of INFERGEN® consensus IFN-α containing an amount of from about 1 μg to about 30 μg, e.g., 1 μg, 9 μg, 18 μg, 27 μg, or 30 μg INFERGEN® consensus IFN-α administered subcutaneously qd or tiw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of PEGASYS® PEGylated IFN-α2a containing an amount of about 90 μg to about 360 μg of drug per dose of PEGASYS®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg. acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of PEGASYS® PEGylated IFN-α2a containing an amount of about 180 μg of drug per dose of PEGASYS®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of PEG-INTRON® PEGylated IFN-α2b containing an amount of about 0.75 μg to about 3.0 μg of drug per kilogram of body weight per dose of PEG-INTRON®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of PEG-INTRON® containing an amount of about 1.5 μg of drug per kilogram of body weight per dose of PEG-INTRON®, subcutaneously qw, qow, three times per month, or monthly for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-α containing an amount of 100 μg monoPEG(30 kD, linear)-ylated consensus IFN-α administered subcutaneously every 10 days or qw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-α containing an amount of 150 μg monoPEG(30 kD, linear)-ylated consensus IFN-α administered subcutaneously every 10 days or qw for the desired treatment duration, to treat the flavivirus infection.

In some embodiments, the invention provides a combination therapy method using combined effective amounts of i) an α-glucosidase inhibitor; and ii) a Type I interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-α containing an amount of 200 μg monoPEG(30 kD, linear)-ylated consensus IFN-α administered subcutaneously every 10 days or qw for the desired treatment duration, to treat the flavivirus infection.

In some embodiments, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of 10 mg miglitol, administered orally tid; and b) administering a dosage of INFERGEN® containing an amount of about 1 µg of drug per dose of INFERGEN® consensus IFN-α subcutaneously tiw, for the desired treatment duration.

In one non-limiting example, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of 10 mg miglitol, administered orally tid; and b) administering a dosage of INFERGEN® consensus IFN-α containing an amount of about 9 µg of drug per dose of INFERGEN® consensus IFN-α subcutaneously tiw, for the desired treatment duration.

In one non-limiting example, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of 25 mg miglitol, administered orally tid; and b) administering a dosage of INFERGEN® consensus IFN-α containing an amount of about 9 µg of drug per dose of INFERGEN® consensus IFN-α subcutaneously tiw, for the desired treatment duration.

In one non-limiting example, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of 10 mg acarbose, administered orally tid; and b) administering a dosage of INFERGEN® consensus IFN-α containing an amount of about 1 µg of drug per dose of INFERGEN® consensus IFN-α subcutaneously tiw, for the desired treatment duration.

In one non-limiting example, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of 10 mg acarbose, administered orally tid; and b) administering a dosage of INFERGEN® consensus IFN-α containing an amount of about 9 µg of drug per dose of INFERGEN® consensus IFN-α subcutaneously tiw, for the desired treatment duration.

In one non-limiting example, the invention provides a combination therapy method using combined effective amounts of an α-glucosidase inhibitor; and a Type I interferon receptor agonist in the treatment of a flavivirus infection in a patient, the method comprising co-administering to the patient a) a dosage of an α-glucosidase inhibitor containing an amount of 25 mg acarbose, administered orally tid; and b) administering a dosage of INFERGEN® consensus IFN-α containing an amount of about 9 µg of drug per dose of INFERGEN® consensus IFN-α subcutaneously tiw, for the desired treatment duration.

Combination Therapies with a Type II Interferon Receptor Agonist

In some embodiments, the invention provides a combination therapy method using combined effective amounts of i) an α-glucosidase inhibitor in the treatment of a flavivirus infection in a patient; and ii) a Type II interferon receptor agonist in the treatment of a flavivirus infection in a patient. The method generally comprises co-administering to the patient a) a dosage of an α-glucosidase inhibitor; and b) a dosage of a Type II interferon receptor agonist for the desired treatment duration, to treat the flavivirus infection. In many embodiments, the Type II interferon receptor agonist is an IFN-γ. In many embodiments, the α-glucosidase inhibitor is acarbose. In many embodiments, the α-glucosidase inhibitor is miglitol. In many embodiments, effective amounts of a Type II interferon receptor agonist and an α-glucosidase inhibitor are synergistic amounts.

Effective dosages of IFN-γ can range from about $0.5 \mu g/m^2$ to about $500 \mu g/m^2$, usually from about $1.5 \mu g/m^2$ to $200 \mu g/m^2$, depending on the size of the patient. This activity is based on $10^6$ international units (U) per 50 µg of protein. IFN-γ can be administered daily, every other day, three times a week (tiw), or substantially continuously or continuously. In specific embodiments of interest, IFN-γ is administered to an individual in a unit dosage form of from about 25 µg to about 500 µg, from about 50 µg to about 400 µg, or from about 100 µg to about 300 µg. In particular embodiments of interest, the dose is about 200 µg IFN-γ. In many embodiments of interest, IFN-γ1b is administered. In some embodiments, the IFN-γ is Actimmune® human IFN-γ1b.

Where the dosage is 200 µg IFN-γ per dose, the amount of IFN-γ per body weight (assuming a range of body weights of from about 45 kg to about 135 kg) is in the range of from about 4.4 µg IFN-γ per kg body weight to about 1.48 µg IFN-γ per kg body weight.

The body surface area of individuals to be treated generally ranges from about $1.33 \text{ m}^2$ to about $2.50 \text{ m}^2$. Thus, in many embodiments, an IFN-γ dosage ranges from about $150 \mu g/m^2$ to about $20 \mu g/m^2$. For example, an IFN-γ dosage ranges from about $20 \mu g/m^2$ to about $30 \mu g/m^2$, from about $30 \mu g/m^2$ to about $40 \mu g/m^2$, from about $40 \mu g/m^2$ to about $50 \mu g/m^2$, from about $50 \mu g/m^2$ to about $60 \mu g/m^2$, from about $60 \mu g/m^2$ to about $70 \mu g/m^2$, from about $70 \mu g/m^2$ to about $80 \mu g/m^2$, from about $80 \mu g/m^2$ to about $90 \mu g/m^2$, from about $90 \mu g/m^2$ to about $100 \mu g/m^2$, from about $100 \mu g/m^2$ to about $110 \mu g/m^2$, from about $110 \mu g/m^2$ to about $120 \mu g/m^2$, from about $120 \mu g/m^2$ to about $130 \mu g/m^2$, from about $130 \mu g/m^2$ to about $140 \mu g/m^2$, or from about $140 \mu g/m^2$ to about $150 \mu g/m^2$. In some embodiments, the dosage groups range from about $25 \mu g/m^2$ to about $100 \mu g/m^2$. In other embodiments, the dosage groups range from about $25 \mu g/m^2$ to about $50 \mu g/m^2$.

In many embodiments, multiple doses of an IFN-γ are administered. For example, an IFN-γ is administered once per month, twice per month, three times per month, every other week (qow), once per week (qw), twice per week (biw), three times per week (tiw), four times per week, five times per week, six times per week, every other day (qod), daily (qd), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments, the IFN-γ is Actimmune® human IFN-γ1b, and is administered subcutaneously tiw in a dosage containing an amount of about 25 µg, 50 µg, 100 µg, 150 µg, or 200 µg.

In some embodiments, effective dosages of IFN-γ range from about $0.5 \mu g/m^2$ to about $500 \mu g/m^2$, e.g., from about 1.5

µg/m² to 200 µg/m², depending on the size of the patient. This activity is based on 10⁶ international units (IU) per 50 µg of protein.

Where the agent is a polypeptide, polynucleotide (e.g., a polynucleotide encoding IFN-γ), it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the therapeutic DNA, then bombarded into skin cells. Of particular interest in these embodiments is use of a liver-specific promoter to drive transcription of an operably linked IFN-γ coding sequence preferentially in liver cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

In particular embodiments of interest, IFN-γ is administered as a solution suitable for subcutaneous injection. For example, IFN-γ is in a formulation containing 40 mg mannitol/mL, 0.72 mg sodium succinate/mL, 0.10 mg polysorbate 20/mL. In particular embodiments of interest, IFN-γ is administered in single-dose forms of 200 µg/dose subcutaneously.

Multiple doses of IFN-γ can be administered, e.g., IFN-γ can be administered once per month, twice per month, three times per month, once per week, twice per week, three times per week, four times per week, five times per week, six times per week, or daily, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In particular embodiments of interest, IFN-γ is administered three times per week over a period of about 48 weeks.

In some embodiments, a Type II interferon receptor agonist (e.g., IFN-γ) is administered throughout the entire course of the α-glucosidase inhibitor treatment. In other embodiments, a Type II interferon receptor agonist is administered less than the entire course of α-glucosidase inhibitor treatment, e.g., only during the first phase of α-glucosidase inhibitor treatment, only during the second phase of α-glucosidase inhibitor treatment, or some other portion of the α-glucosidase inhibitor treatment regimen.

In some embodiments, the Type II interferon receptor agonist and the α-glucosidase inhibitor are administered in the same formulation, and are administered simultaneously. In other embodiments, the Type II interferon receptor agonist and the α-glucosidase inhibitor are administered separately, e.g., in separate formulations. In some of these embodiments, the Type II interferon receptor agonist and the α-glucosidase inhibitor are administered separately, and are administered simultaneously. In other embodiments, the Type II interferon receptor agonist and the α-glucosidase inhibitor are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 24 hours, or within about 24 hours to about 48 hours of one another.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a size-based dosage of IFN-γ containing an amount of from about 25 µg/m² to about 100 µg/m², or a fixed dosage of IFN-γ containing an amount of from about 50 µg to about 200 µg, administered subcutaneously tiw for the desired treatment duration, to treat the flavivirus infection.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a size-based dosage of IFN-γ containing an amount of from about 25 µg/m² to about 100 µg/m², or a fixed dosage of IFN-γ containing an amount of from about 50 µg to about 200 µg, administered subcutaneously tiw for the desired treatment duration, to treat the flavivirus infection.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 25 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 25 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 25 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 25 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 50 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 50 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 50 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 50 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 100 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 100 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 100 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 100 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 200 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of IFN-γ containing an amount of about 200 μg Actimmune® human IFN-γ1b administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 200 μg IFN-γ administered subcutaneously tiw, for the desired treatment duration.

In some embodiments, the invention provides a combination therapy method using combined effective amounts of an α-glucosidase inhibitor; and a Type II interferon receptor agonist in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of IFN-γ containing an amount of about 200 μg Actimmune® human IFN-γ1b administered subcutaneously tiw, for the desired treatment duration.

Combinations Using an α-Glucosidase Inhibitor, a Type I Interferon Receptor Agonist, and a Type II Interferon Receptor Agonist In some embodiments, the invention provides methods using an amount of a Type I or Type III interferon receptor agonist, a Type II interferon receptor agonist, and a α-glucosidase inhibitor, effective for the treatment of a flavivirus in a patient. In some embodiments, the invention provides methods using an effective amount of an IFN-α, IFN-γ, and an α-glucosidase inhibitor in the treatment of a flavivirus infection in a patient. In one embodiment, the invention provides a method using an effective amount of a consensus IFN-α, IFN-γ and a glucosidase inhibitor in the treatment of a flavivirus in a patient.

In some embodiments, a Type I or a Type III interferon receptor agonist is administered in a first dosing regimen, followed by a second dosing regimen. The first dosing regimen of Type I or a Type III interferon receptor agonist (also referred to as "the induction regimen ") generally involves administration of a higher dosage of the Type I or Type III interferon receptor agonist. For example, in the case of Infergen® consensus IFN-α (CIFN), the first dosing regimen comprises administering CIFN at about 9 μg, about 15 μg, about 18 μg, or about 27 μg. The first dosing regimen can encompass a single dosing event, or at least two or more dosing events. The first dosing regimen of the Type I or Type III interferon receptor agonist can be administered daily, every other day, three times a week, every other week, three times per month, once monthly, substantially continuously or continuously.

The first dosing regimen of the Type I or Type III interferon receptor agonist is administered for a first period of time, which time period can be at least about 4 weeks, at least about 8 weeks, or at least about 12 weeks.

The second dosing regimen of the Type I or Type III interferon receptor agonist (also referred to as "the maintenance dose") generally involves administration of a lower amount of the Type I or Type III interferon receptor agonist. For example, in the case of CIFN, the second dosing regimen comprises administering CIFN at a dose of at least about 3 μg, at least about 9 μg, at least about 15 μg, or at least about 18 μg. The second dosing regimen can encompass a single dosing event, or at least two or more dosing events.

The second dosing regimen of the Type I or Type III interferon receptor agonist can be administered daily, every other day, three times a week, every other week, three times per month, once monthly, substantially continuously or continuously.

In some embodiments, where an "induction"/"maintenance" dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase.

In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, the Type II interferon receptor agonist treatment is discontinued once Type I or a Type III interferon receptor agonist treatment begins.

In other embodiments, the Type I or Type III interferon receptor agonist is administered in single dosing regimen. For example, in the case of CIFN, the dose of CIFN is generally in a range of from about 3 µg to about 15 µg, or from about 9 µg to about 15 µg. The dose of Type I or a Type III interferon receptor agonist is generally administered daily, every other day, three times a week, every other week, three times per month, once monthly, or substantially continuously. The dose of the Type I or Type III interferon receptor agonist is administered for a period of time, which period can be, for example, from at least about 24 weeks to at least about 48 weeks, or longer.

In some embodiments, where a single dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase. In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with the Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, Type II interferon receptor agonist treatment is discontinued once Type I or a Type III interferon receptor agonist treatment begins.

In additional embodiments, an α-glucosidase inhibitor, a Type I or III interferon receptor agonist, and a Type II interferon receptor agonist are co-administered for the desired duration of treatment in the methods of the invention. In some embodiments, an α-glucosidase inhibitor, an interferon-α, and an interferon-γ are co-administered for the desired duration of treatment in the methods of the invention.

In general, an effective amount of a consensus interferon (CIFN) and IFN-γ suitable for use in the methods of the invention is provided by a dosage ratio of 1 µg CIFN: 10 µg IFN-γ, where in some embodiments, both CIFN and IFN-γ are unPEGylated and unglycosylated species.

In one embodiment, the invention provides any of the above-described methods modified to use an effective amount of INFERGEN® consensus IFN-α and IFN-γ in the treatment of a flavivirus infection in a patient comprising administering to the patient an α-glucosidase inhibitor; a dosage of INFERGEN® containing an amount of about 1 µg to about 30 µg, of drug per dose of INFERGEN®, subcutaneously qd, qod, tiw, biw, qw, qow, three times per month, once monthly, or per day substantially continuously or continuously; and a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, for the desired duration of treatment with the α-glucosidase inhibitor.

In another embodiment, the invention provides any of the above-described methods modified to use an effective amount of INFERGEN® consensus IFN-α and IFN-γ in the treatment of a flavivirus infection in a patient comprising administering to the patient a dosage of an α-glucosidase inhibitor; and a dosage of INFERGEN® containing an amount of about 1 µg to about 9 µg, of drug per dose of INFERGEN®, subcutaneously qd, qod, tiw, biw, qw, qow, three times per month, once monthly, or per day substantially continuously or continuously; in combination with a dosage of IFN-γ containing an amount of about 10 µg to about 100 µg of drug per dose of IFN-γ, subcutaneously qd, qod, tiw, biw, qw, qow, three times per month, once monthly, or per day substantially continuously or continuously, for the desired duration of treatment with the α-glucosidase inhibitor.

In another embodiment, the invention provides any of the above-described methods modified to use an effective amount of INFERGEN® consensus IFN-α and IFN-γ in the treatment of a flavivirus infection in a patient comprising administering to the patient a dosage of an α-glucosidase inhibitor; and a dosage of INFERGEN® containing an amount of about 1 µg of drug per dose of INFERGEN®, subcutaneously qd, qod, tiw, biw, qw, qow, three times per month, once monthly, or per day substantially continuously or continuously, in combination with a dosage of IFN-γ containing an amount of about 10 µg to about 50 µg of drug per dose of IFN-γ, subcutaneously qd, qod, tiw, biw, qw, qow, three times per month, once monthly, or per day substantially continuously or continuously, for the desired duration of treatment with the α-glucosidase inhibitor.

In another embodiment, the invention provides any of the above-described methods modified to use an effective amount of INFERGEN® consensus IFN-α and IFN-γ in the treatment of a flavivirus infection in a patient comprising administering to the patient a dosage of an α-glucosidase inhibitor; and a dosage of INFERGEN® containing an amount of about 9 µg of drug per dose of INFERGEN®, subcutaneously qd, qod, tiw, biw, qw, qow, three times per month, once monthly, or per day substantially continuously or continuously, in combination with a dosage of IFN-γ containing an amount of about 90 µg to about 100 µg of drug per dose of IFN-γ, subcutaneously qd, qod, tiw, biw, qw, qow, three times per month, once monthly, or per day substantially continuously or continuously, for the desired duration of treatment with the α-glucosidase inhibitor.

In another embodiment, the invention provides any of the above-described methods modified to use an effective amount of INFERGEN® consensus IFN-α and IFN-γ in the treatment of a flavivirus infection in a patient comprising administering to the patient a dosage of an α-glucosidase inhibitor; and a dosage of an α-glucosidase inhibitor; and a dosage of INFERGEN® containing an amount of about 30 µg of drug per dose of INFERGEN®, subcutaneously qd, qod, tiw, biw, qw, qow, three times per month, once monthly, or per day substantially continuously or continuously, in combination with a dosage of IFN-γ containing an amount of about 200 µg to about 300 µg of drug per dose of IFN-γ, subcutaneously qd, qod, tiw, biw, qw, qow, three times per month, once monthly, or per day substantially continuously or continuously, for the desired duration of treatment with the α-glucosidase inhibitor.

In another embodiment, the invention provides any of the above-described methods modified to use an effective amount of PEGylated consensus IFN-α and IFN-γ in the treatment of a flavivirus infection in a patient comprising administering to the patient a dosage of an α-glucosidase inhibitor; and a dosage of PEGylated consensus IFN-α (PEG- CIFN) containing an amount of about 4 µg to about 60 µg of CIFN amino acid weight per dose of PEG-CIFN, subcutaneously qw, qow, three times per month, or monthly, in combination with a total weekly dosage of IFN-γ containing an amount of about 30 µg to about 1,000 µg of drug per week in divided doses administered subcutaneously qd, qod, tiw, biw, or administered substantially continuously or continuously, for the desired duration of treatment with the α-glucosidase inhibitor.

In another embodiment, the invention provides any of the above-described methods modified to use an effective amount of PEGylated consensus IFN-α and IFN-γ in the treatment of a flavivirus infection in a patient comprising administering to the patient a dosage of an α-glucosidase inhibitor; and a dosage of PEGylated consensus IFN-α (PEG-CIFN) containing an amount of about 18 µg to about 24 µg of CIFN amino acid weight per dose of PEG-CIFN, subcutaneously qw, qow, three times per month, or monthly, in combination with a total weekly dosage of IFN-γ containing an amount of about 100 µg to about 300 µg of drug per week in divided doses administered subcutaneously qd, qod, tiw, biw, or substantially continuously or continuously, for the desired duration of treatment with the α-glucosidase inhibitor.

In general, an effective amount of IFN-α2a or 2b or 2c and IFN-γ suitable for use in the methods of the invention is provided by a dosage ratio of 1 million Units (MU) IFN-α 2a or 2b or 2c: 30 µg IFN-γ, where both IFN-α 2a or 2b or 2c and IFN-γ are unPEGylated and unglycosylated species.

In another embodiment, the invention provides any of the above-described methods modified to use an effective amount of IFN-α 2a or 2b or 2c and IFN-γ in the treatment of a flavivirus infection in a patient comprising administering to the patient a dosage of an α-glucosidase inhibitor; and a dosage of IFN-α 2a, 2b or 2c containing an amount of about 1 MU to about 20 MU of drug per dose of IFN-α 2a, 2b or 2c subcutaneously qd, qod, tiw, biw, or per day substantially continuously or continuously, in combination with a dosage of IFN-γ containing an amount of about 30 µg to about 600 µg of drug per dose of IFN-γ, subcutaneously qd, qod, tiw, biw, or per day substantially continuously or continuously, for the desired duration of treatment with the α-glucosidase inhibitor.

In another embodiment, the invention provides any of the above-described methods modified to use an effective amount of IFN-α 2a or 2b or 2c and IFN-γ in the treatment of a flavivirus infection in a patient comprising administering to the patient a dosage of an α-glucosidase inhibitor; and a dosage of IFN-α 2a, 2b or 2c containing an amount of about 3 MU of drug per dose of IFN-α 2a, 2b or 2c subcutaneously qd, qod, tiw, biw, or per day substantially continuously or continuously, in combination with a dosage of IFN-γ containing an amount of about 100 µg of drug per dose of IFN-γ, subcutaneously qd, qod, tiw, biw, or per day substantially continuously or continuously, for the desired duration of treatment with the α-glucosidase inhibitor.

In another embodiment, the invention provides any of the above-described methods modified to use an effective amount of IFN-α 2a or 2b or 2c and IFN-γ in the treatment of a flavivirus infection in a patient comprising administering to the patient a dosage of an α-glucosidase inhibitor; and a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of IFN-γ containing an amount of about 300 µg of drug per dose of IFN-γ, subcutaneously qd, qod, tiw, biw, or per day substantially continuously or continuously, for the desired duration of treatment with the α-glucosidase inhibitor.

In another embodiment, the invention provides any of the above-described methods modified to use an effective amount of PEGASYS® PEGylated IFN-α2a and IFN-γ in the treatment of a flavivirus infection in a patient comprising administering to the patient a dosage of an α-glucosidase inhibitor; and a dosage of PEGASYS® containing an amount of about 90 µg to about 360 µg of drug per dose of PEGASYS®, subcutaneously qw, qow, three times per month, or monthly, in combination with a total weekly dosage of IFN-γ containing an amount of about 30 µg to about 1,000 µg of drug per week administered in divided doses subcutaneously qd, qod, tiw, or biw, or administered substantially continuously or continuously, for the desired duration of treatment with the α-glucosidase inhibitor.

In another embodiment, the invention provides any of the above-described methods modified to use an effective amount of PEGASYS® PEGylated IFN-α2a and IFN-γ in the treatment of a flavivirus infection in a patient comprising administering to the patient a dosage of an α-glucosidase inhibitor; and a dosage of PEGASYS® containing an amount of about 180 µg of drug per dose of PEGASYS®, subcutaneously qw, qow, three times per month, or monthly, in combination with a total weekly dosage of IFN-γ containing an amount of about 100 µg to about 300 µg, of drug per week administered in divided doses subcutaneously qd, qod, tiw, or biw, or administered substantially continuously or continuously, for the desired duration of treatment with the α-glucosidase inhibitor.

In another embodiment, the invention provides any of the above-described methods modified to use an effective amount of PEG-INTRON® PEGylated IFN-α2b and IFN-γ in the treatment of a flavivirus infection in a patient comprising administering to the patient a dosage of an α-glucosidase inhibitor; and a dosage of PEG-INTRON® containing an amount of about 0.75 µg to about 3.0 µg of drug per kilogram of body weight per dose of PEG-INTRON®, subcutaneously qw, qow, three times per month, or monthly, in combination with a total weekly dosage of IFN-γ containing an amount of about 30 µg to about 1,000 µg of drug per week administered in divided doses subcutaneously qd, qod, tiw, or biw, or administered substantially continuously or continuously, for the desired duration of treatment with the α-glucosidase inhibitor.

In another embodiment, the invention provides any of the above-described methods modified to use an effective amount of PEG-INTRON® PEGylated IFN-α2b and IFN-γ in the treatment of a flavivirus infection in a patient comprising administering to the patient a dosage of an α-glucosidase inhibitor; and a dosage of PEG-INTRON® containing an amount of about 1.5 µg of drug per kilogram of body weight per dose of PEG-INTRON®, subcutaneously qw, qow, three times per month, or monthly, in combination with a total weekly dosage of IFN-γ containing an amount of about 100 µg to about 300 µg of drug per week administered in divided doses subcutaneously qd, qod, tiw, or biw, or administered substantially continuously or continuously, for the desired duration of treatment with the α-glucosidase inhibitor.

In one embodiment, the present invention provides any of the above-described methods modified to comprise administering to an individual having a flavivirus infection an effective amount of an α-glucosidase inhibitor; and a regimen of 1 µg, 3 µg, or 9 µg INFERGEN® consensus IFN-α administered subcutaneously qd or tiw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; and 50 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; and 100 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; 25 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; 200 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; and 25 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 9 μg INFERGEN® consensus IFN-α administered subcutaneously qd or tiw; and 200 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 100 μg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 100 μg monoPEG(30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 100 μg monoPEG(30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 100 μg monoPEG(30 kD, linear)-ylated consensus IFN-α administered subcutaneously every 10 days or qw; and 50 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 100 μg monoPEG(30 kD, linear)-ylated consensus IFN-α administered subcutaneously every 10 days or qw; and 100 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 150 μg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 150 μg monoPEG(30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 150 μg monoPEG(30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 150 μg monoPEG(30 kD, linear)-ylated consensus IFN-α administered subcutaneously every 10 days or qw; and 50 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 150 μg monoPEG(30 kD, linear)-ylated consensus IFN-α administered subcutaneously every 10 days or qw; and 100 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 200 μg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 200 μg monoPEG(30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 200 μg monoPEG(30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

In one embodiment, the present invention provides any of the above-described methods modified to comprise administering to an individual having an HCV infection an effective amount of an α-glucosidase inhibitor; and a regimen of 200 μg monoPEG(30 kD, linear)-ylated consensus IFN-α administered subcutaneously every 10 days or qw; and 50 μg Actimmune® human IFN-γ1b administered subcutaneously tiw, where the duration of therapy is 48 weeks.

In one embodiment, the present invention provides any of the above-described methods modified to comprise administering to an individual having an HCV infection an effective amount of an α-glucosidase inhibitor; and a regimen of 200 μg monoPEG(30 kD, linear)-ylated consensus IFN-α administered subcutaneously every 10 days or qw; and 100 μg Actimmune® human IFN-γ1b administered subcutaneously tiw, where the duration of therapy is 48 weeks.

Combination Therapies With Ribavirin

In some embodiments, the methods provide for combination therapy comprising administering an α-glucosidase inhibitor, and an effective amount of ribavirin. Ribavirin can be administered in dosages of about 400 mg, about 800 mg, about 1000 mg, or about 1200 mg per day.

In one embodiment, the invention provides any of the above-described methods modified to include co-administering to the patient a therapeutically effective amount of ribavirin for the duration of the desired course of the α-glucosidase inhibitor treatment.

In another embodiment, the invention provides any of the above-described methods modified to include co-administering to the patient about 800 mg to about 1200 mg ribavirin orally per day for the duration of the desired course of the α-glucosidase inhibitor treatment.

In another embodiment, the invention provides any of the above-described methods modified to include co-administering to the patient (a) 1000 mg ribavirin orally per day if the patient has a body weight less than 75 kg or (b) 1200 mg ribavirin orally per day if the patient has a body weight greater than or equal to 75 kg, where the daily dosage of ribavirin is optionally divided into to 2 doses for the duration of the desired course of the α-glucosidase inhibitor treatment.

In some embodiments, the invention provides a combination therapy method using combined effective amounts of an α-glucosidase inhibitor; and ribavirin in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of ribavirin containing an amount of from about 800 mg to about 1200 mg ribavirin orally per day for the duration of the desired course of the α-glucosidase inhibitor treatment.

In some embodiments, the invention provides a combination therapy method using combined effective amounts of an α-glucosidase inhibitor; and ribavirin in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of ribavirin containing an amount of from about 800 mg to about 1200 mg ribavirin orally per day for the duration of the desired course of the α-glucosidase inhibitor treatment.

Combination Therapies With Levovirin

In some embodiments, the methods provide for combination therapy comprising administering an α-glucosidase inhibitor, as described above, and an effective amount of levovirin. Levovirin is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, levovirin is administered orally in dosages of about 400 mg, about 800 mg, about 1000 mg, or about 1200 mg per day for the desired course of the α-glucosidase treatment.

In some embodiments, the invention provides a combination therapy method using combined effective amounts of an α-glucosidase inhibitor; and ribavirin in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of levovirin containing an amount of about 400 mg, 800 mg, 1000 mg, or about 1200 mg orally per day for the duration of the desired course of the α-glucosidase inhibitor treatment.

In some embodiments, the invention provides a combination therapy method using combined effective amounts of an α-glucosidase inhibitor; and levovirin in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of levovirin containing an amount of about 400 mg, 800 mg, 1000 mg, or about 1200 mg orally per day for the duration of the desired course of the α-glucosidase inhibitor treatment.

Combination Therapies With Viramidine

In some embodiments, the methods provide for combination therapy comprising administering α-glucosidase inhibitor, as described above, and an effective amount of viramidine. Viramidine is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, viramidine is administered orally in dosages of about 800 mg, or about 1600 mg per day for the desired course of the α-glucosidase inhibitor treatment.

In some embodiments, the invention provides a combination therapy method using combined effective amounts of an α-glucosidase inhibitor; and viramidine in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of viramidine containing an amount of about 800 mg or about 1600 mg orally per day for the duration of the desired course of the α-glucosidase inhibitor treatment.

In some embodiments, the invention provides a combination therapy method using combined effective amounts of an α-glucosidase inhibitor; and viramidine in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of viramidine containing an amount of about 800 mg or about 1600 mg orally per day for the duration of the desired course of the α-glucosidase inhibitor treatment.

Combination Therapies With Thymosin-α

In some embodiments, the methods provide for combination therapy comprising administering an α-glucosidase inhibitor, as described above, and an effective amount of thymosin-α. Thymosin-α (Zadaxin™) is generally administered by subcutaneous injection. Thymosin-α can be administered tid, bid, qd, qod, biw, tiw, qw, qow, three times per month, once monthly, substantially continuously, or continuously for the desired course of the α-glucosidase inhibitor treatment. In many embodiments, thymosin-α is administered twice per week for the desired course of the α-glucosidase inhibitor treatment.

Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

Thymosin-α can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In one embodiment, thymosin-α is administered for the desired course of the α-glucosidase inhibitor treatment.

In one embodiment, the invention provides a method using an effective amount of ZADAXIN™ thymosin-α and an effective amount of an agent that inhibits enzymatic activity of a membrane-bound α-glucosidase in the treatment of a viral infection in a patient, comprising administering to the patient a dosage of ZADAXIN™ containing an amount of from about 1.0 mg to about 1.6 mg per dose, subcutaneously twice per week for the desired duration of the α-glucosidase inhibitor treatment.

In some embodiments, the invention provides a combination therapy method using combined effective amounts of an α-glucosidase inhibitor; and thymosin-α in the treatment of a flavivirus infection in a patient, the method comprising co-administering to the patient a) a dosage of an α-glucosidase inhibitor containing an amount of from about 10 mg to about 100 mg miglitol, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg miglitol, administered orally tid; and b) a dosage of thymosin-α containing an amount of from about 1.0 mg to about 1.6 mg per dose, subcutaneously twice per week for the desired duration of the α-glucosidase inhibitor treatment.

In some embodiments, the invention provides a combination therapy method using combined effective amounts of an α-glucosidase inhibitor; and thymosin-α in the treatment of a flavivirus infection in a patient, the method comprising co-administering to the patient a) a dosage of an α-glucosidase inhibitor containing an amount of from about 10 mg to about 100 mg acarbose, administered orally tid, e.g., 10 mg, 15 mg, 20 mg, 25 mg, 30 mg, 40 mg, 50 mg, 60 mg, 70 mg, 75 mg, 80 mg, 90 mg, or 100 mg acarbose, administered orally tid; and b) a dosage of thymosin-α containing an amount of from about 1.0 mg to about 1.6 mg per dose, subcutaneously twice per week for the desired duration of the α-glucosidase inhibitor treatment.

Combination Therapy With an HCV Enzyme Inhibitor

In some embodiments, a subject method provides for combination therapy comprising administering an effective amount of an α-glucosidase inhibitor, as described above, and an effective amount of an HCV enzyme inhibitor, in combination therapy for treatment of an HCV infection. In some of these embodiments, the methods provide for combination therapy comprising administering an effective amount of an α-glucosidase inhibitor, as described above, and an effective amount of an NS3 inhibitor, in combination therapy for treatment of an HCV infection. In some of these embodiments, the methods provide for combination therapy comprising administering an effective amount of an α-glucosidase inhibitor, as described above, and an effective amount of an NS5 inhibitor, in combination therapy for treatment of an HCV infection.

In some embodiments, a subject therapeutic regimen involves modifying any of the above-described regimens for HCV infection by administering an HCV enzyme inhibitor. Effective dosages of an HCV enzyme inhibitor range from about 10 mg to about 200 mg per dose, e.g., from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, from about 35 mg to about 40 mg per dose, from about 40 mg per dose to about 45 mg per dose, from about 45 mg per dose to about 50 mg per dose, from about 50 mg per dose to about 60 mg per dose, from about 60 mg per dose to about 70 mg per dose, from about 70 mg per dose to about 80 mg per dose, from about 80 mg per dose to about 90 mg per dose, from about 90 mg per dose to about 100 mg per dose, from about 100 mg per dose to about 125 mg per dose, from about 125 mg per dose to about 150 mg per dose, from about 150 mg per dose to about 175 mg per dose, or from about 175 mg per dose to about 200 mg per dose.

In some embodiments, effective dosages of an HCV enzyme inhibitor are expressed as mg/kg body weight. In these embodiments, effective dosages of an HCV enzyme inhibitor are from about 0.01 mg/kg body weight to about 100 mg/kg body weight, from about 0.1 mg/kg body weight to about 50 mg/kg body weight, from about 0.1 mg/kg body weight to about 1 mg/kg body weight, from about 1 mg/kg body weight to about 10 mg/kg body weigh, from about 10 mg/kg body weight to about 100 mg/kg body weight, from about 5 mg/kg body weight to about 400 mg/kg body weight, from about 5 mg/kg body weight to about 50 mg/kg body weight, from about 50 mg/kg body weight to about 100 mg/kg body weight, from about 100 mg/kg body weight to about 200 mg/kg body weight, from about 200 mg/kg body weight to about 300 mg/kg body weight, or from about 300 mg/kg body weight to about 400 mg/kg body weight.

In many embodiments, an HCV enzyme inhibitor is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The HCV enzyme inhibitor can be administered tid, bid, qd, qod, biw, tiw, qw, qow, three times per month, once monthly, substantially continuously, or continuously.

In many embodiments, multiple doses of an HCV enzyme inhibitor are administered. For example, an HCV enzyme inhibitor is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

As another example, in some embodiments, any of the above-described treatment regimens for treating an HCV infection is modified to include administering a dosage of an HCV NS3 protease inhibitor containing an amount of 0.01 mg to 100 mg of drug per kilogram of body weight orally daily, optionally in two or more divided doses per day, for the desired treatment duration.

As another example, in some embodiments, any of the above-described treatment regimens for treating an HCV infection is modified to include administering a dosage of an HCV NS5B RNA-dependent RNA polymerase inhibitor containing an amount of 0.01 mg to 100 mg of drug per kilogram of body weight orally daily, optionally in two or more divided doses per day, for the desired treatment duration.

As non-limiting examples, any of the above-described methods can be modified to include an NS3 inhibitor regimen comprising administering a dosage of 0.01 mg to 0.1 mg of drug per kilogram of body weight orally daily, optionally in two or more divided doses per day, for the desired treatment duration.

As non-limiting examples, any of the above-described methods can be modified to include an NS3 inhibitor regimen with an NS3 inhibitor regimen comprising administering a dosage of 0.1 mg to 1 mg of drug per kilogram of body weight orally daily, optionally in two or more divided doses per day, for the desired treatment duration.

As non-limiting examples, any of the above-described methods can be modified to include an NS3 inhibitor regimen with an NS3 inhibitor regimen comprising administering a dosage of 1 mg to 10 mg of drug per kilogram of body weight orally daily, optionally in two or more divided doses per day, for the desired treatment duration.

As non-limiting examples, any of the above-described methods can be modified to include an NS3 inhibitor regimen with an NS3 inhibitor regimen comprising administering a dosage of 10 mg to 100 mg of drug per kilogram of body weight orally daily, optionally in two or more divided doses per day, for the desired treatment duration.

As non-limiting examples, any of the above-described methods can be modified to include an NS5B inhibitor regimen comprising administering a dosage of 0.01 mg to 0.1 mg of drug per kilogram of body weight orally daily, optionally in two or more divided doses per day, for the desired treatment duration.

As non-limiting examples, any of the above-described methods can be modified to include an NS5B inhibitor regimen with an NS5B inhibitor regimen comprising administering a dosage of 0.1 mg to 1 mg of drug per kilogram of body weight orally daily, optionally in two or more divided doses per day, for the desired treatment duration.

As non-limiting examples, any of the above-described methods can be modified to include an NS5B inhibitor regimen with an NS5B inhibitor regimen comprising administering a dosage of 1 mg to 10 mg of drug per kilogram of body weight orally daily, optionally in two or more divided doses per day, for the desired treatment duration.

As non-limiting examples, any of the above-described methods can be modified to include an NS5B inhibitor regimen with an NS5B inhibitor regimen comprising administering a dosage of 10 mg to 100 mg of drug per kilogram of body weight orally daily, optionally in two or more divided doses per day, for the desired treatment duration.

Further Variations

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 50 μg of drug per dose, subcutaneously once weekly, once every 8 days, or once every 10 days for the desired treatment duration.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 100 μg of drug per dose, subcutaneously once weekly, once every 8 days, or once every 10 days for the desired treatment duration.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 150 μg of drug per dose, subcutaneously once weekly, once every 8 days, or once every 10 days for the desired treatment.

As non-limiting examples, any of the above-described methods featuring an IFN-α regimen can be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 200 μg of drug per dose, subcutaneously once weekly, once every 8 days, or once every 10 days for the desired treatment duration.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 1 μg of drug per dose, subcutaneously once daily or three times per week for the desired treatment duration.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 3 μg of drug per dose, subcutaneously once daily or three times per week for the desired treatment duration.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 9 μg of drug per dose, subcutaneously once daily or three times per week for the desired treatment duration.

As non-limiting examples, any of the above-described methods featuring an IFN-α regimen can be modified to replace the subject IFN-α regimen with a regimen of INFERGEN® interferon alfacon-1 comprising administering a dosage of INFERGEN® interferon alfacon-1 containing an amount of 15 μg of drug per dose, subcutaneously once daily or three times per week for the desired treatment duration.

As non-limiting examples, any of the above-described methods featuring an IFN-γ regimen can be modified to replace the subject IFN-γ regimen with a regimen of IFN-γ comprising administering a dosage of IFN-γ containing an amount of 25 μg of drug per dose, subcutaneously three times per week for the desired treatment duration.

As non-limiting examples, any of the above-described methods featuring an IFN-γ regimen can be modified to replace the subject IFN-γ regimen with a regimen of IFN-γ comprising administering a dosage of IFN-γ containing an amount of 50 μg of drug per dose, subcutaneously three times per week for the desired treatment duration.

As non-limiting examples, any of the above-described methods featuring an IFN-γ regimen can be modified to replace the subject IFN-γ regimen with a regimen of IFN-γ comprising administering a dosage of IFN-γ containing an amount of 100 μg of drug per dose, subcutaneously three times per week for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 50 μg of drug per dose, subcutaneously once weekly, once every 8 days, or once every 10 days; and (b) administering a dosage of IFN-γ containing an amount of 25 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 25 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 25 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 25 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 25 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 50 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 100 μg of drug per dose, subcutaneously three times per week; for the desired treatment duration.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 100 μg of drug per dose, subcutaneously three times per week for the desired treatment duration.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2a comprising administering a dosage of peginterferon alfa-2a containing an amount of 180 μg of drug per dose, subcutaneously once weekly for the desired treatment duration.

As non-limiting examples, any of the above-described methods that includes a regimen of monoPEG (30 kD, linear)-ylated consensus IFN-α can be modified to replace the regimen of monoPEG (30 kD, linear)-ylated consensus IFN-α with a regimen of peginterferon alfa-2b comprising administering a dosage of peginterferon alfa-2b containing an amount of 1.0 μg to 1.5 μg of drug per kilogram of body weight per dose, subcutaneously once or twice weekly for the desired treatment duration.

As non-limiting examples, any of the above-described methods can be modified to include administering a dosage of ribavirin containing an amount of 400 mg, 800 mg, 1000 mg or 1200 mg of drug orally per day, optionally in two or more divided doses per day, for the desired treatment duration.

As non-limiting examples, any of the above-described methods can be modified to include administering a dosage of ribavirin containing (i) an amount of 1000 mg of drug orally per day for patients having a body weight of less than 75 kg or (ii) an amount of 1200 mg of drug orally per day for patients having a body weight of greater than or equal to 75 kg, optionally in two or more divided doses per day, for the desired treatment duration.

Combination Therapies With Other Antiviral Agents

Other antiviral agents are contemplated for use in combination therapies described herein. For example, ribozymes such as Heptazyme™ and phosphorothioate oligonucleotides which are complementary to HCV protein sequences and which inhibit the expression of viral core proteins are also suitable for use in combination therapies described herein.

In some embodiments, the additional antiviral agent(s) is administered during the entire course of treatment with an α-glucosidase inhibitor, and the beginning and end of the treatment periods coincide. In other embodiments, the additional antiviral agent(s) is administered for a period of time that is overlapping with that of the α-glucosidase inhibitor treatment, e.g., treatment with the additional antiviral agent(s) begins before the α-glucosidase inhibitor treatment begins and ends before the α-glucosidase inhibitor treatment ends; treatment with the additional antiviral agent(s) begins after the α-glucosidase inhibitor treatment begins and ends after the α-glucosidase inhibitor treatment ends; treatment with the additional antiviral agent(s) begins after the α-glucosidase inhibitor treatment begins and ends before the α-glucosidase inhibitor treatment ends; or treatment with the additional antiviral agent(s) begins before the α-glucosidase inhibitor treatment begins and ends after the α-glucosidase inhibitor treatment ends.

The α-glucosidase inhibitor can be administered together with (i.e., simultaneously in separate formulations; simultaneously in the same formulation; administered in separate formulations and within about 48 hours, within about 36 hours, within about 24 hours, within about 16 hours, within about 12 hours, within about 8 hours, within about 4 hours, within about 2 hours, within about 1 hour, within about 30 minutes, or within about 15 minutes or less) one or more additional antiviral agents.

Patient Identification

In certain embodiments, the specific regimen of drug therapy used in treatment of the HCV patient is selected according to certain disease parameters exhibited by the patient, such as the initial viral load, genotype of the HCV infection in the patient, liver histology and/or stage of liver fibrosis in the patient.

Thus, in some embodiments, the present invention provides any of the above-described methods for the treatment of HCV infection in which the subject method is modified to treat a treatment failure patient for a duration of 48 weeks.

In other embodiments, the invention provides any of the above-described methods for HCV in which the subject method is modified to treat a non-responder patient, where the patient receives a 48 week course of therapy.

In other embodiments, the invention provides any of the above-described methods for the treatment of HCV infection in which the subject method is modified to treat a relapser patient, where the patient receives a 48 week course of therapy.

In other embodiments, the invention provides any of the above-described methods for the treatment of HCV infection in which the subject method is modified to treat a naïve patient infected with HCV genotype 1, where the patient receives a 48 week course of therapy.

In other embodiments, the invention provides any of the above-described methods for the treatment of HCV infection in which the subject method is modified to treat a naïve patient infected with HCV genotype 4, where the patient receives a 48 week course of therapy.

In other embodiments, the invention provides any of the above-described methods for the treatment of HCV infection in which the subject method is modified to treat a naïve patient infected with HCV genotype 1, where the patient has a high viral load (HVL), where "HVL" refers to an HCV viral load of greater than $2 \times 10^6$ HCV genome copies per mL serum, and where the patient receives a 48 week course of therapy.

In one embodiment, the invention provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

In another embodiment, the invention provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 40 weeks to about 50 weeks, or about 48 weeks.

In another embodiment, the invention provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

In another embodiment, the invention provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 40 weeks to about 50 weeks, or about 48 weeks.

In another embodiment, the invention provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

In another embodiment, the invention provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 40 weeks to about 50 weeks, or about 48 weeks.

In another embodiment, the invention provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

In another embodiment, the invention provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 24 weeks.

In another embodiment, the invention provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 24 weeks to about 48 weeks.

In another embodiment, the invention provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

In another embodiment, the invention provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

In another embodiment, the invention provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 24 weeks.

In another embodiment, the invention provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of at least about 24 weeks.

In another embodiment, the invention provides any of the above-described methods for the treatment of an HCV infection, where the subject method is modified to include the steps of (1) identifying a patient having an HCV genotype 1 or 4 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

In another embodiment, the invention provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of about 20 weeks to about 50 weeks.

In another embodiment, the invention provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of at least about 24 weeks and up to about 48 weeks.

Subjects Suitable for Treatment

The subject methods are suitable for treating individuals having, or susceptible to having, an alphavirus infection, e.g., a flavivirus infection (e.g., an HCV infection, etc.). The subject methods are also suitable for treating individuals who have been previously treated for an alphavirus infection with an agent (other than an α-glucosidase inhibitor as discussed above) and are refractory to treatment with the agent, and who have either failed the previous treatment; or who cannot tolerate treatment with the non-α-glucosidase agent; or who responded to the previous treatment and relapsed. In many embodiments, the individual is a human.

Individuals who have been clinically diagnosed as infected with an alphavirus are suitable for treatment with a method of the instant invention. Of particular interest in some embodiments are individuals who have been clinically diagnosed as infected with a hepatitis virus (e.g., HAV, HBV, HCV, delta, etc.), particularly HCV. Of particular interest in other embodiments are individuals who have been clinically diagnosed as infected with West Nile Virus.

Individuals who are to be treated according to the methods of the invention include individuals who have been clinically diagnosed as infected with HCV. Individuals who are infected with HCV are identified as having HCV RNA in their blood, and/or having anti-HCV antibody in their serum.

Individuals who are clinically diagnosed as infected with HCV include naive individuals (e.g., individuals not previously treated for HCV, particularly those who have not previously received IFN-α-based and/or ribavirin-based therapy) and individuals who have failed prior treatment for HCV ("treatment failure" patients). Treatment failure patients include non-responders (i.e., individuals in whom the HCV titer was not significantly or sufficiently reduced by a previous treatment for HCV, e.g., a previous IFN-α monotherapy, a previous IFN-α and ribavirin combination therapy, or a previous pegylated IFN-α and ribavirin combination therapy); and relapsers (i.e., individuals who were previously treated for HCV, e.g., who received a previous IFN-α monotherapy, a previous IFN-α and ribavirin combination therapy, or a previous pegylated IFN-α and ribavirin combination therapy, whose HCV titer decreased, and subsequently increased).

In particular embodiments of interest, individuals have an HCV titer of at least about $10^5$, at least about $5 \times 10^5$, or at least about $10^6$, or at least about $2 \times 10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also of interest are HCV-positive individuals (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment with IFN-α-based therapies or who cannot tolerate IFN-α-based therapies, or who have a contraindication to such therapies. In particular embodiments of interest, HCV-positive individuals with stage 3 or 4 liver fibrosis according to the METAVIR scoring system are suitable for treatment with the methods of the present invention. In other embodiments, individuals suitable for treatment with the methods of the instant invention are patients with decompensated cirrhosis with clinical manifestations, including patients with far-advanced liver cirrhosis, including those awaiting liver transplantation. In still other embodiments, individuals suitable for treatment with the methods of the instant invention include patients with milder degrees of fibrosis including those with early fibrosis (stages 1 and 2 in the METAVIR, Ludwig, and Scheuer scoring systems; or stages 1, 2, or 3 in the Ishak scoring system.).

In some embodiments of interest, a subject is an individual who is HCV infected and who is diabetic, e.g. who has either Type I diabetes or Type II diabetes.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Effect of α-Glucosidase Inhibitors on Viral Replication in in vitro Cell Culture Materials and Methods Cells and Virus.

A bovine turbinate (BT) intestinal cell line (ATCC-CRL1390) and Madin-Darby bovine kidney cells (ATCC-CCL22) were grown in DMEM/F12 (Gibco/BRL, Gaithersburg, Md.) supplemented with 10% heat-inactivated horse serum (Gibco/BRL). A549 cells (ATCC-CCL185) were maintained in culture medium supplemented 10% fetal bovine serum (Gibco/BRL). BVDV cytopathic strain NADL (ATCC-VR534) and Vesicular stomatitis virus (VSV) Indiana serotype were used in this study. The virus stock was plaque purified three times on BT cell monolayers prior to large scale virus stock preparation. The titers of stock solution of the virus was determined to be $6\times10^5$ PFU/ml.

Alpha-Glucosidase Inhibitors, and IFM.

Castanospermine (CTS) (Calbiochem, La Jolla, Calif.) was prepared as a concentrated stock at 100 mM in water. Acarbose (Precose; Bayer) and miglitol (Glycet; Pharmacia) were obtained from commercial sources. Both of CTS and acarbose were prepared in water at 100 mM. Infergen consensus alpha interferon (CIFN) and Actimmune interferon gamma (InterMune, Brisbane, Calif.) were diluted in MDBK media at 10 ng/ml and 100 ng/ml.

BVDV Reduction Assay.

MDBK monolayers ($5\times10^4$ per well of a 96 well plate) were infected with BVDV strain NADL at multiplicity of infection (MOI)=0.01 or 0.005. At 1 hour post-infection, the inoculum was removed and the cultures were washed twice in MDBK media. Media containing acarbose, miglitol, CST, or interferons (IFNs) alone or in combinations were added to the cultures. At 48 hours to 72 hours post-infection, the cultures were harvested and frozen at −70° C. before being used for viral RNA purification.

VSV, BVDV single-Cycle Replication.

A549 or MDBK cells ($5\times10^4$ per well of a 96 well plate) were infected in triplicate at a multiplicity of infection of >1 or MOI=0.01. At 1 hour post-infection, the inoculum was removed and the culture was washed twice with 100 ul of A549 or MDBK media. Media containing acarbose, miglitol, CST, or IFNs alone or in combinations were added to the cultures. At 24 hours post-infection, the cultures were harvested and frozen at −70° C. before being used for viral RNA purification.

Viral RNA Purification and Real-Time RT-PCR Analysis.

RNA from released viral particles was purified using the QIAamp vial RNA purification kit (Qiagen) with 140 ul of culture supernatant as the stating material. Serial dilutions of VSV RNA or BVDV RNA were prepared from samples of infected cell cultures and used as absolute standards for quantitation of viral RNA. Each plaque was assumed to be the result of cell death caused by the progeny of one infective virus, thus the virus titer was expressed as plaque forming units (PFU) per ml, which is equivalent to copies per ml. Each sample was measured in triplicate, using the ABI Prism 7900HT Sequence Detection System (Applied Biosystems). The primers used for real-time reverse transcription polymerase chain reaction (RT-PCR) amplification of fragments of BVDV (AJ133738) 5' non-translated region (NTR) were (a) sense 5'-CCATGCCCTTAGTAGGACTAGCA-3' (SEQ ID NO:1) and (b) antisense 5'-TTCCAAGGCGTCGAACCA-3' (SEQ ID NO:2). The TaqMan probe was 5'-AACAGTGGTGAGTTCGTTGGATGGCTTAAG-3' (SEQ ID NO:3) for 5'NTR. The primers used for real-time RT-PCR amplification of fragments of BVDV (AJ133738) NS5B regions were (a) sense 5'-GTTGGAGATTTTCCACACGATAGC-3' (SEQ ID NO:4) and (b) antisense 5'-CCCCGCCTCAAGTTGCT-3' (SEQ ID NO:5). The TaqMan probe was 5'-CAACCCACCCTGAAACACACCTACGG-3' (SEQ ID NO:6) for the NS5B region. TaqMan FAM/TAMRA-labeled hybridization probes were supplied as mixtures and were used in a 50 μl single tube PCR reaction. The reverse transcription (RT) step was performed at 48° C. for 30min, followed by 10 min at 95° C., then followed by 40 cycles of 15 seconds at 95° C. and 1 minute at 60° C.

Results and Discussion

The results of the VSV and BVDV single-cycle replication assays indicated that VSV and BVDV replication is sensitive to glucosidase inhibitors. In cells infected with VSV at a multiplicity of infection (MOI)>1, none of the glucosidase inhibitors (miglitol, acarbose and positive control CTS, which prevents the action of glucosidase I and II) exhibited antiviral activity. In VSV-infected cells at MOI=0.01, all of the glucosidase inhibitors (miglitol, acarbose and positive control CTS) exhibited antiviral activity at a concentration of 1 mM. Although only the positive control CTS exhibited antiviral activity in BVDV-infected cells at MOI>1, all of the glucosidase inhibitors (miglitol, acarbose and positive control CTS) exhibited antiviral activity in BVDV-infected cells at MOI=0.05 [v. 0.005] (data shown in FIGS. 1-3).

The results of the BVDV viral reduction assays indicated that both miglitol and acarbose are potent antiviral agents that inhibit BVDV replication.

Example 2

Effect of Combinations of α-Glucosidase Inhibitors and IFN-α on Viral Replication in in vitro Cell Culture The reduction in viral infectivity caused by miglitol is been performed in BVDV, a surrogate model for HCV. MDBK cells were infected by BVDV virus first, and then were treated by miglitol alone or combined with CIFN. After 48 hrs treatments, the BVDV virus was tested to compare with untreated cells by real-time PCR. The results are shown in FIGS. 5-12. Table 2 provides the concentrations (in pg/ml CIFN and μM miglitol) of CIFN and miglitol in the combinations depicted in FIG. 7.

TABLE 2

| | |
|---|---|
| combo 1 | CIFN 450 + miglitol 450 |
| combo 2 | CIFN 150 + miglitol 150 |
| combo 3 | CIFN 50 + miglitol 50 |
| combo 4 | CIFN 16.7 + miglitol 16.7 |
| combo 5 | CIFN 5.6 + miglitol 5.6 |

The results indicate that miglitol has an anti-viral potential in HCV patients. The results further indicate that miglitol plus CIFN has a synergistic effect: Combination Index (CI) value in ED50 is 0.86 (slight synergism), in ED 75 is 0.71 (moderate synergism) and ED 90 is 0.58 (synergism), respectively. The data are depicted in Table 3, below.

TABLE 3

| Drug | Combination Index Values at ED50 | ED75 | ED90 | Dm | m | r |
|---|---|---|---|---|---|---|
| COMBO mean (1:1) | 0.85285<br>0.85697 | 0.6994<br>0.70455 | 0.57605<br>0.58249 | 1.07223<br>Mutually non-exclusive | 0.32336 | 0.98042 |
| CIFN | N/A | N/A | N/A | 1.26443 | 0.3051 | 0.96475 |
| miglitol | N/A | N/A | N/A | 220.7982 | 0.36987 | 0.95355 |

Example 3

Effect of Combinations of α-Glucosidase Inhibitors and/or IFN-α and/or an HCV NS3 Protease Inhibitor on Viral Replication in in vitro Cell Culture The redu

TABLE 8

| NS3 (nM) + miglitol (uM) (1:4) | BVDV vRNA copy | BVDV vRNA copy | Mean BVDV vRNA Copy | IC50 | Standard Deviation |
|---|---|---|---|---|---|
| 200.00 | 9,903.573 | 9,519.9045 | 9,711.73875 | 96.6 | 191.8 |
| 100.00 | 96,224.62 | 10,155.769 | 53,190.1945 | 81.5 | 43,034.4 |
| 50.00 | 105,968.4 | 88,732.51 | 97,350.45 | 66.2 | 8,617.9 |
| 25.00 | 96,991.73 | 104,053.125 | 100,522.4275 | 65.1 | 3,530.7 |
| 12.50 | 101,847.5 | 114,010.137 | 107,928.8085 | 62.5 | 6,081.3 |
| 6.25 | 132,863.1 | 124,937.25 | 128,900.155 | 55.3 | 3,962.9 |
| 3.13 | 144,261.5 | 137,993.336 | 141,127.418 | 51.0 | 3,134.1 |
| 1.56 | 181,269.3 | 172,079.26 | 176,674.285 | 38.7 | 4,595.0 |
| 0.78 | 204,120.6 | 164,474.562 | 184,297.591 | 36.0 | 19,823.0 |
| 0.39 | 203,088 | 204,666.99 | 203,877.495 | 29.2 | 789.5 |
| Mock | 288,147.44 | | | | |

TABLE 9

| CIFN (pg/ml) + miglitol (uM) + NS3 (nM) (1:3.125:12.5) | BVDV vRNA copy | BVDV vRNA copy | Mean BVDV vRNA Copy | IC50 | Standard Deviation |
|---|---|---|---|---|---|
| 64 | 878.925 | 790.69156 | 834.80828 | 99.7 | 44.1 |
| 32 | 18,100.62 | 18,440.3257 | 18,270.47285 | 93.5 | 169.9 |
| 16 | 37,153.125 | 35,230.028 | 36,191.5765 | 87.1 | 961.5 |
| 8 | 44,393.77 | 41,493.951 | 42,943.8605 | 84.7 | 1,449.9 |
| 4 | 59,090.88 | 58,344.75 | 58,717.815 | 79.1 | 373.1 |
| 2 | 135,737.77 | 123,298.062 | 129,517.916 | 53.9 | 6,219.9 |
| 1 | 135,542.05 | 138,580.41 | 137,061.23 | 51.3 | 1,519.2 |
| 0.5 | 157,368.77 | 132,176.69 | 144,772.73 | 48.5 | 12,596.0 |
| 0.25 | 180,111.42 | 174,488.363 | 177,299.8915 | 37.0 | 2,811.5 |
| 0.125 | 194,642.1 | 193,841.48 | 194,241.79 | 30.9 | 400.3 |
| Mock | 281,254.88 | | | | |

The results demonstrate that miglitol plus CIFN and/or an NS3 protease inhibitors have synergistic effects. The results showed that CIFN+miglitol, the Combination Index Values (CI) at ED90 is 0.31 (indicating strong synergism); in HCV NS3/4 protease inhibitor+miglitol, the CI values at ED90 is 0.40 (indicating synergism); and in CIFN+miglitol+NS3/4 protease inhibitor, the CI values at ED90 is 0.077 (indicating very strong synergism). The combination resulted in a 4.8 fold decrease in the EC90 of CIFN combined with miglitol and 48 fold decreases in the EC90 of CIFN combined with miglitol and HCV NS3/4 protease inhibitor together.

TABLE 10

| | Dosage @ ED50 | CI @ ED50 | Dosage @ ED75 | CI @ ED75 | Dosage @ ED90 | CI @ ED90 |
|---|---|---|---|---|---|---|
| CIFN (pg/ml) + miglitol (uM) (1:12.5) | 2.72 pg/ml + 34.04 uM | 0.76 | 14.79 pg/ml + 184.91 uM | 0.48 | 80.35 pg/ml + 1004.37 uM | 0.31 |
| NS3 (nM) + miglitol (uM) (1:4) | 3.41 nM + 13.64 uM | 0.33 | 26.22 nM + 104.86 uM | 0.36 | 201.52 pg/ml + 806.07 uM | 0.40 |
| CIFN (pg/ml) + NS3 (nM) + miglitol (uM) (1:3.125:12.5) | 0.68 pg/ml + 2.11 nM + 8.46 uM | 0.34 | 2.44 pg/ml + 7.63 nM + 30.53 uM | 0.16 | 8.82 pg/ml + 27.57 nM + 110.28 uM | 0.07 |

Example 4

Methods for Treating HCV With the Addition of NS5b RdRp Inhibitors

The present invention provides methods for testing the effectiveness of co-treating with alpha-glucosidase and NS5b RdRp inhibitors.

Materials and Methods

Cells and Virus.

A bovine turbinate (BT) intestinal cell line (ATCC-CRL1390) and Madin-Darby bovine kidney cells (ATCC-CCL22) are grown in DMEM/F12 (Gibco/BRL, Gaitherburg, Md.) supplemented with 10% heat-inactivated horse serum (Gibco/BRL). A549 cells (ATCC-CCL185) are maintained in culture medium supplemented with 10% fetal bovine serum (Gibco/BRL). BVDV cytopathic strain NADL (ATCC-VR534) and Vesicular stomatitis virus (VSV) Indiana serotype are used in this study. The virus stock is plaque purified three times on BT cell monolayers prior to large scale virus stock preparation. The titers of stock solution of the virus is determined to be $6 \times 10^5$ PFU/ml.

Alpha-Glucosidase Inhibitors, IFN and HCV NS5b RdRp Inhibitors.

Castanospermine (CTS) (Calbiochem, La Jolla, Calif.) is prepared as a concentrated stock at 100 mM in water. CTS and acarbose are prepared in water at 100 mM. Infergen consensus alpha interferon (CIFN) and Actimmune interferon gamma (Intermune, Brisbane, Calif.) are diluted in MDBK media at 10 ng/ml and 100 ng/ml. Two NS5b RdRp inhibitors: 2'-O-Me-C (IC50 20 mM in replicon JBC 2003, p 11979) and 2'-F—C (EC90 5 mM in replicon, Antimicrobal Agents and Chemother, 2004, p 651) are also used.

BVDV Reduction Assay.

MDBK monolayers ($5 \times 10^4$ per well of a 96 well plate) are infected with BVDV strain NADL at multiplicity of infection (MOI)=0.01 or 0.005. At 1 hour post-infection, the inoculum is removed and the cultures are washed twice in MDBK media. Media containing acarbose, miglitol, CST, interferons (IFNs) or NS5b RdRp inhibitors alone or in combination are added to the cultures. At 48 hours to 72 hours post-infection, the cultures are harvested and frozen at $-70°$ C. before being used for viral RNA purification.

VSV, BVDV Single-Cycle Replication.

A549 or MDBK cells ($5 \times 10^4$ per well of a 96 well plate) are infected in triplicate at a multiplicity of infection of >1 or MOI=0.01. At 1 hour post-infection, the inoculum is removed and the culture is washed twice with 100 ul of A549 or MDBK media. Media containing acarbose, miglitol, CST, IFNs or NS5b RdRp inhibitors alone or in combination are added to the cultures. At 24 hours post-infection, the cultures are harvested and frozen at $-70°$ C. before being used for viral RNA purification.

Viral RNA Purification and Real-Time RT-PCR Analysis.

RNA from released viral particles is purified using the QIAamp vial RNA purification kit (Qiagen) with 140 ul of culture supernatant as the starting material. Serial dilutions of VSV RNA or BVDV RNA are prepared from samples of infected cell cultures and used as absolute standards for quantization of viral RNA. Each plaque is assumed to be the result of cell death caused by the progeny of one infective virus, thus the virus titer is expressed as plaque forming units (PFU) per ml, which is equivalent to copies per ml. Each sample is measured in triplicate, using the ABI Prism 7900HT Sequence Detection System (Applied Biosystems). The primers to be used for real-time reverse transcription polymerase chain reaction (RT-PCR) amplification of fragments of BVDV (AJ 133738) 5' non-translated region (NTR) are (a) sense 5'-CCATGCCCTTAGTAGGACTAGCA-3' (SEQ ID NO:1) and (b) antisense 5'-TTCCAAGGCGTCGAACCA-3' (SEQ ID NO:2). The TaqMan probe is 5'-AACAGTGGT-GAGTTCGTTGGATGGCTTAAG-3' (SEQ ID NO:3) for 5'NTR. The primers to be used for real-time RT-PCR amplification of fragments of BVDV (AJ133738) NS5B regions are (a) sense 5'-GTTGGAGATTTTCCACACGATAGC-3' (SEQ ID NO:4) and (b) antisense 5'-CCCCGCCTCAAGT-TGCT-3' (SEQ ID NO:5). The TaqMan probe is 5'-CAAC-CCACCCTGAAACACACCTACGG-3' (SEQ ID NO:6) for the NS5B region. TaqMan FAM/TAMRA-labeled hybridization probes are supplied as mixtures and are to be used in a 50 μl single tube PCR reaction. The reverse transcription (RT) step is to be performed at 48° C. for 30min, followed by 10 min at 95° C., then followed by 40 cycles of 15 seconds at 95° C. and 1 minute at 60° C.

Results and Discussion

After the above treatments, the results will indicate whether VSV and BVDV replication is sensitive or not sensitive to NS5b RdRp inhibitors. The cells may be sensitive at a MOI>1, at a MOI>0.01, at a MOI≦0.01, or at a MOI=0.05. Sensitivity is determined by the presence of antiviral activity, the determination of which is well known in the art.

In one embodiment, NS5b RdRp inhibitors exhibit antiviral activity.

In another embodiment, alpha-glucosidase and NS5b RdRp inhibitors are effective to produce a reduction in viral infectivity.

In another embodiment, alpha-glucosidase and NS5b RdRp inhibitors are effective antiviral agents in combination to inhibit BVDV replication.

In another embodiment, the combination effect of alpha-glucosidase and NS5b RdRp inhibitors is greater than the effect of either alpha-glucosidase or NS5b RdRp inhibitors alone.

In another embodiment, an effective amount of alpha-glucosidase inhibitor and NS5b RdRp inhibitor is an amount that is effective to reduce the viral load in a patient.

In one embodiment, an effective amount of alpha-glucosidase inhibitor and NS5b RdRp inhibitor is an amount that is effective to achieve SVR in a patient.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a flavivirus infection in an individual, the method comprising administering to an individual in need thereof an effective amount of an agent that inhibits enzymatic activity of a membrane-bound α-glucosidase, wherein the agent is not an imino sugar.

2. The method of claim 1, wherein the agent inhibits the p7 protein of hepatitis C virus.

3. The method of claim 1, wherein the agent is acarbose or castanospermine.

4. A method of treating a flavivirus infection in an individual, the method comprising administering to an individual in need thereof effective amounts of an α-glucosidase inhibitor and at least one additional therapeutic agent, wherein the α-glucosidase inhibitor is not an imino sugar.

5. The method of claim 4, wherein the at least one additional therapeutic agent comprises an interferon-α (IFN-α).

6. The method of claim 5, wherein the IFN-α is interferon alfacon-1.

7. The method of claim 6, wherein the IFN-α is pegylated.

8. The method of claim 7, wherein the pegylated IFN-α is selected from peginterferon alfa-2a, peginterferon alfa-2b, and monoPEG (30 kD, linear)-ylated consensus IFN-α.

9. The method of claim 6, wherein the IFN-α is hyperglycosylated.

10. The method of claim 4, wherein the at least one additional therapeutic agent comprises an interferon-γ(IFN-γ).

11. The method of claim 10, wherein the IFN-γ is interferon γ-1b.

12. The method of claim 11, wherein the IFN-γ is pegylated.

13. The method of claim 11, wherein the IFN-γ is hyperglycosylated.

14. The method of claim 4, wherein the at least one additional therapeutic agent comprises an HCV NS3 protease inhibitor.

15. The method of claim 4, wherein the at least one additional therapeutic agent comprises an HCV NS5B RNA-dependent RNA polymerase inhibitor.

16. The method of claim 4, wherein the at least one additional therapeutic agent comprises a nucleoside analog.

17. The method of claim 16, wherein the nucleoside analog is selected from viramidine, ribavirin, and levovirin.

18. The method of claim 4, wherein the α-glucosidase inhibitor is acarbose or castanospermine.

19. The method of claim 1 or 4, wherein the α-glucosidase inhibitor is administered at a dosage selected from the group consisting of: about 10 mg—about 30 mg per day; about 30 mg—about 60 mg per day; about 10 mg three times daily; about 15 mg three times daily; and about 20 mg three times daily.

20. The method of any one of claims 1, 2, 3, 4-17 or 18, wherein the individual is a human.

* * * * *

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: synthetic primer

<400> SEQUENCE: 1
ccatgccctt agtaggacta gca                                              23

<210> SEQ ID NO 2
<211> LENGTH: 18
<212> TYPE: DNA
<213> ORGANISM: Artificial Sequence
<220> FEATURE:
<223> OTHER INFORMATION: synthetic primer

<400> SEQUENCE: 2
ttccaaggcg tcgaacca                                                    18

<210> SEQ ID NO 3
<211> LENGTH: 30
<212> TYPE: DNA
<213> ORGANISM: Artificial Sequence
<220> FEATURE:
<223> OTHER INFORMATION: synthetic probe

<400> SEQUENCE: 3
aacagtggtg agttcgttgg atggcttaag                                       30

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
gttggagatt tccacacga tagc                                              24

<210> SEQ ID NO 5
<211> LENGTH: 17
<212> TYPE: DNA
<213> ORGANISM: Artificial Sequence
<220> FEATURE:
<223> OTHER INFORMATION: synthetic primer

<400> SEQUENCE: 5
ccccgcctca agttgct                                                     17

<210> SEQ ID NO 6
<211> LENGTH: 26
<212> TYPE: DNA
<213> ORGANISM: Artificial Sequence
<220> FEATURE:
<223> OTHER INFORMATION: synthetic probe

<400> SEQUENCE: 6
caacccaccc tgaaacacac ctacgg                                           26
```